United States Patent
Heo et al.

(10) Patent No.: US 9,914,737 B2
(45) Date of Patent: Mar. 13, 2018

(54) TRIAZOLOPYRIMIDINONE OR TRIAZOLOPYRIDINONE DERIVATIVES, AND USE THEREOF

(71) Applicant: ST PHARM CO., LTD., Siheung-si (KR)

(72) Inventors: Jung Nyoung Heo, Daejeon (KR); Hwan Jung Lim, Daejeon (KR); Kwang Rok Kim, Daejeon (KR); Kyung Jin Kim, Siheung-si (KR); Uk Il Kim, Siheung-si (KR); Hyung Tae Bang, Siheung-si (KR); Ji Hye Yoon, Siheung-si (KR)

(73) Assignee: ST PHARM CO., LTD., Siheung-si (KR)

( * ) Notice: Subject to any disclaimer, the term of this patent is extended or adjusted under 35 U.S.C. 154(b) by 0 days.

(21) Appl. No.: 15/325,651

(22) PCT Filed: Jul. 10, 2015

(86) PCT No.: PCT/KR2015/007219
§ 371 (c)(1),
(2) Date: Jan. 11, 2017

(87) PCT Pub. No.: WO2016/006974
PCT Pub. Date: Jan. 14, 2016

(65) Prior Publication Data
US 2017/0145016 A1    May 25, 2017

(30) Foreign Application Priority Data

Jul. 11, 2014 (KR) .................. 10-2014-0087798
May 15, 2015 (KR) .................. 10-2015-0068375

(51) Int. Cl.
*A01N 43/90* (2006.01)
*A61K 31/519* (2006.01)
*C07D 239/00* (2006.01)
*C07D 471/00* (2006.01)
*C07D 487/00* (2006.01)
*C07D 491/00* (2006.01)
*C07D 487/04* (2006.01)

(52) U.S. Cl.
CPC ................. *C07D 487/04* (2013.01)

(58) Field of Classification Search
None
See application file for complete search history.

(56) References Cited

FOREIGN PATENT DOCUMENTS

| KR | 10-2014-0051944 A | 5/2014 |
| WO | WO-2008/071650 A2 | 6/2008 |
| WO | WO-2013/143663 A1 | 10/2013 |
| WO | WO-2013/182546 A1 | 12/2013 |
| WO | WO-2013/182580 A1 | 12/2013 |

OTHER PUBLICATIONS

Bae J. et al., "Tankyrase 1 Interacts with Mcl-1 Proteins and Inhibits Their Regulation of Apoptosis", *J. Biol. Chem.*, (2003), 278: 5195-5204.
Chang W. et al., "NuMA is a major acceptor of poly(ADP-ribosyl)ation by tankyrase 1 in mitosis", *Biochem. J.*, (2005), 391:177-184.
Chen B. et al., "Small molecule-medicated disruption of Wnt-dependent signaling in tissue regeneration and cancer", *Nature Chemical Biology*, (2009), 5(2):100-107.
Chi N. et al., "Tankyrase Is a Golgi-associated Mitogen-activated Protein Kinase Substrate That Interacts with IRAP in GLUT4 Vesicles", *J. Biol. Chem.*, (2000), 275: 38437-38444.
Chiang, Y.J. et al., "Tankyrase 1 and Tankyrase 2 Are Essential but Redudant for Mouse Embryonic Development", *PLoS One*, (2008), 3(7): e2639.
Huang S.A. et al., "Tankyrase inhibition stabilizes axin and antagonizes Wnt signaling", *Nature*, (2009), 461:614-620.
Liu W. et al., "Mutations in *AXIN2* cause colorectal cancer with defective mismatch repair by activating β-catenin/ TCF signaling", *Nat. Genet.*, (2000), 26: 146-147.
Miyaki M. et al. "Characteristics of Somatic Mutation of the Adenomatous Polyposis Coli Gene in Colorectal Tumors", *Cancer Res.*, (1994) 54:3011-3020.
Taniguchi K. et al. "Mutational spectrum of β-catenin, AXIN1, and AXIN2 in hepatocellular carcinomas and hepatoblastomas", *Oncogene*, (2002) 21:4863-4871.
Waaler J. et al., "A Novel Tankyrase Inhibitor Decreases Canonical Wnt Signaling in Colon Carcinoma Cells and Reduces Tumor Growth in Conditional APC Mutant Mice", *Cancer Res.*, (2012) 72(11):2822-2832.
Wahlbert E. et al., "Family-wide chemical profiling and structural analysis or PARP and tankyrase inhibitors", *Nat. Biotechnol*, (2012),30(3):283-288.
Schreiber V. et al., "Poly(ADP-ribose): novel functions for an old molecule", *Nature Reviews Molecular Cell Biology*, (Jul. 2006), 7:517-528.

*Primary Examiner* — Jeffrey H Murray
(74) *Attorney, Agent, or Firm* — Morrison & Foerster LLP

(57) ABSTRACT

The present invention relates to a novel triazolopyrimidinone or triazolopyridinone derivative, a tautomer thereof, a stereoisomer thereof and their mixture, or a pharmaceutically acceptable salt thereof; and a pharmaceutical composition for preventing or treating a tankyrase-related disease, which contains the same as an active ingredient.

8 Claims, No Drawings

TRIAZOLOPYRIMIDINONE OR TRIAZOLOPYRIDINONE DERIVATIVES, AND USE THEREOF

CROSS-REFERENCE TO RELATED APPLICATIONS

This application is a US national phase application under 35 U.S.C. § 371 of International Application No. PCT/KR2015/007219, filed on Jul. 10, 2015, which claims the priority benefit of Korean Patent Application No. 10-2014-0087798, filed on Jul. 11, 2014, and Korean Patent Application No. 10-2015-0068375, filed on May 15, 2015, the disclosures of all of which are hereby incorporated by reference in their entirety.

TECHNICAL FIELD

The present invention relates to a novel triazolopyrimidinone or triazolopyridinone derivative, a tautomer thereof, a stereoisomer thereof and their mixture, or a pharmaceutically acceptable salt thereof; and a pharmaceutical composition for preventing or treating a tankyrase-related disease, which contains the same as an active ingredient.

BACKGROUND ART

Human tankyrase belongs to the family of poly(ADP-ribose) polymerase (PARP) proteins which consists of 17 members that share a catalytic PARP domain. PARPs constitute a family of cell signaling enzymes present in eukaryotes which catalyze poly(ADP-ribosylation) (PARsylation) of DNA-binding proteins and other substrate proteins. PARPs are also known as poly(ADP-ribose) synthases or poly(ADP-ribose) transferases (pARTs). Some PARPs also transfer single ADP-ribosyl-moieties. These enzymes, for example, play an important role in the immediate cellular response to DNA damage. In response to DNA damage induced by ionizing radiation, oxidative stress and DNA-binding anti-tumor drugs, PARPs add ADP-ribose units to the carboxylate groups of aspartic and glutamic residues of target proteins. This poly(ADP-ribosylation) is a post-translational modification process that triggers the inactivation of the acceptor protein through the attachment of a complex branched by a polymer of ADP-ribose units. ADP ribosylation is a post-translational protein modification process in which the ADP-ribose moiety is transferred from NAD onto specific amino acid side chains of target proteins (Schreiber et al., 2006, *Nature Reviews Cell Biology*, 7: 517-528).

PARP family proteins are promising therapeutic targets. PARP1 and PARP2 play a role in DNA damage responses and PARP inhibitors sensitize cancer cells for drug and radiation therapies. In addition, PARP1 has been linked to other diseases including inflammation, neuronal cell death and ischemia. Tankyrases (TNKS1 and TNKS2), which share high sequence similarity with PARP1, are also emerging therapeutic targets. Tankyrases were initially known as regulators of telomerase activity and are involved in DNA damage responses and Wnt signaling (Wahlbert et al., 2012, *Nat. Biotechnol.*, 30(3): 283-288).

The tankyrase protein family consists of tankyrase 1 (TNKS1) and tankyrase 2 (TNKS2) which share 85% amino acid identity. Biological functions of both tankyrase 1 and tankyrase 2 were studied in genetically engineered mice lacking mouse tankyrase 1 and/or tankyrase 2. Tankyrase 2-deficient mice developed normally and showed no detectable change in telomere length, but did show a significant decrease in total body weight that might reflect a role of tankyrase 2 in glucose or fat metabolism. No defects in telomere length maintenance were detected in tankyrase 1-deficient mice. However, in double-knockout mice lacking both tankyrase 1 and tankyrase 2 embryonic lethality was observed on embryonic day 10 (Chiang et al., 2008, *PLoS One*, 3(7): e2639).

A key feature of the Wnt/β-catenin pathway is the regulated proteolysis of the downstream effector β-catenin by the β-catenin destruction complex. The principal constituents of a β-catenin destruction complex are adenomatous polyposis coli (APC), axin and GSK3α/β. In the absence of Wnt pathway activation, cytosolic β-catenin is constitutively phosphorylated and targeted for degradation. Upon Wnt stimulation, a β-catenin destruction complex is dissociated, which leads to accumulation of β-catenin in the nucleus and transcription of Wnt pathway responsive genes.

It has been recently found that, in the Wnt/β-catenin pathway, a tankyrase inhibitor selectively inhibits the transcription mediated by β-catenin by promoting β-catenin degradation through stabilization of axin (Huang et al., 2009, *Nature*, 461(7264): 614-620).

Inappropriate activation of the pathway, mediated by overexpression of Wnt proteins or mutations affecting the components of the β-catenin destruction complex, thus leading to stabilization of β-catenin, has been observed in many cancers, for example, colon cancer, gastric cancer, hepatocellular carcinoma, breast cancer, medulloblastoma, melanoma, non-small cell lung cancer, pancreatic adenocarcinoma and prostate cancer (Waaler et al., 2012, *Cancer Res.*, 72(11): 2822-2832). Notably, truncating mutations of a tumor suppressor APC are the most prevalent genetic alterations in colorectal carcinomas (Miyaki et al., 1994, *Cancer Res.*, 54: 3011-3020). In addition, Axin1 and Axin2 mutations have been identified in patients with hepatocarcinomas and colorectal carcinomas (Taniguchi et al., 2002, *Oncogene*, 21: 4863-4871; Liu et al., 2000, *Nat. Genet.*, 26: 146-147). These somatic mutations result in Wnt-independent stabilization of β-catenin and constitutive activation of 3-catenin-mediated transcription. Furthermore, deregulated Wnt pathway activity has also been implicated in many other non-cancer diseases including osteoporosis, osteoarthritis, polycystic kidney disease, pulmonary fibrosis, diabetes, schizophrenia, vascular diseases, cardiac diseases, non-oncogenic proliferative diseases, neurodegenerative diseases such as Alzheimer's disease, etc.

Therapeutics which are directed to and can correct dysregulation of the Wnt signaling pathway have been implicated in conditions such as bone density defects, coronary disease, late-onset Alzheimer's disease, familial exudative vitreoretinopathy, retinal angiogenesis, tetraamelia, Muellerian-duct regression and virilization, Serkal syndrome, type 2 diabetes, Fuhrmann syndrome, skeletal dysplasia, focal dermal hypoplasia and neural tube defects. Although the introduction has focused on the relevance of Wnt signaling in cancer, the Wnt signaling pathway is of fundamental importance in a broad range of human diseases, not necessarily being limited to the examples provided above for illustrative purposes.

Meanwhile, it has recently been reported that intracellular axin levels are influenced by poly(ADP-ribose) polymerase family members tankyrase-1 and tankyrase-2 (also known as PARP5a and PARP5b) (*Nature Chemical Biology*, 2009, 5: 100; *Nature*, 2009, 461: 614). The tankyrase enzymes are able to poly-ADP ribosylate (PARsylate) axin, which marks this protein for subsequent ubiquitination and proteasomal degradation. Thus, it would be expected that in the presence of an inhibitor of tankyrase catalytic activity, the axin protein concentration would be increased, resulting in higher concentration of the destruction complex, decreased concentration of unphosphorylated intracellular β-catenin and decreased Wnt signaling. An inhibitor of tankyrase-1 and -2 would also be expected to have an effect on other biological functions of tankyrase proteins (e.g., chromosome end (telomere) protection, insulin responsiveness and spindle assembly during mitosis) (Chang et al., 2005, *Biochem. J.*, 391: 177-184; Chi et al., 2000, *J. Biol. Chem.*, 275: 38437-38444; Bae et al., 2003, *J. Biol. Chem.*, 278: 5195-5204).

DISCLOSURE OF INVENTION

Technical Problem

There are consistent needs for novel therapeutic agents that can be used for cancers and hyperproliferative conditions. Therefore, the inventors of the present invention have researched to design and develop novel pharmaceutical compounds that can inhibit or modulate the activity of tankyrase enzymes which are members of PARP family and regulate Wnt activity. As a result, they have found that the newly designed and synthesized triazolopyrimidinone or triazolopyridinone derivatives represented by Chemical Formula 1 can inhibit or regulate tankyrase activity and have completed the present invention:

[Chemical Formula 1]

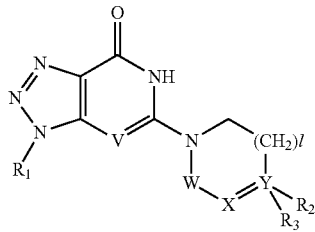

Solution to Problem

In an aspect, the present invention provides a compound represented by Chemical Formula 1, a tautomer thereof, a stereoisomer thereof and their mixture, or a pharmaceutically acceptable salt thereof:

[Chemical Formula 1]

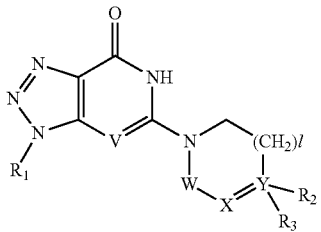

wherein
V is N or CH;
$R_1$ is hydrogen, $C_{1-6}$ alkyl, $C_{1-6}$ hydroxyalkyl, or $C_{1-6}$ dihydroxyalkyl;
each of W and X is independently $CHR_4$ or CO;
Y is N or C;
═ ═ ═ is a single bond or a double bond, determined by X and Y;
l is 0, 1 or 2;
$R_2$ is none, hydrogen, hydroxyl, cyano or $C_{1-6}$ alkyl;
$R_3$ is

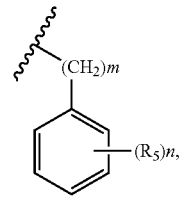

heteroary, heteroaryl-$C_{1-3}$ alkyl, heterocyclyl, or heterocyclyl $C_{1-3}$ alkyl;
$R_4$ is none, hydrogen, hydroxyl, $C_{1-6}$ alkyl or amine;
m is 0, 1, 2 or 3;
n is 0, 1, 2, 3, 4 or 5;
each of $R_5$ is independently halo, $C_{1-6}$ alkyl, $C_{2-6}$ alkenyl, $C_{1-6}$ alkoxy, $C_{1-3}$ alkoxy-$C_{1-3}$ alkyl, $C_{1-6}$ hydroxyalkyl, $C_{1-6}$ dihydroxyalkyl, $C_{1-6}$ haloalkyl unsubstituted or optionally substituted with hydroxy, $C_{3-7}$ cycloalkyl, $C_{1-6}$ alkyloxo, cyano, nitro, carboxy, $C_{1-6}$ alkoxycarbonyl or —Z—$(CH_2)_p$—$R_6$;
p is 0, 1, 2, 3, 4, 5 or 6;
Z is —O—, —S(O)$_q$—, —$NR_7$—, —$CONR_7$—, —$CHR_7$— or none;
q is 0, 1 or 2;
$R_6$ is hydrogen, cyano, hydroxyl, azido, $C_{1-6}$ alkoxy, $C_{1-3}$ alkoxy, $C_{1-3}$ alkyl, $C_{5-10}$ aryl, carboxy, $C_{1-6}$ dihydroxyalkyl, $C_{1-6}$ alkyl, $C_{1-6}$ haloalkyl unsubstituted or optionally substituted with hydroxy, $C_{3-6}$ cycloalkyl, heterocyclyl, heteroaryl, —S(O)$_r$—$R_8$, —O—(C═O)—$R_8$, —(C═O)—$R_8$, —$OR_8$, —$COOR_8$, —$NR_9R_{10}$ or —(C═O)$NR_9R_{10}$;
r is 0, 1 or 2;
$R_7$ is hydrogen, $C_{1-6}$ alkyl, $C_{3-6}$ cycloalkyl, $C_{1-3}$ alkyl-$C_{3-6}$ cycloalkyl or $C_{1-3}$ alkoxy-$C_{1-3}$ alkyl;
$R_8$ is hydrogen, $C_{1-6}$ alkyl, $C_{1-6}$ alkoxy, amino, $C_{1-6}$ alkylamino, $C_{1-6}$ aminoalkyl, heterocyclyl, $C_{3-6}$ cycloalkyl, $C_{1-3}$ alkyl-$C_{3-6}$ cycloalkyl, $C_{1-6}$ alkyloxo or $C_{1-3}$ alkoxy-$C_{1-3}$ alkyl;
each of $R_9$ and $R_{10}$ is independently hydrogen, $C_{1-6}$ alkyl, $C_{1-6}$ alkoxy, $C_{3-6}$ cycloalkyl, $C_{1-3}$ alkyl-$C_{3-6}$ cycloalkyl, $C_{1-3}$ alkoxy-$C_{1-3}$ alkyl or —(SO$_2$)—$C_{1-3}$ alkyl;
each of the heteroaryls may be a 5- to 10-membered single or fused ring containing one or more heteroatoms selected from the group consisting of N, O, S and a combination thereof, and each of the heterocycles may be a 3- to 10-membered single or fused ring containing one or more heteroatoms selected from the group consisting of N, O, S and a combination thereof;
each of the cycloalkyls and heterocyclyls may optionally be substituted with one to three substituents selected from the group consisting of $C_{1-6}$ alkyl, hydroxyl, oxo, $C_{1-6}$ hydroxyalkyl, halo, cyano, nitro, $C_{1-6}$ haloalkyl, $C_{1-6}$ alkoxy, formyl, $C_{1-6}$ alkylformyl, carboxy, $C_{1-6}$ alkylcarboxy, amino, $C_{1-6}$ alkylamino, di($C_{1-6}$ alkyl)amino, carbamoyl, $C_{1-6}$ alkylcarbamoyl, di($C_{1-6}$ alkyl)carbamoyl and $C_{1-3}$ alkoxy-$C_{1-3}$ alkyl; and
each of the aryls and heteroaryls may optionally be substituted with one to three substituents selected from the group consisting of $C_{1-6}$ alkyl, $C_{1-6}$ alkoxy, $C_{1-3}$ alkoxy-$C_{1-3}$ alkyl, $C_{1-6}$ hydroxyalkyl, $C_{1-6}$ haloalkyl, halo, cyano, pyrazinyl, hydroxy, oxo, nitro, formyl, $C_{1-6}$ alkylformyl, carboxy, $C_{1-6}$ alkylcarboxy, amino, $C_{1-6}$ alkylamino, di($C_{1-6}$ alkyl) amino, carbamoyl, $C_{1-6}$ alkylcarbamoyl, di($C_{1-6}$ alkyl)carbamoyl and $C_{1-6}$ alkylsulfonyl.

Preferably, in Chemical Formula 1,
V is N or CH;
$R_1$ is hydrogen, $C_{1-6}$ alkyl, $C_{1-6}$ hydroxyalkyl, or $C_{1-6}$ dihydroxyalkyl;
each of W and X is independently CH or $CH_2$;
Y is N or C;
⚏ is a single bond or a double bond; and
l is 0, 1 or 2.

Preferably, in Chemical Formula 1,
V is N or CH;
$R_1$ is hydrogen or $C_{1-6}$ alkyl;
each of W and X is independently CH or $CH_2$;
Y is N or C;
⚏ is a single bond or a double bond;
l is 0, 1 or 2;
$R_2$ is none, hydrogen or hydroxyl;
$R_3$ is

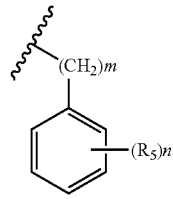

or heteroaryl;
$R_4$ is none or hydrogen;
m is 0;
n is 1, 2 or 3;
each of $R_5$ is independently halo, $C_{2-6}$ alkenyl, $C_{1-6}$ alkoxy, $C_{1-3}$ alkoxy-$C_{1-3}$ alkyl, $C_{1-6}$ hydroxyalkyl, $C_{1-6}$ dihydroxyalkyl or —Z—$(CH_2)_p$—$R_6$;
p is 0, 1, 2, 3 or 5;
Z is —O—, —$NR_7$— or none;
$R_6$ is cyano, hydroxyl, azido, $C_{1-6}$ alkoxy, $C_{1-3}$ alkoxy-$C_{1-3}$ alkyl, $C_{5-10}$ aryl, carboxy, $C_{1-6}$ dihydroxyalkyl, $C_{1-6}$ haloalkyl unsubstituted or optionally substituted with hydroxy, heterocyclyl, heteroaryl, —S(O)$_r$—$R_8$, —O—(C=O)—$R_8$, —(C=O)—$R_8$, —$NR_9R_{10}$ or —(C=O)$NR_9R_{10}$;
r is 2;
$R_7$ is hydrogen;
$R_8$ is hydrogen, $C_{1-6}$ alkyl, $C_{1-6}$ alkoxy, amino, $C_{1-6}$ alkylamino, $C_{1-6}$ aminoalkyl or heterocyclyl;
each of $R_9$ and $R_{10}$ is independently hydrogen, $C_{1-6}$ alkyl, $C_{1-3}$ alkoxy-$C_{1-3}$ alkyl or —(SO$_2$)—$C_{1-3}$ alkyl;
each of the heteroaryls may be a 5- to 10-membered single or fused ring containing one or more heteroatoms selected from the group consisting of N, O, S and a combination thereof, and each of the heterocycles may be a 3- to 10-membered single or fused ring containing one or more heteroatoms selected from the group consisting of N, O, S and a combination thereof;
each of the heterocyclyls may optionally be substituted with one to three substituents selected from the group consisting of $C_{1-6}$ alkyl, hydroxyl, amino, oxo, $C_{1-6}$ hydroxyalkyl and halo; and
each of the heteroaryls may optionally be substituted with one to three $C_{1-6}$ alkyl.

Preferably, in Chemical Formula 1,
V is N or CH;
$R_1$ is hydrogen or methyl;
each of W and X is independently CH or $CH_2$;
Y is N or C;
⚏ is a single bond or a double bond;
l is 1 or 2;
$R_2$ is none, hydrogen or hydroxyl;
$R_3$ is

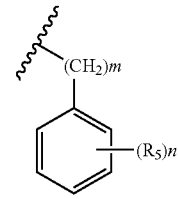

or heteroaryl;
$R_4$ is none or hydrogen;
m is 0;
n is 1, 2 or 3;
each of $R_5$ is independently fluoro, vinyl, isopropoxy, methoxyethyl, methoxypropyl, hydroxyethyl, 1,2-dihydroxyethyl, 2,3-dihydroxypropyl or —Z—$(CH_2)_p$—$R_6$;
p is 0, 1, 2, 3 or 5;
Z is —O—, —$NR_7$— or none;
$R_6$ is cyano, hydroxyl, azido, methoxy, ethoxy, methoxyethyl, $C_{5-10}$ aryl, carboxy, 1,2-dihydroxyethyl, 1-chloro-3-hydroxyisopropyl, perfluoromethyl, heterocyclyl, heteroaryl, —S(O)$_r$—$R_8$, —O—(C=O)—$R_8$, —(C=O)—$R_8$, —$NR_9R_{10}$ or —(C=O)$NR_9R_{10}$;
r is 2;
$R_7$ is hydrogen;
$R_8$ is hydrogen, methyl, amino, methylamino, or aminoethyl;
each of $R_9$ and $R_{10}$ is independently hydrogen, methyl, ethyl or methoxyethyl;
each of the heteroaryls may be a 5- to 10-membered single or fused ring containing one or more heteroatoms selected from the group consisting of N, O, S and a combination thereof, and each of the heterocycles may be a 3- to 10-membered single or fused ring containing one or more heteroatoms selected from the group consisting of N, O, S and a combination thereof;
each of the heterocyclyls may optionally be substituted with one to three substituents selected from the group consisting of methyl, fluoro, hydroxyl, amino and oxo; and
each of the heteroaryls may optionally be substituted with one to three methyls.

Preferably, in Chemical Formula 1,
each of the aryls is phenyl or naphthyl;
each of the heteroaryls may be selected from the group consisting of tetrazolyl, imidazolyl, pyridinyl, pyridazinyl, pyrimidyl, triazinyl, pyrrolyl, pyrazolyl, triazolyl, pyrazinyl, furyl, thienyl, isoxazolyl, thiazolyl, isothiazolyl, thiadiazolyl, furazanyl, oxazolyl, indolyl, isoindolyl, indazolyl, quinolinyl, isoquinolinyl, benzothiazolyl, benzoxazolyl, benzofuranyl, benzoimidazolyl, benzotriazolyl and azaindolyl; and
each of the heterocyclyls may be selected from the group consisting of tetrahydropyranyl, tetrahydrofuranyl, dihydrofuranyl, dihydropyranyl, dioxanyl, dithianyl, dioxolanyl, imidazolidinyl, imidazolinyl, pyrrolinyl, oxetanyl, pyrrolidinyl, piperidinyl, piperazinyl, morpholinyl, thiomorpholinyl, dioxothiomorpholinyl, dioxotetrahydrothiophenyl, dioxothiolanyl, oxopiperidinyl, oxopyrrolidinyl and oxooxazolidinyl.

Preferably, in Chemical Formula 1,
each of the aryls is phenyl;
each of the heteroaryls is tetrazolyl or imidazolyl; and
each of the heterocyclyls is tetrahydrofuranyl, oxetanyl, pyrrolidinyl, piperidinyl, piperazinyl or morpholinyl.

Preferably, in Chemical Formula 1,
each of the heterocyclyls is tetrahydrofuranyl, oxetanyl, pyrrolidinyl, piperidinyl, piperazinyl, morpholinyl, 4-methylpiperazinyl, 4-methyl-2-oxopiperazinyl, 3-hydroxypyrrolidinyl, 2-hydroxymethylpyrrolidinyl, N-methylpyrrolidinyl, 4-hydroxypiperidinyl, 4-hydroxy-4-methylpiperidinyl, 4-aminopiperidinyl, 2-oxopiperidinyl, 2,6-dimethylpiperidinyl or 4,4-difluoropiperidinyl.

More preferably, the compound may be
1) 5-(4-(2-fluorophenyl)piperazin-1-yl)-3-methyl-3H-[1,2,3]triazolo[4,5-d]pyrimidin-7(6H)-one,
2) 5-(4-(2,6-difluoro-4-(2-methoxyethoxy)phenyl)piperazin-1-yl)-3-methyl-3H-[1,2,3]triazolo[4,5-d]pyrimidin-7(6H)-one,
3) 5-(4-(4-(benzyloxy)-2,6-difluorophenyl)piperazin-1-yl)-3-methyl-3H-[1,2,3]triazolo[4, 5-d]pyrimidin-7(6H)-one,
4) 5-(4-(2,6-difluoro-4-(2-morpholinoethoxy)phenyl)piperazin-1-yl)-3-methyl-3H-[1,2,3]triazolo[4,5-d]pyrimidin-7(6H)-one,
5) 5-(4-(2,6-difluoro-4-(2-(piperidin-1-yl)ethoxy)phenyl)piperazin-1-yl)-3-methyl-3H-[1,2,3]triazolo[4,5-d]pyrimidin-7(6H)-one,
6) 5-(4-(4-(2-(dimethylamino)ethoxy)-2,6-difluorophenyl)piperazin-1-yl)-3-methyl-3H-[1,2,3]triazolo[4,5-d]pyrimidin-7(6H)-one,
7) 5-(4-(2,6-difluoro-4-(2-hydroxyethoxy)phenyl)piperazin-1-yl)-3-methyl-3H-[1,2,3]triazolo[4,5-d]pyrimidin-7(6H)-one,
8) 2-(3,5-difluoro-4-(4-(3-methyl-7-oxo-6,7-dihydro-3H-[1,2,3]triazolo[4,5-d]pyrimidin-5-yl)piperazin-1-yl)phenoxy)ethyl acetate,
9) 5-(4-(2,6-difluoro-4-isopropoxyphenyl)piperazin-1-yl)-3-methyl-3H-[1,2,3]triazolo[4,5-d]pyrimidin-7(6H)-one,
10) (R)-2-(3,5-difluoro-4-(4-(3-methyl-7-oxo-6,7-dihydro-3H-[1,2,3]triazolo[4,5-d]pyrimidin-5-yl)piperazin-1-yl)phenoxy)ethoxy)-1-oxopropan-2-aminium chloride,
11) (S)-2-(3,5-difluoro-4-(4-(3-methyl-7-oxo-6,7-dihydro-3H-[1,2,3]triazolo[4,5-d]pyrimidin-5-yl)piperazin-1-yl)phenoxy)ethoxy)-1-oxopropan-2-aminium chloride,
12) 5-(4-(4-(2,3-dihydroxypropoxy)-2,6-difluorophenyl)piperazin-1-yl)-3-methyl-3H-[1,2,3]triazolo[4,5-d]pyrimidin-7(6H)-one,
13) 5-(4-(2,6-difluoro-4-(morpholinomethyl)phenyl)piperazin-1-yl)-3-methyl-3H-[1,2,3]triazolo[4,5-d]pyrimidin-7(6H)-one,
14) 5-(4-(2,6-difluoro-4-((4-methylpiperazin-1-yl)methyl)phenyl)piperazin-1-yl)-3-methyl-3H-[1,2,3]triazolo[4,5-d]pyrimidin-7(6H)-one,
15) 5-(4-(2,6-difluoro-4-(oxetan-3-yloxy)phenyl)piperazin-1-yl)-3-methyl-3H-[1,2,3]triazolo[4,5-d]pyrimidin-7(6H)-one,
16) 5-(4-(4-(1-chloro-3-hydroxypropan-2-yloxy)-2,6-difluorophenyl)piperazin-1-yl)-3-methyl-3H-[1,2,3]triazolo[4,5-d]pyrimidin-7(6H)-one,
17) 5-(4-(2,6-difluoro-4-(1-hydroxyethyl)phenyl)piperazin-1-yl)-3-methyl-3H-[1,2,3]triazolo[4,5-d]pyrimidin-7(6H)-one,
18) 5-(4-(2,6-difluoro-4-(1-methoxyethyl)phenyl)piperazin-1-yl)-3-methyl-3H-[1,2,3]triazo[4,5-d]pyrimidin-7(6H)-one,
19) 6-(3,5-difluoro-4-(4-(3-methyl-7-oxo-6,7-dihydro-3H-[1,2,3]triazo[4,5-d]pyrimidin-5-yl)piperazin-1-yl)phenoxy)hexanoic acid,
20) 5-(4-(2,6-difluoro-4-(((2-methoxyethyl)(methyl)amino)methyl)phenyl)piperazin-1-yl)-3-methyl-3H-[1,2,3]triazolo[4,5-d]pyrimidin-7(6H)-one,
21) 5-(4-(2,6-difluorophenyl)piperazin-1-yl)-3-methyl-3H-[1,2,3]triazolo[4,5-d]pyrimidin-7(6H)-one,
22) 3-methyl-5-(4-(2,4,6-trifluorophenyl)piperazin-1-yl)-3H-[1,2,3]triazolo[4,5-d]pyrimidin-7(6H)-one,
23) 5-(4-(4-(1,2-dihydroxyethyl)-2,6-difluorophenyl)piperazin-1-yl)-3-methyl-3H-[1,2,3]triazolo[4,5-d]pyrimidin-7(6H)-one,
24) 5-(4-(4-(2,3-dihydroxypropyl)-2,6-difluorophenyl)piperazin-1-yl)-3-methyl-3H-[1,2,3]triazolo[4,5-d]pyrimidin-7(6H)-one,
25) 5-(4-(2,6-difluoro-4-(2-methoxyethoxy)phenyl)-4-hydroxypiperidin-1-yl)-3-methyl-3H-[1,2,3]triazolo[4,5-d]pyrimidin-7(6H)-one,
26) 5-(4-(1H-tetrazol-5-yl)piperidin-1-yl)-3-methyl-3H-[1,2,3]triazolo[4,5-d]pyrimidin-7(6H)-one,
27) 5-(4-(2,6-difluoro-4-(2-methoxyethylamino)phenyl)piperazin-1-yl)-3-methyl-3H-[1,2, 3]triazolo[4,5-d]pyrimidin-7(6H)-one,
28) 5-(4-(2,6-difluoro-4-vinylphenyl)piperazin-1-yl)-3-methyl-3H-[1,2,3]triazolo[4,5-d]pyrimidin-7(6H)-one,
29) 3-methyl-5-(4-(1-methyl-1H-tetrazol-5-yl)piperidin-1-yl)-3H-[1,2,3]triazolo[4,5-d]pyrimidin-7(6H)-one,
30) 3-methyl-5-(4-(2-methyl-2H-tetrazol-5-yl)piperidin-1-yl)-3H-[1,2,3]triazolo[4,5-d]pyrimidin-7(6H)-one,
31) 5-(4-(2,6-difluoro-4-(2-(pyrrolidin-1-yl)ethoxy)phenyl)piperazin-1-yl)-3-methyl-3H-[1,2,3]triazolo[4,5-d]pyrimidin-7(6H)-one, 32) 5-(4-(2,6-difluoro-4-(2-(4-methylpiperazin-1-yl)ethoxy)phenyl) piperazin-1-yl)-3-methyl-3H-[1,2,3]triazolo[4,5-d]pyrimidin-7(6H)-one,
33) 5-(4-(2,6-difluoro-4-(3-(piperidin-1-yl)propoxy)phenyl) piperazin-1-yl)-3-methyl-3H-[1,2,3]triazolo[4,5-d]pyrimidin-7(6H)-one,
34) 5-(4-(4-(bis(2-methoxyethyl)amino)-2,6-difluorophenyl) piperazin-1-yl)-3-methyl-3H-[1,2,3]triazolo[4,5-d]pyrimidin-7(6H)-one,
35) 5-(4-(2,6-difluoro-4-(2-oxo-2-(piperidin-1-yl)ethoxy)phenyl) piperazin-1-yl)-3-methyl-3H-[1,2,3]triazolo[4,5-d]pyrimidin-7(6H)-one,
36) 5-(4-(2,6-difluoro-4-(2-oxo-2-(pyrrolidin-1-yl)ethoxy) phenyl) piperazin-1-yl)-3-methyl-3H-[1,2,3]triazolo[4,5-d]pyrimidin-7(6H)-one,
37) 5-(4-(4-(2-aminoethoxy)-2,6-difluorophenyl)piperazin-1-yl)-3-methyl-3H-[1,2,3]triazolo[4,5-d]pyrimidin-7(6H)-one,
38) 5-(4-(2,6-difluoro-4-(2-(4-methyl-2-oxopiperazin-1-yl)ethoxy)phenyl)piperazin-1-yl)-3-methyl-3H-[1,2,3]triazolo[4,5-d]pyrimidin-7(6H)-one,
39) 5-(4-(4-(2-(4-aminopiperidin-1-yl)ethoxy)-2,6-difluoro phenyl)piperazin-1-yl)-3-methyl-3H-[1,2,3]triazolo[4,5-d]pyrimidin-7(6H)-one,
40) 5-(4-(2,6-difluoro-4-(3-methoxypropyl)phenyl)piperazin-1-yl)-3-methyl-3H-[1,2,3]triazolo[4,5-d]pyrimidin-7(6H)-one,
41) 5-(4-(2,6-difluoro-4-(2-(3-hydroxypyrrolidin-1-yl)ethoxy)phenyl)piperazin-1-yl)-3-methyl-3H-[1,2,3]triazolo[4,5-d]pyrimidin-7(6H)-one,
42) 5-(4-(2,6-difluoro-4-(2-(4-hydroxypiperidin-1-yl)ethoxy)phenyl)piperazin-1-yl)-3-methyl-3H-[1,2,3]triazolo[4,5-d]pyrimidin-7(6H)-one,
43) 5-(4-(2,6-difluoro-4-(2-(4-hydroxy-4-methylpiperidin-1-yl)ethoxy)phenyl)piperazin-1-yl)-3-methyl-3H-[1,2,3]triazolo[4,5-d]pyrimidin-7(6H)-one,
44) 5-(4-(2,6-difluoro-4-(2-methoxyethoxy)phenyl)-5,6-dihydropyridin-1(2H)-yl)-3-methyl-1-3H-[1,2,3]triazolo[4,5-d]pyrimidin-7(6H)-one,
45) 5-(4-(2,6-difluoro-4-(2-methoxyethoxy)phenyl)piperidin-1-yl)-3-methyl-3H-[1,2,3]triazolo[4,5-d]pyrimidin-7(6H)-one,
46) 5-(4-(2,6-difluoro-4-(2-(2-oxopiperidin-1-yl)ethoxy)phenyl)piperazin-1-yl)-3-methyl-3H-[1,2,3]triazolo[4,5-d]pyrimidin-7(6H)-one,
47) 5-(4-(4-(2-ethoxyethoxy)-2,6-difluorophenyl)piperazin-1-yl)-3-methyl-3H-[1,2,3]triazolo[4,5-d]pyrimidin-7(6H)-one,
48) 5-(4-(4-(2-(cis-2,6-dimethylpiperidin-1-yl)ethoxy)-2,6-difluorophenyl)piperazin-1-yl)-3-methyl-3H-[1,2,3]triazolo[4,5-d]pyrimidin-7(6H)-one,
49) 5-(4-(4-(2-(4,4-difluoropiperidin-1-yl)ethoxy)-2,6-difluorophenyl)piperazin-1-yl)-3-methyl-3H-[1,2,3]triazolo[4,5-d]pyrimidin-7(6H)-one,
50) 5-(4-(4-(2-(diethylamino)ethoxy)-2,6-difluorophenyl)piperazin-1-yl)-3-methyl-3H-[1,2,3]triazolo[4,5-d]pyrimidin-7(6H)-one,
51) 5-(4-(4-(2-(1H-imidazol-1-yl)ethoxy)-2,6-difluorophenyl) piperazin-1-yl)-3-methyl-3H-[1,2,3]triazolo[4,5-d]pyrimidin-7(6H)-one,
52) 5-(4-(2,6-difluoro-4-((tetrahydrofuran-2-yl)methoxy)phenyl)piperazin-1-yl)-3-methyl-3H-[1,2,3]triazolo[4,5-d]pyrimidin-7(6H)-one,
53) 6-(4-(2,6-difluoro-4-(2-methoxyethoxy)phenyl)piperazin-1-yl)-1-methyl-1H-[1,2,3]triazolo[4,5-c]pyridin-4(5H)-one,
54) 6-(4-(2,6-difluoro-4-(2-morpholinoethoxy)phenyl)piperazin-1-yl)-1-methyl-1H-[1,2,3]triazolo[4,5-c]pyridin-4 (5H)-one,
55) 6-(4-(2,6-difluoro-4-(2-(piperidin-1-yl)ethoxy)phenyl)piperazin-1-yl)-1-methyl-1H-[1,2,3]triazolo[4,5-c]pyridin-4 (5H)-one,
56) 6-(4-(4-(2-(dimethylamino)ethoxy)-2,6-difluorophenyl)piperazin-1-yl)-1-methyl-1H-[1,2,3]triazolo[4,5-c]pyridin-4 (5H)-one,
57) 6-(4-(2,6-difluoro-4-(2-hydroxyethoxy)phenyl)piperazin-1-yl)-1-methyl-1H-[1,2,3]triazolo[4,5-c]pyridin-4(5H)-one,
58) (S)-2-(3,5-difluoro-4-(4-(1-methyl-4-oxo-4,5-dihydro-1H-[1,2,3]triazolo[4,5-c]pyridin-6-yl)piperazin-1-yl)phenoxy)ethyl2-aminopropanoate hydrochloride,
59) 6-(4-(4-(2,3-dihydroxypropoxy)-2,6-difluorophenyl)piperazin-1-yl)-1-methyl-1H-[1,2,3]triazolo[4,5-c]pyridin-4 (5H)-one,
60) 6-(4-(2,6-difluoro-4-(morpholinomethyl)phenyl)piperazin-1-yl)-1-methyl-1H-[1,2,3]triazolo[4,5-c]pyridin-4(5H)-one,
61) 6-(4-(2,6-difluoro-4-((4-methylpiperazin-1-yl)methyl) phenyl) piperazin-1-yl)-1-methyl-1H-[1,2,3]triazolo[4,5-c]pyridin-4(5H)-one,
62) 6-(4-(2,6-difluoro-4-(oxetan-3-yloxy)phenyl)piperazin-1-yl)-1-methyl-1H-[1,2,3]triazolo[4,5-c]pyridin-4(5H)-one,
63) 6-(4-(2,6-difluoro-4-(1-hydroxyethyl)phenyl)piperazin-1-yl)-1-methyl-1H-[1,2,3]triazolo[4,5-c]pyridin-4(5H)-one,
64) 6-(4-(2,6-difluoro-4-(1-methoxyethyl)phenyl)piperazin-1-yl)-1-methyl-1H-[1,2,3]triazolo[4,5-c]pyridin-4(5H)-one,
65) 6-(4-(2,6-difluoro-4-(((2-methoxyethyl)(methyl)amino) methyl)phenyl)piperazin-1-yl)-1-methyl-1H-[1,2,3]triazolo[4,5-c]pyridin-4(5H)-one,
66) 1-methyl-6-(4-(2-methyl-2H-tetrazol-5-yl)piperidin-1-yl)-1H-[1,2,3]triazolo[4,5-c]pyridin-4(5H)-one,
67) 6-(4-(2,6-difluoro-4-(2-(pyrrolidin-1-yl)ethoxy)phenyl)piperazin-1-yl)-1-methyl-1H-[1,2,3]triazolo[4,5-c]pyridin-4 (5H)-one,
68) 6-(4-(2,6-difluoro-4-(2-(4-methylpiperazin-1-yl)ethoxy) phenyl)piperazin-1-yl)-1-methyl-1H-[1,2,3]triazolo[4,5-c]pyridin-4(5H)-one, 69) 6-(4-(2,6-difluoro-4-(3-(piperidin-1-yl)propoxy)phenyl)piperazin-1-yl)-1-methyl-1H-[1,2,3]triazolo[4,5-c]pyridin-4(5H)-one,
70) 6-(4-(2,6-difluoro-4-(2-oxo-2-(pyrrolidin-1-yl)ethoxy)phenyl)piperazin-1-yl)-1-methyl-1H-[1,2,3]triazolo[4,5-c]pyridin-4(5H)-one,
71) 6-(4-(4-(2-aminoethoxy)-2,6-difluorophenyl)piperazin-1-yl)-1-methyl-1H-[1,2,3]triazolo[4,5-c]pyridin-4(5H)-one,
72) 6-(4-(4-(2-(4-aminopiperidin-1-yl)ethoxy)-2,6-difluorophenyl)piperazin-1-yl)-1-methyl-1H-[1,2,3]triazolo[4,5-c]pyridin-4(5H)-one, or
73) 5-(4-(2,6-difluoro-4-(2-methoxyethoxy)phenyl)piperazin-1-yl)-3H-[1,2,3]triazolo[4,5-d]pyrimidin-7(6H)-one.

For example, the compound of the present invention may be synthesized from 6-amino-2-thioxo-2,3-dihydropyrimidin-4(1H)-one or 4-amino-6-thioxo-5,6-dihydropyridin-2(1H)-one via a series of reactions. The following reaction scheme is presented as an exemplary preparation method of the compound of the present invention. However, the method for preparing the compound of the present invention is not limited thereto and a method known in the art may be employed with appropriate modification, if necessary.

First, through a series of reactions described below, 5-(methylsulfonyl)-3H-[1,2,3]triazolo[4,5-d]pyrimidin-7(6H)-one (7a); or 7-isopropoxy-5-(methylsulfonyl)-3H-[1,2,3]triazolo[4,5-d]pyrimidine (7b) may be synthesized as intermediates.

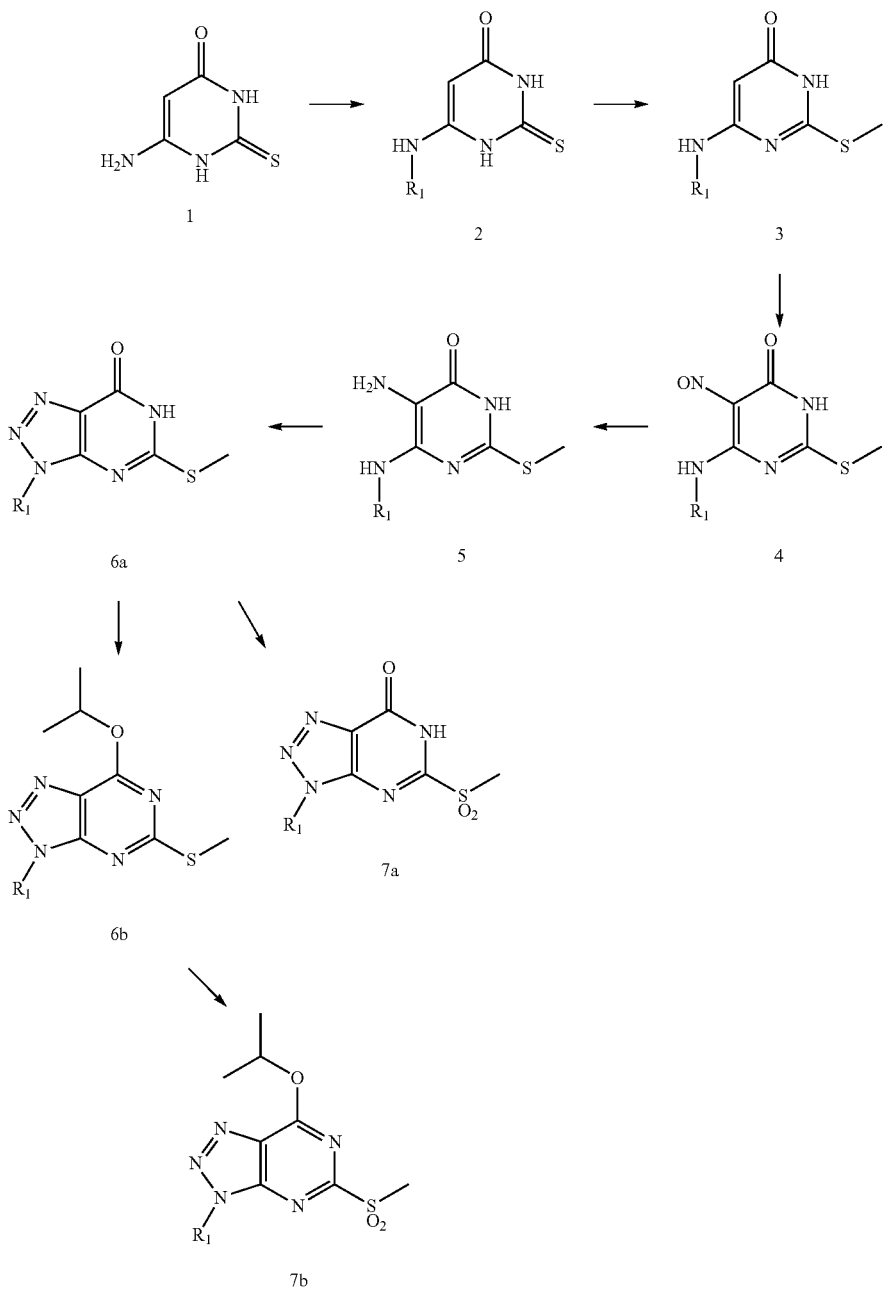

In the reaction scheme above, $R_1$ is as defined in Chemical Formula 1.

First, 6-amino-2-thioxo-2,3-dihydropyrimidin-4(1H)-one (1), a dihydropyrimidinone compound containing both an amino group and a thioxo group, reacts with an alkylammonium chloride in a N-methylformamide solvent to introduce a substituent $R_1$ to the amino group. Preferably, the reaction may be carried out for 2 h under reflux, and the reaction may be omitted when $R_1$ is hydrogen. The product (2) reacts with dimethyl sulfate in an aqueous solution in the presence of KOH to form a methylthio derivative (3) in which a methyl group is introduced to the thioxo group. Preferably, this reaction may be conducted at rt for 2 h. Subsequently, the methylthio derivative of the dihydropyrimidinone compound (3) reacts with sodium nitrite in acetic acid to introduce a nitroso group (4), and the introduced nitroso group is reduced to an amino group using ammonium sulfide (5). Preferably, this reaction may be carried out at 90° C. for 1 h. The resulting compound, including an amino group and another amino group substituted or unsubstituted with $R_1$, which are adjacent to each other, further reacts with sodium nitrite to induce cyclization between the adjacent amino groups. Preferably, this reaction may be conducted at rt in the presence of hydrochloric acid. The parent structure of the compound of the present invention, triazolopyrimidinone (6a), which has a fused form between a triazolo with one nitrogen unsubstituted or substituted with $R_1$ and a pyrimidinone, is oxidized, for example, with the oxidizing agent Oxone® in a mixture solvent of THF and water to convert the methylthio group to a methylsulfonyl group and an intermediate 7a is obtained. Alternatively, triazolopyrimidinone (6a) reacts with isopropyl iodide in DMF as a solvent in the presence of CsF to introduce an isopropyl group to a ketone group and a compound 6b is obtained. Subsequently, the compound reacts with meta-chloroperoxybenzoic acid (mCPBA) in methylene chloride as a solvent to convert the methylthio group to a methylsulfonyl group and an intermediate 7b is obtained.

After the intermediate (7a or 7b) which constitutes the parent structure of the compound of the present invention is synthesized as described above, a substituent replacing methylsulfonyl group is introduced by further carrying out one or more reaction(s) known in the art.

For example, when the substituent replacing methylsulfonyl group is an amine group, the triazolopyrimidinone derivative compound (8a) as the target compound of the present invention may be obtained from the intermediate compound (7a or 7b) by amination according to the following reaction scheme and, optionally, carrying out amination followed by deprotection if necessary.

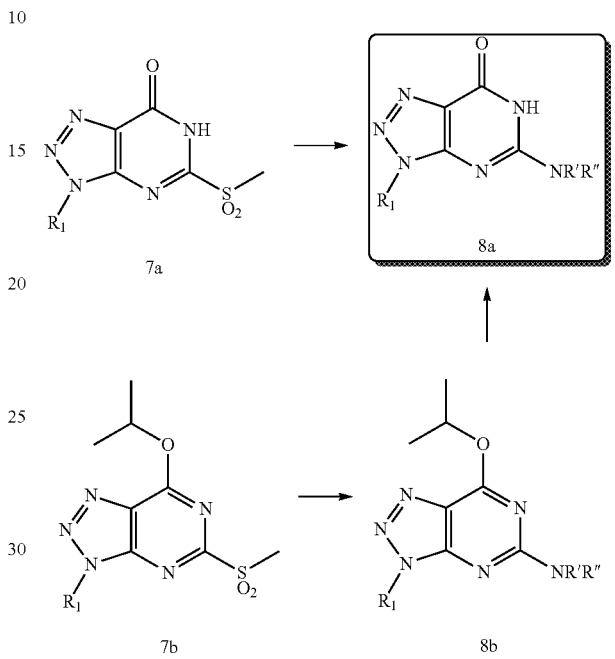

Preferably, the amination may be conducted by causing the intermediate to react with an amine compound containing a substituent suitable for the desired target compound, DIPEA, in an alcohol solvent (isopropanol or ethanol). Preferably, for a compound containing a lactam group, the reaction may be carried out at 150° C. for 0.5 h and, for a compound containing an isopropyl group as a protecting group, the reaction may be carried out for 2 h under reflux in a sealed container.

Preferably, the deprotection may be accomplished by removing the isopropyl group via reaction with AcOH containing concentrated hydrochloric acid.

Also, through a series of reactions described below, 4-(benzyloxy)-6-chloro-1-methyl-1H-[1,2,3]triazolo[4,5-c]pyridine (15) may be synthesized as an intermediate.

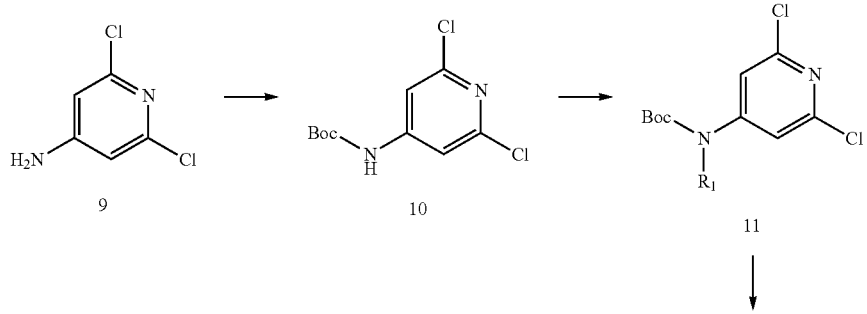

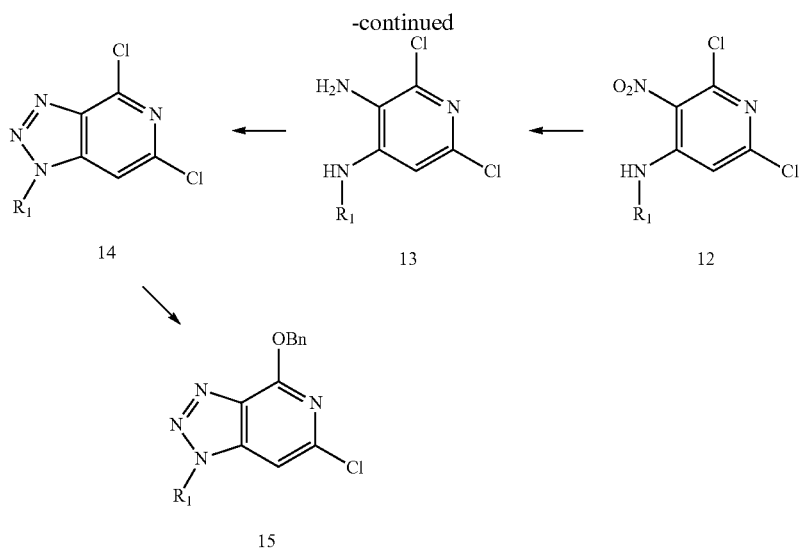

In the reaction scheme above, R$_1$ is as defined in Chemical Formula 1.

First, 4-amino-2,6-dichloropyridine (9) reacts with di-tert-butyl dicarbonate in the presence of 4-dimethylaminopyridine in THF to introduce a protecting group to the amino group. Preferably, the reaction may be carried out at 60° C. to 70° C. for 23 h. The product (10) reacts with NaH and methyliodide in a mixture of DMF/THF to form a pyridine derivative (11) in which a methyl group is introduced to the amino group. The reaction may be omitted when R$_1$ is hydrogen. Preferably, the reaction may be carried out at 0° C. to rt for 2 h. Then, a nitro group (12) can be introduced to the pyridine derivative (11) using sulfuric acid and nitric acid, and reduced into an amino group (13) by 5% Pt/C(S). Preferably, the reaction may be carried out at rt for 4 h. The resulting compound including one neighboring amino group and another amino group unsubstituted or substituted with R$_1$, further reacts with sodium nitrite to induce cyclization between the two neighboring amino groups. Preferably, the reaction may be carried out at 0° C. to rt in the presence of hydrochloric acid.

The dichloro derivative (14) reacts with NaH and benzyl alcohol in DMF solvent to introduce a benzyl group selectively to one of the chloro positions. Therefore, a part of a parent structure of the compound of the present invention, triazolopyridine (15) can be obtained as a fused ring of a triazole substituted with R$_1$ on one nitrogen atom and a pyridine substituted with a chloro group.

After the intermediate (15) which constitutes the parent structure of the compound of the present invention is synthesized as described above, a substituent replacing a chloro group is introduced by further carrying out one or more reaction(s) known in the art.

For example, when the substituent replacing a chloro group is an amine group, the triazolopyridinone derivative compound (17) as the target compound of the present invention may be obtained from the intermediate compound (15) by amination according to the following reaction scheme and, optionally, carrying out deprotection following the amination if necessary.

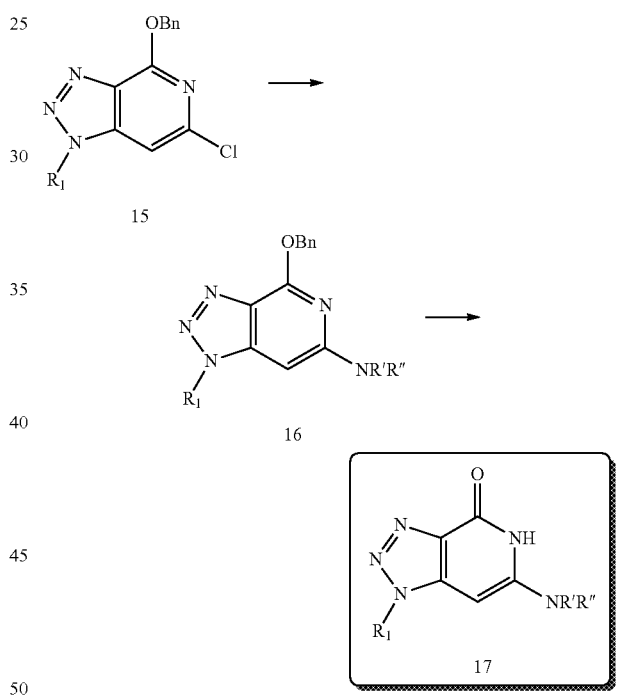

Preferably, the amination may be conducted via Buchwald-Hartwig amination of the intermediate to react with an amine compound containing a substituent suitable for the desired target compound, in dioxane or toluene solvent. Preferably, the reaction may be carried out at 110° C. for 12 h to 24 h.

Preferably, the deprotection may be accomplished by hydrogenation in methanol under 10% Pd/C catalyst to remove a benzyl group.

In another aspect, the present invention provides a pharmaceutical composition for treating or preventing a tankyrase-related disease, which contains the compound of the present invention, a tautomer thereof, a stereoisomer thereof and their mixture, or a pharmaceutically acceptable salt thereof as an active ingredient.

Preferably, the compound of the present invention, the tautomer thereof, the stereoisomer thereof and their mixture, or the pharmaceutically acceptable salt thereof may exhibit activity of inhibiting activities of tankyrase 1, tankyrase 2 or both. Preferably, a pharmaceutical composition comprising the compound of the present invention as an active ingredient may be usefully used for the prevention or treatment of a cancer, multiple sclerosis (MS), a cardiovascular disease, central nervous system injury and an inflammatory disease. The cancer may be selected from the group consisting of a cancer of head, neck, eyes, mouth, throat, esophagus, bronchus, larynx, pharynx, chest, bone, lungs, colon, rectum, stomach, prostate, bladder, uterine, cervix, breast, ovaries, testicles or other reproductive organs, skin, thyroid, blood, lymph nodes, kidneys, liver, pancreas, brain or central nervous system, a solid tumor, a blood-borne tumor, etc. Preferably, the tankyrase-related disease that can be prevented or treated using the pharmaceutical composition of the present invention may be colorectal cancer including colon cancer and rectal cancer, breast cancer, lung cancer or hematological malignancy, although it is not limited thereto.

The compound of the present invention may exist in the form of a pharmaceutically acceptable salt. An acid addition salt formed by a pharmaceutically acceptable free acid is useful as the salt. The term "pharmaceutically acceptable salt" used in the present invention refers to any organic or inorganic addition salt of the compound represented by Chemical Formula 1 which is at such a concentration that is relatively nontoxic to a patient and has a harmless effective action, and adverse side effects from the salt do not counteract benefits of the compound.

The acid addition salt may be prepared according to a commonly employed method, for example, by dissolving the compound in an excess amount of an aqueous acid solution and precipitating the salt using a water-miscible organic solvent, e.g., methanol, ethanol, acetone or acetonitrile. After heating the compound with an equimolar acid or alcohol (e.g., glycol monomethyl ether) in water, the mixture may be dried via evaporation, or the precipitated salt may be filtered through suction.

Here, a free acid may be an organic acid or an inorganic acid. As an inorganic acid, hydrochloric acid, phosphoric acid, sulfuric acid, nitric acid, stannic acid, etc., may be used and, as an organic acid, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic and, ascorbic acid, carbonic acid, vanillic acid, hydroiodic acid, etc. may be used, although it is not limited thereto.

Furthermore, a pharmaceutically acceptable metal salt may be prepared using a base. An alkali metal salt or an alkaline earth metal salt may be obtained, for example, by dissolving the compound in an excess amount of an alkali metal hydroxide or alkaline earth metal hydroxide solution, filtering an undissolved compound salt and then evaporating and drying the filtrate. Preferably, as the metal salt, sodium, potassium or calcium salt may be pharmaceutically suitable, although it is not limited thereto. Also, a corresponding silver salt may be obtained by reacting the alkali metal or alkaline earth metal salt with an appropriate silver salt (e.g., silver nitrate).

Unless specified otherwise, the pharmaceutically acceptable salt of the compound of the present invention includes a plausible acidic or basic salt of the compound of Chemical Formula 1. For example, the pharmaceutically acceptable salt includes sodium, calcium and potassium salts having a hydroxy. In addition, hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts having an amino group may be included as other pharmaceutically acceptable salts. They may be prepared by salt preparation methods known in the art.

The pharmaceutically acceptable salt of triazolopyrimidinone or triazolopyridinone derivative of the present invention may be any pharmaceutically acceptable salt of triazolopyrimidinone or triazolopyridinone derivatives which exhibit inhibitory activity against tankyrase 1 and/or tankyrase 2, which is equivalent to that of triazolopyrimidinone or triazolopyridinone derivative compounds, without limitation.

In the present invention, the term "prevention" refers to any act of inhibiting or retarding the onset, development and recurrence of tankyrase-related diseases by administering the composition of the present invention, and the term "treatment" refers to any act of ameliorating or improving symptoms of the diseases by administering the composition of the present invention.

Since the composition of the present invention can prevent or treat tankyrase-related disease by inhibiting the activity of tankyrase 1 and/or tankyrase 2 and thereby regulating cell death proliferation and/or metastasis, it can be usefully used to prevent or treat a disease induced by abnormal activity of tankyrase 1 and/or tankyrase 2.

Preferably, the pharmaceutical composition according to the present invention may contain 0.1 wt % to 75 wt %, more preferably 1 wt % to 50 wt %, of the compound represented by Chemical Formula 1, the tautomer thereof, the stereoisomer thereof and their mixture, or the pharmaceutically acceptable salt thereof as an active ingredient, based on the total weight of the composition.

The composition of the present invention may further contain a pharmaceutically acceptable carrier, diluent, or excipient, and may be prepared into various formulations including oral formulations such as powder, granule, tablet, capsule, suspension, emulsion, syrup, aerosol, etc., sterile injection solution, etc., according to commonly employed methods. It may be administered orally or via various routes including intravenous, intraperitoneal, subcutaneous, rectal and topical routes. Examples of the suitable carrier, excipient, or diluent that can be contained in the composition may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. In addition, the composition of the present invention may further contain a filler, an anti-aggregant, a lubricant, a wetting agent, a fragrance, an emulsifier, a preservative, etc.

Solid formulations for oral administration may include tablet, pill, powder, granule, capsule, etc. These solid formulations may be prepared by mixing at least one excipient, e.g., starch, calcium carbonate, sucrose, lactose, gelatin, etc., in the composition. In addition to a simple excipient, a lubricant such as magnesium stearate and talc may be used.

Liquid formulations for oral administration may be exemplified by suspension, solution for internal application, emulsion, syrup, etc. In addition to a commonly used simple diluent such as water and liquid paraffin, various excipients such as a wetting agent, a sweetener, an aromatic, a preservative, etc., may be included.

Formulations for parenteral administration may include sterilized aqueous solution, non-aqueous solution, suspension, emulsion, lyophilizate and suppository. For the non-aqueous solution or suspension, propylene glycol, polyethylene glycol, vegetable oil such as olive oil, injectable ester such as ethyl oleate, etc., may be used. As a base for the suppository, Witepsol, macrogol, Tween 61, cacao butter, laurin butter, glycerogelatin, etc., may be used. Meanwhile, injectable formulations may contain commonly used additives such as a solubilizer, an isotonizing agent, a suspending agent, an emulsifier, a stabilizer, a preservative, etc.

The composition of the present invention is administered in a pharmaceutically effective amount. In the present invention, the term "pharmaceutically effective amount" refers to an amount which is sufficient to treat a disease at a reasonable benefit/risk ratio applicable for medical treatment without causing side effects. The level of effective dosage may be determined based on the health condition of a patient, a kind of disease and severity thereof, drug activity, sensitivity to the drug, administration method, administration time, administration route, rate of excretion, treatment period, drugs used in combination or simultaneously and other factors well known in the medical field. The composition of the present invention may be administered as an independent therapeutic agent or in combination with other therapeutic agent(s) sequentially or simultaneously. Also, it may be administered in the form of a single dose or multidoses. It is important to administer an amount that can derive the maximum effects with the minimum amount with no side effects in consideration of all the above-described factors, which can be easily determined by those skilled in the art.

Specifically, the effective amount of the compound in the composition of the present invention may vary depending on the age, sex and body weight of a patient. In general, an amount of 1 mg to 100 mg, preferably 5 mg to 60 mg, per kg body weight may be administered once a day, once in two days or 1 to 3 times a day. However, since the administration dosage can be increased or decreased depending on the administration route, severity of disease, sex, body weight, and age, etc., it does not limit the scope of the present invention by any means.

The present invention also provides a method for preventing or treating a tankyrase-related disease of a subject, which includes administering the compound represented by Chemical Formula 1, the tautomer thereof, the stereoisomer thereof and their mixture, or the pharmaceutically acceptable salt thereof to the subject in need thereof.

In the present invention, the term "subject" refers to an animal in which a tankyrase-related disease has occurred or is likely to occur, including human, monkey, cow, horse, sheep, pig, chicken, turkey, quail, cat, dog, mouse, rat, rabbit or guinea pig. The disease may be effectively prevented or treated by administering the pharmaceutical composition of the present invention to the subject. The pharmaceutical composition of the present invention may be administered in combination with existing therapeutic agent.

In the present invention, the term "administration" refers to introduction of a desired substance to a patient in any appropriate way. The composition of the present invention may be administered via any general administration route as long as it can reach a target tissue. For example, the composition may be administered intraperitoneally, intravenously, intramuscularly, subcutaneously, intradermally, orally, topically, intranasally, intrapulmonarily or rectally, although it is not limited thereto. In addition, the pharmaceutical composition of the present invention may be administered by any apparatus that can deliver an active substance to a target cell. Preferred administration methods and formulations include intravenous injection, subcutaneous injection, intradermal injection, intramuscular injection, bolus injection, etc. The injection may be prepared using water-based solutions such as physiological saline, Ringer's solution, etc., or non-water-based solutions such as vegetable oils, higher fatty acid esters (e.g., ethyl oleate), or alcohols (e.g., ethanol, benzyl alcohol, propylene glycol, glycerin, etc.), and may contain a pharmaceutical excipient such as a stabilizer for preventing denaturation (e.g., ascorbic acid, sodium bisulfife, sodium pyrosulfite, BHA, tocopherol, EDTA, etc.), an emulsifier, a buffer for pH control, a preservative for inhibiting microbial growth (e.g., phenylmercuric nitrate, thimerosal, benzalkonium chloride, phenol, cresol, benzyl alcohol, etc.), etc.

In the present invention, the term "therapeutically effective amount" used in combination with an active ingredient refers to an amount of the triazolopyrimidinone or triazolopyridinone derivative compound, the tautomer thereof, the stereoisomer thereof and their mixture, or the pharmaceutically acceptable salt thereof which is effective in preventing or treating a target disease.

In addition to the triazolopyrimidinone or triazolopyridinone derivative compound, the tautomer thereof, the stereoisomer thereof and their mixture, or the pharmaceutically acceptable salt thereof as the active ingredient, the pharmaceutical composition of the present invention may further comprise a drug used and known for the prevention or treatment of a particular disease depending on a kind of a disease to be prevented or treated. For example, when used for prevention or treatment of a cancer, the composition may further contain, in addition to the triazolopyrimidinone or triazolopyridinone derivative compound, the tautomer thereof, the stereoisomer thereof and their mixture, or the pharmaceutically acceptable salt thereof as the active ingredient, a known anti-cancer agent. Also, other therapies may be used in combination to treat the disease, which include chemotherapy, radiation therapy, hormone therapy, bone marrow transplantation, stem cell replacement therapy, other biological therapies, immunotherapy, etc., although they are not limited thereto.

Examples of anti-cancer agents that can be contained in the pharmaceutical composition of the present invention include a DNA alkylating agent such as mechlorethamine, chlorambucil, phenylalanine, mustard, cyclophosphamide, ifosfamide, carmustine (BCNU), lomustine (CCNU), streptozotocin, busulfan, thiotepa, cisplatin and carboplatin; an anti-cancer antibiotic such as dactinomycin (actinomycin D), doxorubicin (Adriamycin), daunorubicin, idarubicin, mitoxantrone, plicamycin, mitomycin C and bleomycin; and a plant alkaloid such as vincristine, vinblastine, paclitaxel, docetaxel, etoposide, teniposide, topotecan and iridotecan, etc., although they are not limited thereto.

Advantageous Effects of Invention

Since a novel triazolopyrimidinone or triazolopyridinone derivative of the present invention can inhibit tankyrase 1 and/or tankyrase 2, it can be effectively used to treat or prevent a disease induced by overexpression or hyperactivation of tankyrases.

BEST MODE FOR CARRYING OUT THE INVENTION

Hereinafter, the constitution and effect of the present invention will be described in more detail through Examples. However, the following Examples are for illustrative purposes only and the scope of the present invention is not limited by the examples.

Preparation Example 1: 7-Isopropoxy-3-methyl-5-(methylsulfonyl)-3H-[1,2,3]triazolo[4,5-d]pyrimidine (I-7)

7-Isopropoxy-3-methyl-5-(methylsulfonyl)-3H-[1,2,3]triazolo[4,5-d]pyrimidine (I-7) was prepared as an intermediate for synthesis of triazolopyrimidinone derivatives based on the following reaction scheme.

1.1. 6-(Methylamino)-2-(methylthio)pyrimidin-4(3H)-one (I-2)

A mixture of 6-amino-thiouracil (10 g, 62 mmol) and methylamine HCl (5 g) in N-methylformamide (40 mL) was heated to reflux for 4 h. After the reaction was completed, the mixture was allowed to cool down to rt and stirred for 0.5 h. Then, water was added, and the precipitate was filtered, washed with water, and dried to afford the N-methyl compound I-1 (5.3 g) as a yellow solid. To a solution of the yellow solid I-1 (5.3 g) and KOH (4.18 g, 74.450 mmol) in water (100 mL) was added dropwise dimethyl sulfate (5.87

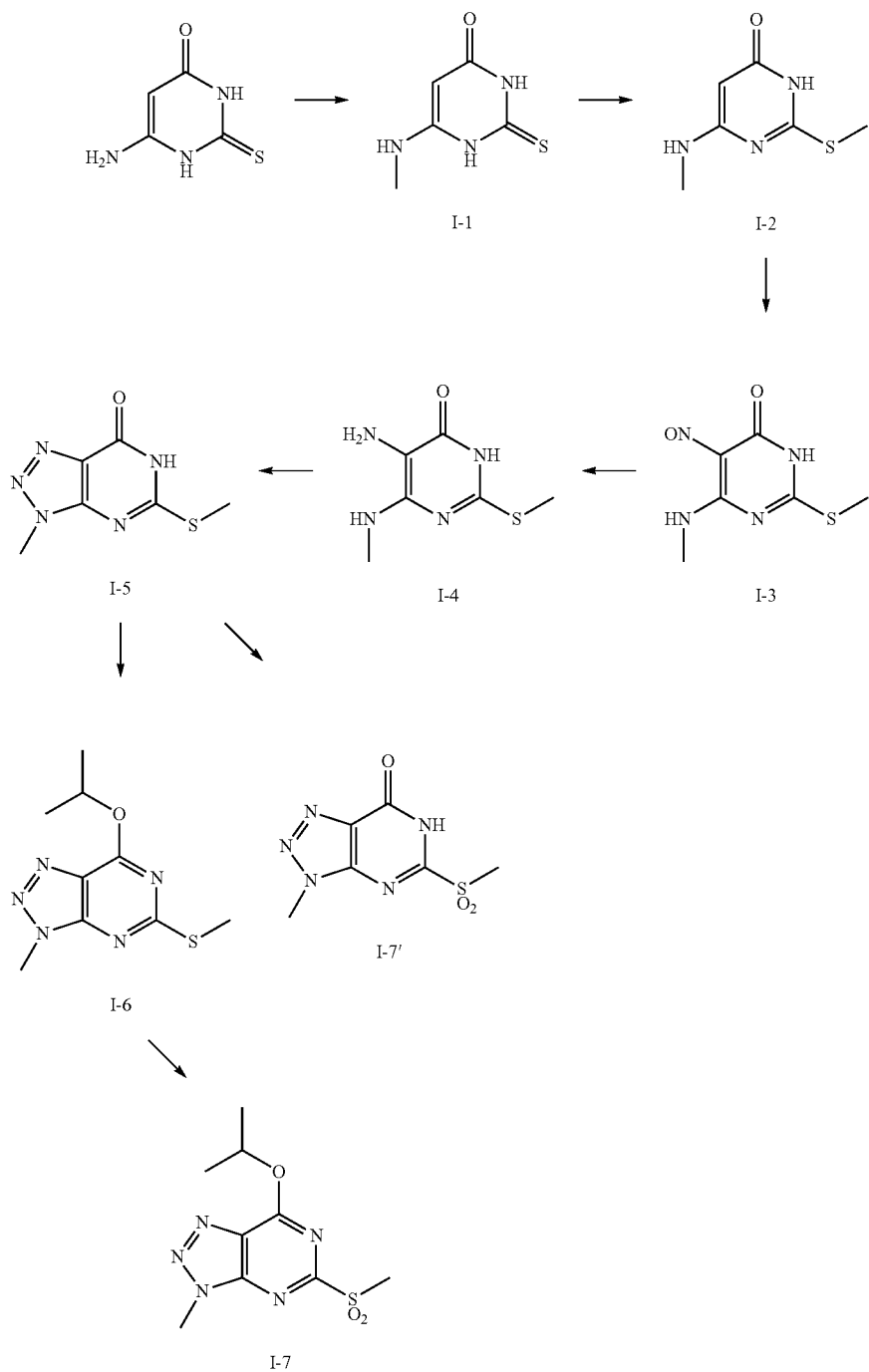

mL) at 0° C. over 1 h. After stirring at rt for 16 h, the precipitate was filtered, washed with water, and dried. The residue was purified by column chromatography to afford the desired product I-2 (5.3 g) as a yellow solid.

GC-MS (EI, m/z)=171 (M$^+$).

1.2. 6-(Methylamino)-2-(methylthio)-5-nitrosopyrimidin-4(3H)-one (I-3)

To a solution of the compound I-2 (5.3 g, 30.954 mmol) in a mixture of water (90 mL) and AcOH (9 mL) was added dropwise a solution of NaNO$_2$ (5.34 g, 77.385 mmol) in water (25 mL) at 0° C. over 2 h. After stirring at rt for 22 h, the precipitate was filtered, washed with water, and dried to afford the desired product I-3 (5.2 g) as a blue solid.

GC-MS (EI, m/z)=200 (M$^+$).

1.3. 3-Methyl-5-(methylthio)-3H-[1,2,3]triazolo[4,5-d]pyrimidin-7(6H)-one (I-5)

To a preheated (75° C. to 80° C.) 20% S(NH$_4$)$_2$ in water (110 mL) was added portionwise the compound I-3 (5.2 g, 25.971 mmol) over 1 h. The reaction mixture was heated to reflux for 1 h. The reaction mixture was allowed to cool down to rt, and the precipitate was filtered, washed with MeOH, and dried to afford the intermediate 1-4 as a yellow solid. To a solution of the intermediate 1-4 in 1 N HCl (120 mL) was added dropwise a solution of NaNO$_2$ (3.05 g, 44.151 mmol) in water (30 mL) at 0° C. over 2 h. After stirring at rt for 3 h, the reaction mixture was filtered to provide the desired product I-5 (4.356 g) as a yellow solid.

GC-MS (EI, m/z)=197 (M$^+$).

1.4. 7-isopropoxy-3-methyl-5-(methylthio)-3H-[1,2,3]triazolo[4,5-d]pyrimidine (I-6)

A mixture of the compound I-5 (4.356 g, 22.087 mmol), CsF (13.42 g, 88.348 mmol) and 2-iodopropane (6.62 mL, 66.261 mmol) in DMF (50 mL) was heated to 70° C. to 80° C. for 3 h. After cooling down to rt, the mixture was diluted with EtOAc and washed with water. The organic layer was dried over Na$_2$SO$_4$, concentrated under reduced pressure, and the residue was purified by column chromatography to afford the desired product I-6 (2.82 g) as a yellow solid.

GC-MS (EI, m/z)=239 (M$^+$).

1.5. 7-Isopropoxy-3-methyl-5-(methylsulfonyl)-3H-[1,2,3]triazolo[4,5-d]pyrimidine (I-7)

To a solution of the compound I-6 (2.82 g, 11.784 mmol) in CH$_2$Cl$_2$ (35 mL) was added portionwise mCPBA (6.1 g, 35.3 mmol) at 0° C. The reaction mixture was stirred at rt for 4 h, concentrated under reduced pressure. The residue was diluted with EtOAc, washed with saturated NaHCO$_3$. The organic layer was dried over Na$_2$SO$_4$, concentrated under reduced pressure. The residue was diluted with ether and the precipitate was filtered to afford the desired product (2.76 g) as a white solid.

GC-MS (EI, m/z)=271 (M$^+$).

Preparation Example 2: 3-Methyl-5-(methylsulfonyl)-3,6-dihydro-7H-[1,2,3]triazolo[4,5-d]pyrimidin-7-one (I-7')

To a solution of the compound I-5 in water was added Oxone® at rt. After stirring at rt for 3 h, the reaction mixture was diluted with EtOAc and washed with saturated NaHCO$_3$. The organic layer was dried over Na$_2$SO$_4$, concentrated under reduced pressure, the residue was diluted with ether and filtered to afford the desired product as a white solid.

LC-MS (ESI, m/z)=230.2 (M+H$^+$).

Preparation Example 3: 1-(2,6-Difluoro-4-substituted-phenyl)piperazine hydrochloride (I-3A through I-3E), 4-(2-(3,5-difluoro-4-(piperazin-1-yl)phenoxy)ethyl)morpholine hydrochloride (I-3F) and 2-(3,5-difluoro-4-(piperazin-1-yl)phenoxy)-N,N-dimethylethan-1-amine hydrochloride (I-3G)

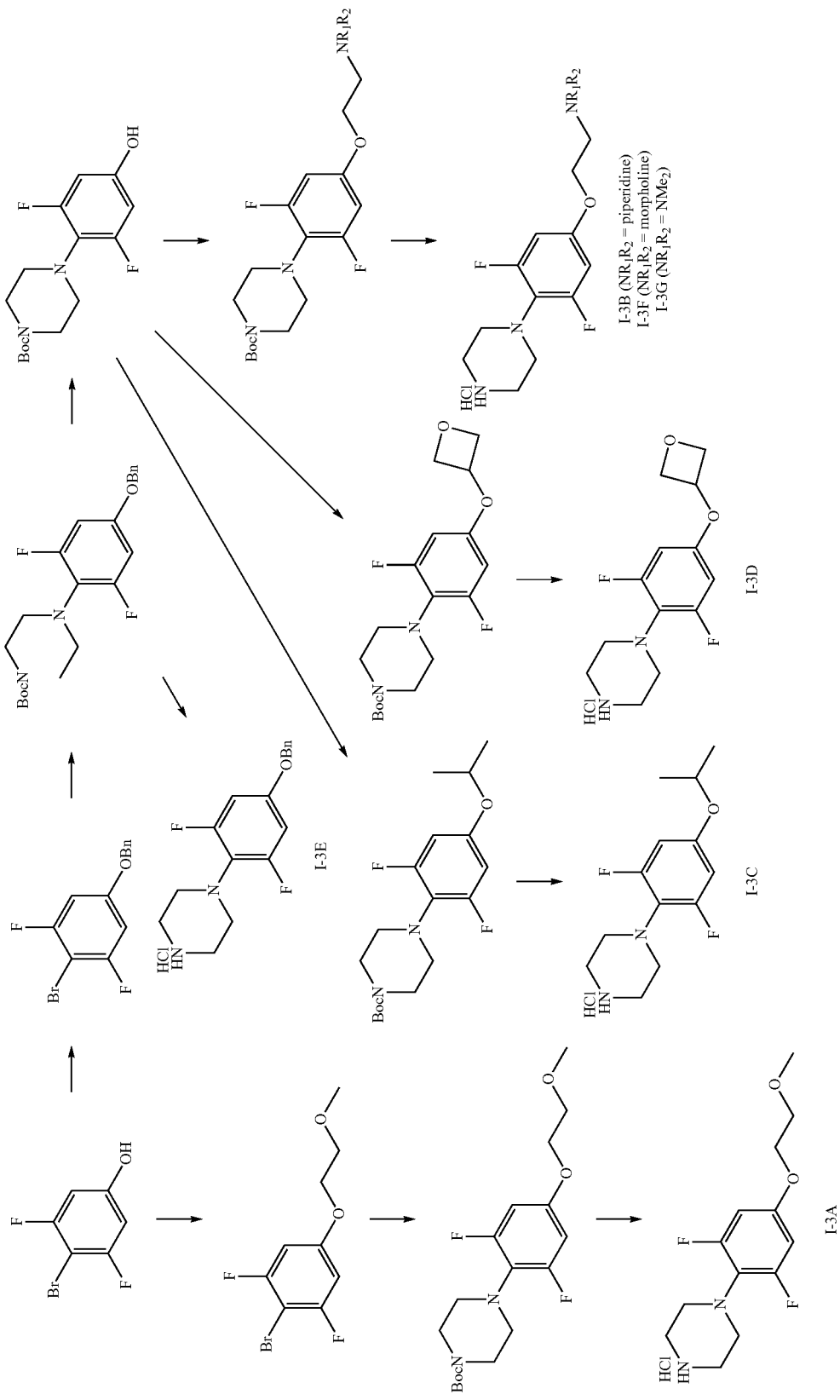

3.1. 5-(Benzyloxy)-2-bromo-1,3-difluorobenzene

A mixture of 4-bromo-3,5-difluorophenol (7 g, 33.49 mmol), benzyl bromide (4.0 mL, 40.18 mmol) and $K_2CO_3$ (13.8 g, 100.47 mmol) in DMF (83 mL) was heated at 50° C. to 60° C. under microwave heating condition for 14 h. After cooling down to rt, the reaction mixture was diluted with EtOAc and washed with water. The organic layer was dried over $Na_2SO_4$, and concentrated under reduced pressure to afford the desired product (9.6 g) as a yellow oil.
LC-MS (ESI, m/z)=299.0 (M+H$^+$).

3.2. tert-Butyl 4-(4-(benzyloxy)-2,6-difluorophenyl)piperazine-1-carboxylate A mixture of the compound (1 g, 3.34 mmol) obtained in Preparation Example 3.1 Boc-piperazine (1.49 g, 8.02 mmol), sodium tert-butoxide (898 mg, 9.352 mmol), BINAP (249 mg, 0.4 mmol) and $Pd_2(dba)_3$ (122 mg, 0.133 mmol) in toluene (10 mL) was heated at 130° C. under microwave heating condition for 20 min. After cooling down to rt, the mixture was concentrated under reduced pressure and the residue was purified by column chromatography to afford the desired product (459 mg) as a pink solid.
LC-MS (ESI, m/z)=405.2 (M+H$^+$).

3.3. tert-Butyl 4-(2,6-difluoro-4-hydroxyphenyl)piperazine-1-carboxylate

To a solution of the compound (200 mg, 0.917 mmol) obtained in Preparation Example 3.2 in MeOH (2.5 mL) was added 10% Pd/C. After stirring at rt for 3 h under hydrogen gas, the reaction mixture was filtered through a Celite pad. The filtrate was concentrated under reduced pressure to afford the desired product (154 mg, 0.489 mmol, 98%) as a white solid.

3.4. tert-Butyl 4-(2,6-difluoro-4-(2-(piperidin-1-yl)ethoxy)phenyl)piperazine-1-carboxylate A mixture of the phenolic compound (300 mg, 0.954 mmol), 1-(2-chloroethyl)piperidine hydrochloride (211 mg, 1.145 mmol), and $K_2CO_3$ (527 mg, 3.816 mmol) in DMF (3.0 mL) was heated to 50° C. to 60° C. for 17 h. After cooling down to rt, the mixture was diluted with EtOAc and washed with water. The organic layer was dried over $Na_2SO_4$ and concentrated under reduced pressure to afford the desired product (390 mg, 0.917 mmol, yield 96%) as a white solid.
LC-MS (ESI, m/z)=426.2 (M+H$^+$).

3.5. 1-(2,6-Difluoro-4-(2-(piperidin-1-yl)ethoxy)phenyl)piperazine dihydrochloride To a solution of the compound (390 mg, 0.917 mmol) obtained in Preparation Example 3.4 in $CH_2Cl_2$ (1 mL) and MeOH (0.5 mL) was added 4 M HCl (3 mL). After stirring at rt for 4 h, the reaction mixture was concentrated under reduced pressure to afford the desired product I-3B (390 mg) as a white solid.
LC-MS (ESI, m/z)=326.2 (M+H$^+$).

3.6. 1-(2,6-Difluoro-4-(2-eee(methoxyethoxy)phenyl)piperazine hydrochloride

The compound I-3A was prepared by the following sequence of reactions: O-alkylation used in Preparation Example 3.1 N-arylation used in Preparation Example 3.2 and Boc-group deprotection used in Preparation Example 3.5.
LC-MS (ESI, m/z)=273.2 (M+H$^+$).

In an analogous manner the following compounds synthesized following the above procedure (Preparation Example 3.4 and 3.5):

3.7. 1-(2,6-Difluoro-4-isopropoxyphenyl)piperazine hydrochloride

From tert-butyl 4-(2,6-difluoro-4-hydroxyphenyl)piperazine-1-carboxylate and 2-iodopropane: 1-(2,6-difluoro-4-isopropoxyphenyl)piperazine hydrochloride was obtained (I-3C).
LC-MS (ESI, m/z)=257.3 (M+H$^+$).

3.8. 1-(2,6-Difluoro-4-(oxetan-3-yloxy)phenyl)piperazine hydrochloride

From tert-butyl 4-(2,6-difluoro-4-hydroxyphenyl)piperazine-1-carboxylate and oxetan-3-yl 4-methylbenzenesulfonate: 1-(2,6-difluoro-4-(oxetan-3-yloxy)phenyl)piperazine hydrochloride was obtained (I-3D).
LC-MS (ESI, m/z)=271.3 (M+H$^+$).

3.9. 1-(4-(Benzyloxy)-2,6-difluorophenyl)piperazine hydrochloride

From tert-butyl 4-(2,6-difluoro-4-hydroxyphenyl)piperazine-1-carboxylate and (bromomethyl)benzene: 1-(4-(benzyloxy)-2,6-difluorophenyl)piperazine hydrochloride was obtained (I-3E).
LC-MS (ESI, m/z)=305.3 (M+H$^+$).

3.10. 4-(2-(3,5-Difluoro-4-(piperazin-1-yl)phenoxy)ethyl)morpholine dihydrochloride From tert-butyl 4-(2,6-difluoro-4-hydroxyphenyl)piperazine-1-carboxylate and 4-(2-chloroethyl)morpholine hydrochloride: 4-(2-(3,5-difluoro-4-(piperazin-1-yl)phenoxy)ethyl)morpholine dihydrochloride was obtained (I-3F).
LC-MS (ESI, m/z)=328.4 (M+H$^+$).

3.11. 2-(3,5-Difluoro-4-(piperazin-1-yl)phenoxy)-N,N-dimethylethan-1-amine dihydrochloride From tert-butyl 4-(2,6-difluoro-4-hydroxyphenyl)piperazine-1-carboxylate and 2-chloro-N,N-dimethylethanamine hydrochloride: 2-(3,5-difluoro-4-(piperazin-1-yl)phenoxy)-N,N-dimethylethan-1-amine dihydrochloride was obtained (I-3G).
LC-MS (ESI, m/z)=286.3 (M+H$^+$).

Preparation Example 4: 4-(3,5-Difluoro-4-(piperazin-1-yl)benzyl)morpholine dihydrochloride

4.1. tert-Butyl 4-(2,6-difluoro-4-formylphenyl)piperazine-1-carboxylate

A mixture of 3,4,5-trifluorobenzaldehyde (2 g, 12.493 mmol), Boc-piperazine (2.33 g, 12.493 mmol) and $K_2CO_3$ (3.45 g, 24.986 mmol) in DMF (4 mL) was heated to 110° C. to 120° C. for 18 h. After cooling down to rt, the mixture was diluted with EtOAc and washed with water. The organic layer was dried over $Na_2SO_4$ and concentrated under reduced pressure. The residue was purified by column chromatography to afford the desired product (2.7 g) as a yellow solid.

LC-MS (ESI, m/z)=327.1 (M+H$^+$).

4.2. tert-Butyl 4-(2,6-difluoro-4-(morpholinomethyl)phenyl)piperazine-1-carboxylate A mixture of the compound (500 mg, 1.532 mmol) obtained in Preparation Example 4.1 morpholine (0.27 mL, 3.064 mmol), and Ti(OiPr)$_4$ (0.91 mL, 3.064 mmol) in MeOH (5 mL) was stirred at rt for 17 h. NaCNBH$_3$ (193 mg, 3.064 mmol) was added to the reaction mixture at 0° C. After stirring at rt for 3 h, the mixture was concentrated under reduced pressure, and the residue was diluted with EtOAc and filtered through a Celite pad. The organic layer was washed with water, dried over Na$_2$SO$_4$, and concentrated under reduced pressure. The residue was purified by column chromatography to afford the desired product (272 mg) as a yellow oil.

LC-MS (ESI, m/z)=398.2 (M+H$^+$).

4.3. 4-(3,5-Difluoro-4-(piperazin-1-yl)benzyl)morpholine dihydrochloride

Using the compound obtained in Preparation Example 4.2 the desired product was prepared by following a similar method to that described in Preparation Example 3.5.

LC-MS (ESI, m/z)=298.1 (M+H$^+$).

Preparation Example 5: 1-(3,5-Difluoro-4-(piperazin-1-yl)phenyl)ethanol hydrochloride

5.1. tert-Butyl 4-(2,6-difluoro-4-(1-hydroxyethyl)phenyl)piperazine-1-carboxylate To a solution of the compound (600 mg, 1.839 mmol) obtained in Preparation Example 4.1 in THF (5 mL) was added dropwise 1.6 M MeLi in diethyl ether (1.26 mL, 2.023 mmol) at −78° C. for 2 h. The reaction mixture was slowly warmed to rt. After the reaction mixture was quenched with a few drops of water and concentrated under reduced pressure. The residue was diluted with EtOAc and washed with water. The organic layer was dried over Na$_2$SO$_4$ and concentrated under reduced pressure, and the residue was purified by column chromatography to afford the desired product (503 mg) as a yellow solid.

LC-MS (ESI, m/z)=342.2 (M+H$^+$).

5.2. 1-(3,5-Difluoro-4-(piperazin-1-yl)phenyl)ethanol hydrochloride

The compound (250 mg, 0.730 mmol) obtained in Preparation Example 5.1 was deprotected by 4 M HCl (4 mL) by following a similar method to that described in Preparation Example 3.5 to afford the desired product (226 mg, quant) as a yellow solid.

LC-MS (ESI, m/z)=243.1 (M+H$^+$).

Preparation Example 6: 1-(2,6-Difluoro-4-(1-methoxyethyl)phenyl)piperazine hydrochloride

6.1. tert-Butyl 4-(2,6-difluoro-4-(1-methoxyethyl)phenyl)piperazine-1-carboxylate To a solution of the compound (250 mg, 0.730 mmol) obtained in Preparation Example 5.1 in THF (2.5 mL) was added NaH (53 mg, 1.095 nmmol, 55% in mineral oil) at 0° C. The reaction mixture was stirred for 10 min and dimethyl sulfate was added dropwise to the reaction mixture at 0° C. After stirring at rt for 1 h, the reaction mixture was concentrated under reduced pressure and the residue was diluted with EtOAc. The organic layer was washed with water, dried over Na$_2$SO$_4$, and concentrated under reduced pressure. The residue was purified by column chromatography to afford the desired product (294 mg) as a colorless oil.

LC-MS (ESI, m/z)=356.2 (M+H$^+$).

6.2. 1-(2,6-Difluoro-4-(1-methoxyethyl)phenyl)piperazine hydrochloride

Using the compound (294 mg, 0.730 mmol) obtained in Preparation Example 6.1 the compound (198 mg) was prepared by following a similar method to that described in Preparation Example 3.5.

LC-MS (ESI, m/z)=257.1 (M+H$^+$).

Preparation Example 7: 4-(2,6-Difluoro-4-(2-methoxyethoxy)phenyl)piperidin-4-ol hydrochloride

7.1. tert-Butyl 4-(2,6-difluoro-4-(2-methoxyethoxy)phenyl)piperazin-4-hydroxypiperidine-1-carboxylate To a solution of 2-bromo-1,3-difluoro-5-(2-methoxyethoxy)benzene (600 mg, 2.246 mmol) in ether (20 mL) was added dropwise 2.5 M n-BuLi in hexane (0.98 mL, 2.47 mmol) at −78° C. over 10 min. After stirring at −78° C. for 30 min a solution of Boc-piperidone (537 mg, 2.69 mmol) in ether (4 mL) was added dropwise to the reaction mixture at −78° C. over 20 min. The reaction mixture was allowed to warm to rt, quenched with water (15 mL), and diluted with ether. The organic layer was dried over Na$_2$SO$_4$ and concentrated under reduced pressure to afford the desired product (1.01 g) as a yellow oil.

LC-MS (ESI, m/z)=388.2 (M+H$^+$).

7.2. 4-(2,6-Difluoro-4-(2-methoxyethoxy)phenyl)piperidin-4-ol hydrochloride Using the desired product obtained in Preparation Example 7.1 the compound (370 mg) was prepared by following a similar method to that described in Preparation Example 3.5.

LC-MS (ESI, m/z)=288.1 (M+H$^+$).

Preparation Example 8: 4-(1H-tetrazol-5-yl)piperidine hydrochloride

8.1. tert-Butyl 4-(1H-tetrazol-5-yl)piperidine-1-carboxylate

A mixture of tert-butyl 4-cyanopiperidine-1-carboxylate (1 g, 4.75 mmol), sodium azide (923 mg, 14.26 mmol), and ammonium chloride (763 g, 14.26 mmol) in DMF (9.4 mL) was heated to 140° C. for 20 h. After cooling down to rt, the reaction mixture was diluted with EtOAc, washed with 0.5 N HCl and brine. The organic layer was dried over Na$_2$SO$_4$, and concentrated under reduced pressure. The residue was diluted with ether and the precipitate was filtered to afford the desired product (764 mg).

LC-MS (ESI, m/z)=254.1 (M+H$^+$).

8.2. 4-(1H-tetrazol-5-yl)piperidine hydrochloride

Using the compound obtained in Preparation Example 8.1 the compound was prepared by following a similar method to that described in Preparation Example 3.5.

LC-MS (ESI, m/z)=154.1 (M+H$^+$).

Preparation Examples 9 and 10

3-(3,5-Difluoro-4-(piperazin-1-yl)phenyl)propane-1,2-diol hydrochloride (A) and 1-(3,5-difluoro-4-(piperazin-1-yl)phenyl)ethane-1,2-diol hydrochloride (B)

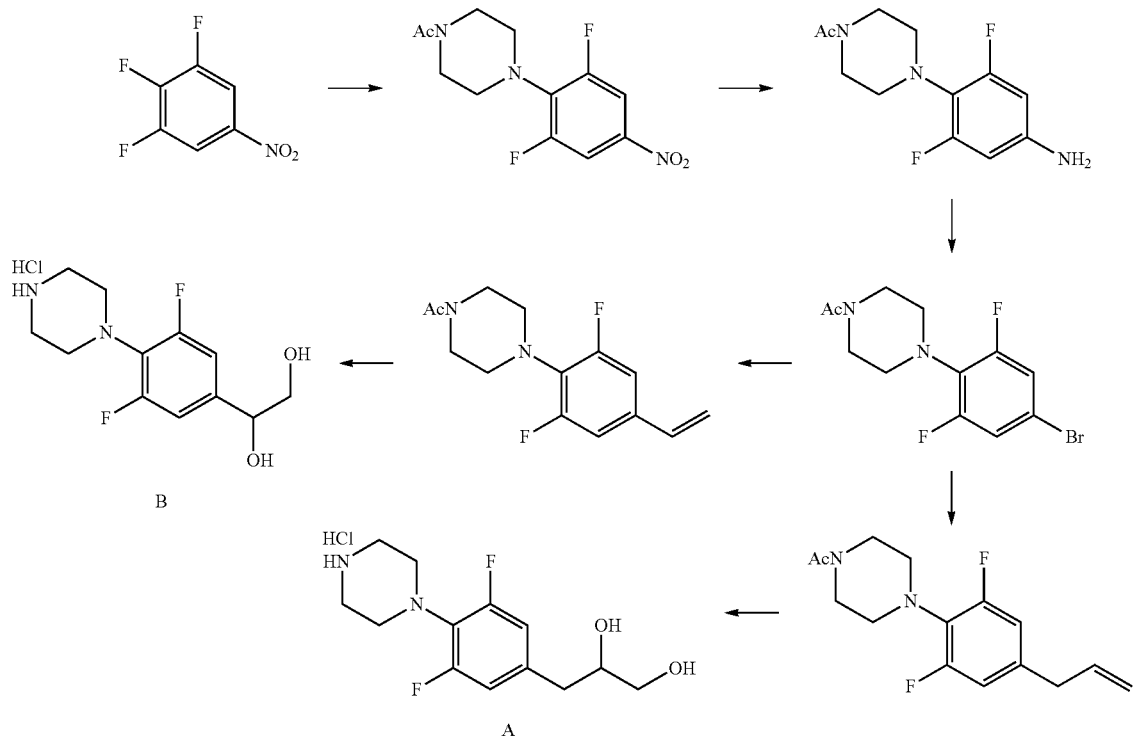

9.1. 1-(4-(2,6-Difluoro-4-nitrophenyl)piperazin-1-yl)ethan-1-one

A mixture of 3,4,5-Trifluoronitrobenzene and N-acetylpiperazine in MeCN was heated to 60° C. for 1 h. The reaction mixture was concentrated under reduced pressure and the residue was purified by column chromatography.
LC-MS (ESI, m/z)=287.2 (M+H$^+$).

9.2. 1-(4-(2,6-Difluoro-4-aminophenyl)piperazin-1-yl)ethan-1-one

The compound obtained in Preparation Example 9.1 was hydrogenated by Pd/C under hydrogen gas to afford the desired product.
LC-MS (ESI, m/z)=256.2 (M+H$^+$).

9.3. 1-(4-(4-Bromo-2,6-difluorophenyl)piperazin-1-yl)ethan-1-one

The amine group of the compound obtained in Preparation Example 9.2 was replaced by bromide through the Sandmeyer reaction.
LC-MS (ESI, m/z)=319.0 (M+H$^+$).

9.4. 1-(4-(4-Allyl-2,6-difluorophenyl)piperazin-1-yl)ethan-1-one

An allyl group was introduced to the compound obtained in Preparation Example 9.3 via the Stille coupling reaction using Pd(PPh$_3$)$_4$, allylSnBu$_3$, and DMF (100° C., 18 h). Then, the desired product was purified by column chromatography.
LC-MS (ESI, m/z)=281.3 (M+H$^+$).

9.5. 3-(3,5-Difluoro-4-(piperazin-1-yl)phenylpropane-1,2-diol hydrochloride (A)

The allylic compound obtained in Preparation Example 9. was dihydroxylated by OsO$_4$. Then, the desired product was afforded by removing the N-acetyl group of the dihydroxylated compound under acidic conditions.
LC-MS (ESI, m/z)=273.3 (M+H$^+$).

10.1. 1-(4-(4-Vinyl-2,6-difluorophenyl)piperazin-1-yl)ethan-1-one

The vinyl group was introduced via the Stille coupling reaction employed in Preparation Example 9.3 using (vinyl)SnBu$_3$.
LC-MS (ESI, m/z)=267.3 (M+H$^+$).

10.2. 1-(3,5-Difluoro-4-(piperazin-1-yl)phenyl)ethane-1,2-diol hydrochloride (B)

The vinylic compound obtained in Preparation Example 10.1 was dihydroxylated by OsO$_4$. Then, the compound B was obtained by removing the N-acetyl group of the dihydroxylated compound under acidic conditions.
LC-MS (ESI, m/z)=259.2 (M+H$^+$).

Preparation Example 11: 3,5-Difluoro-N-(2-methoxyethyl)-4-(piperazin-1-yl)aniline hydrochloride (I-i)

11.1. tert-Butyl 4-(2,6-difluoro-4-nitrophenyl)piperazine-1-carboxylate

To a solution of 1,2,3-trifluoro-5-nitrobenzene (1 g, 5.65 mmol) in MeCN (11 mL) was added Boc-piperazine (2.63, 14.12 mmol) at rt. The reaction mixture was stirred at 60° C. for 3 h. After cooling down to rt, the mixture was diluted with EtOAc and washed with water. The organic layer was dried over $Na_2SO_4$, and concentrated under reduced pressure. The residue was purified by column chromatography to afford the desired product (1.93 g, quant) as a yellow solid.

LC-MS (ESI, m/z)=344.1 (M+H$^+$).

11.2. tert-Butyl 4-(4-amino-2,6-difluorophenyl)piperazine-1-carboxylate

The compound (1.75 g, 5.09 mmol) obtained in Preparation Example 11.1 was hydrogenated by Pd/C under hydrogen gas to afford the desired product (1.57 g) as a yellow solid.

LC-MS (ESI, m/z)=314.1 (M+H$^+$).

11.3. tert-Butyl 4-(2,6-difluoro-4-(2-methoxyethylamino)phenyl)piperazine-1-carboxylate To a solution of the compound (1.57 g, 5.01 mmol) obtained in Preparation Example 11.2 in DMF was added portionwise NaH (437 mg, 10.02 mmol, 55% in mineral oil) at 0° C. over 30 min. A solution of 1-bromo-2-methoxyethane (835 mg, 6.01 mmol) in DMF (3 mL) was added dropwise to the reaction mixture at 0° C. After stirring overnight at rt, the mixture was quenched with iced water and diluted with EtOAc. The organic layer was washed with water, dried over $Na_2SO_4$, and concentrated under reduced pressure. The residue was purified by column chromatography to afford the desired product (140 mg, quant) as a yellow oil.

LC-MS (ESI, m/z)=372.2 (M+H$^+$).

11.4. 3,5-Difluoro-N-(2-methoxyethyl)-4-(piperazin-1-yl)aniline hydrochloride The desired product (110 mg) was afforded as a white solid by deprotecting the compound (140 mg, 0.376 mmol) obtained in Preparation Example 11.3 using 4 M HCl.

LC-MS (ESI, m/z)=272.1 (M+H$^+$).

Preparation Example 12: 2-(3,5-Difluoro-4-(piperazin-1-yl)phenoxy)-1-(substituted-1-yl)ethanone hydrochloride (I-12A and I-12B), 1-(2,6-difluoro-4-(2-(pyrrolidin-1-yl)ethoxy)phenyl)piperazine hydrochloride (I-12C), 1-(2-(3,5-difluoro-4-(piperazin-4-yl)phenoxy)ethyl)-substituted hydrochloride (I-12D and I-12F), 1-(4-(2-azidoethoxy)-2,6-difluorophenyl)piperazine hydrochloride (I-12E), benzyl 1-(2-(3,5-difluoro-4-(piperazin-1-yl)phenoxy)ethyl)piperidin-4-ylcarbamate hydrochloride (I-12G) and 1-(2-(3,5-difluoro-4-(piperazin-1-yl)phenoxy)ethyl)piperidin-2-one (I-12H)

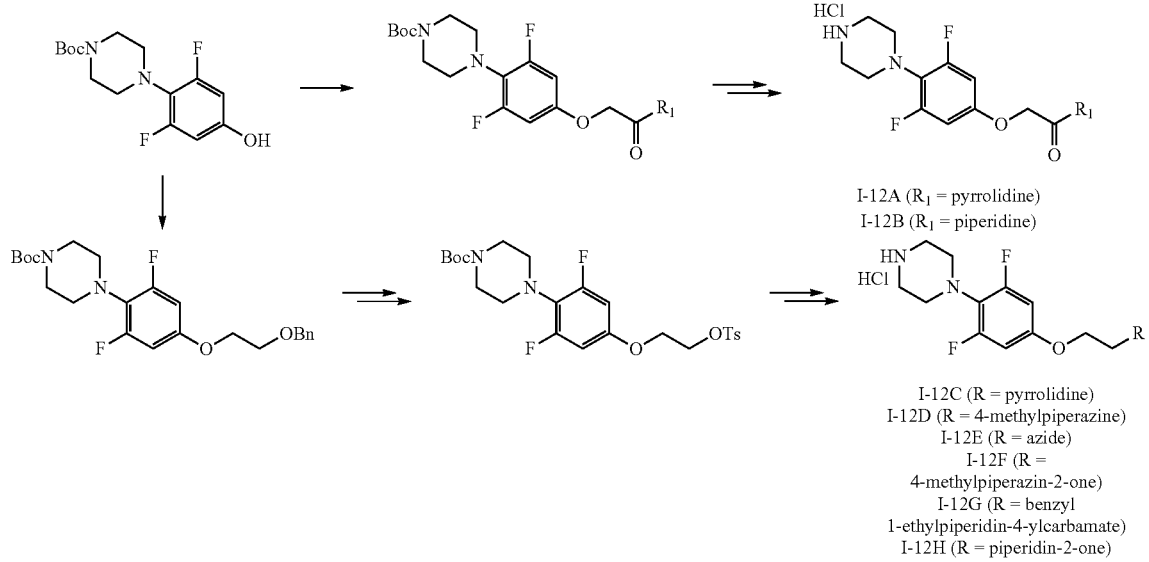

I-12A (R$_1$ = pyrrolidine)
I-12B (R$_1$ = piperidine)

I-12C (R = pyrrolidine)
I-12D (R = 4-methylpiperazine)
I-12E (R = azide)
I-12F (R = 4-methylpiperazin-2-one)
I-12G (R = benzyl 1-ethylpiperidin-4-ylcarbamate)
I-12H (R = piperidin-2-one)

12.1. tert-Butyl 4-(2,6-difluoro-4-(2-oxo-2-(pyrrolidin-1-yl)ethoxy)phenyl)piperazin-1-carboxylate To a solution of pyrrolidine (377.8 mg, 5.313 mmol) in THF (2.5 mL) was added dropwise a solution of 2-chloroacetyl chloride (300 mg, 2.656 mmol) in THF (2.5 mL) at 0° C. over 5 min. After stirring at rt for 15 h, the reaction mixture was diluted with EtOAc and washed with water. The organic layer was dried over $Na_2SO_4$ and concentrated under reduced pressure to afford the desired product (438 mg) as a yellow oil. A mixture of 2-chloro-1-(pyrrolidin-1-yl)ethanone (169 mg, 1.145 mmol), the compound (300 mg, 0.954 mmol) obtained in Preparation Example 3.3 and $K_2CO_3$ (527 mg, 3.816 mmol) in DMF (3.2 mL) was stirred at rt for 17 h. The reaction mixture was diluted with EtOAc and washed with water. The organic layer was dried over Na$_2$SO$_4$ and concentrated under reduced pressure to afford the desired product (346 mg) as a white solid.

12.2. 2-(3,5-Difluoro-4-(piperazin-1-yl)phenoxy)-1-(pyrrolidin-1-yl)ethanone hydrochloride (I-12A)

To a solution of tert-butyl 4-(2,6-difluoro-4-(2-oxo-2-(pyrrolidin-1-yl)ethoxy)phenyl)piperazin-1-carboxylate (336 mg, 0.790 mmol) in CH$_2$Cl$_2$ (0.5 mL) was added 4 M HCl (2 mL). The mixture was stirred at rt for 3 h and concentrated under reduced pressure. The residue was diluted with ether and the precipitate was filtered to afford the desired product (295 mg) as a white solid.
LC-MS (ESI, m/z)=326.1 (M+H$^+$).

12.3. tert-Butyl 4-(2,6-difluoro-4-(2-oxo-2-(piperidin-1-yl)ethoxy)phenyl)piperazin-1-carboxylate The desired product was prepared in analogously with the procedure in Preparation Example 12.1. The pyrrolidine motif was replaced with the piperidine to afford the desired product.
LC-MS (ESI, m/z)=440.2 (M+H$^+$).

12.4. 2-(3,5-Difluoro-4-(piperazin-1-yl)phenoxy)-1-(piperidin-1-yl)ethanone hydrochloride (I-12B)

The compound (336 mg, 0.790 mmol) obtained in Preparation Example 12.3 was deprotected by 4 M HCl to afford the desired product (243 mg) as a white solid.
LC-MS (ESI, m/z)=340.1 (M+H$^+$).

12.5. tert-Butyl 4-(4-(2-(benzyloxy)ethoxy)-2,6-difluorophenyl)piperazin-1-carboxylate A mixture of the compound (1 g, 3.181 mmol) obtained in Preparation Example 3.3 benzyl-2-bromoethylamine (851 mg, 3.818 mmol) and K$_2$CO$_3$ (1.32 g, 9.544 mmol) in DMF (6.4 mL) was heated to 70° C. to 80° C. for 2 h. After cooling down to rt, the reaction mixture was diluted with EtOAc and washed with brine. The organic layer was dried over Na$_2$SO$_4$ and concentrated under reduced pressure to afford the desired product (1.427 g) as a yellow oil.
LC-MS (ESI, m/z)=449.2 (M+H$^+$).

12.6. tert-Butyl 4-(2,6-difluoro-4-(2-hydroxyethoxy)phenyl)piperazin-1-carboxylate To a solution of the compound (1.427 g, 3.181 mmol) obtained in Preparation Example 12.5 in MeOH (10.6 mL) was added 10% Pd/C (428 mg). After stirring at rt for 2 h under hydrogen gas. The mixture was filtered through a Celite pad and the filtrate was concentrated under reduced pressure to afford the desired product (1.14 g) as a pale yellow solid.
LC-MS (ESI, m/z)=359.1 (M+H$^+$).

12.7. tert-Butyl 4-(2,6-difluoro-4-(2-(tosyloxy)ethoxy)phenyl)piperazin-1-carboxylate A mixture of the compound (1.14 g, 3.181 mmol) obtained in Preparation Example 12.6 4-methylbenzyl-1-sulfonyl chloride (909.8 mg, 4.722 mmol), TEA (804.8 mg, 7.953 mmol) and DMAP (97.2 mg, 0.057 mmol) in CH$_2$Cl$_2$ (10.6 mL) was stirred at rt for 3 h. The mixture was diluted with EtOAc, washed with 0.5 N HCl and saturated NaHCO$_3$. The organic layer was dried over Na$_2$SO$_4$, concentrated under reduced pressure to afford the desired product (1.44 g) as a white solid.
LC-MS (ESI, m/z)=513.2 (M+H$^+$).

12.8. tert-Butyl 4-(2,6-difluoro-4-(2-(4-methylpiperazin-1-yl)ethoxy)phenyl)piperazin-1-carboxylate To a solution of the compound (368 mg, 0.718 mmol) obtained in Preparation Example 12.7 1-methylpiperazine (143.8 mg, 1.436 mmol) in DMF (2.4 mL) was heated to 50° C. to 60° C. for 15 h. After cooling down to rt, the mixture was diluted with EtOAc and washed with water. The organic layer was dried over Na$_2$SO$_4$ and concentrated under reduced pressure to afford the desired product (270 mg) as a yellow oil.

12.9. 1-(2-(3,5-Difluoro-4-(piperazin-1-yl)phenoxy)ethyl)-4-methylpiperazine dihydrochloride (I-12D)

The compound (270 mg, 0.613 mmol) obtained in Preparation Example 12.8 was deprotected with 4 M HCl to afford the desired product (253 mg) as a white solid.
LC-MS (ESI, m/z)=341.2 (M+H$^+$).

12.10. 1-(2-(3,5-Difluoro-4-(piperazin-1-yl)phenoxy)ethyl)-4-pyrrolidine dihydrochloride (I-12C)

The desired product was synthesized by following the reaction conditions used in Preparation Examples 12.8 and 12.9.
LC-MS (ESI, m/z)=312.2 (M+H$^+$).

12.11. 1-(4-(2-Azidoethoxy)-2,6-difluorophenyl)piperazine hydrochloride (I-12E)

The desired product was synthesized by following the reaction conditions used in Preparation Examples 12.8 and 12.9.
LC-MS (ESI, m/z)=284.1 (M+H$^+$).

12.12. 1-(2-(3,5-Difluoro-4-(piperazin-1-yl)phenoxy)ethyl)-4-methylpiperazin-2-one hydrochloride (I-12F)

The desired product was synthesized by following reaction conditions similar to those used in Preparation Examples 12.8 and 12.9.
LC-MS (ESI, m/z)=355.2 (M+H$^+$).

12.13. Benzyl 1-(2-(3,5-difluoro-4-(piperazin-1-yl)phenoxy)ethyl)piperidin-4-ylcarbamate dihydrochloride (I-12G)

The desired product was synthesized by following the reaction conditions used in Preparation Examples 12.8 and 12.9.
LC-MS (ESI, m/z)=475.2 (M+H$^+$).

12.14. 1-(2-(3,5-Difluoro-4-(piperazin-1-yl)phenoxy)ethyl)piperidin-2-one (I-12H)

The desired product was synthesized by following the reaction conditions used in Preparation Examples 12.8 and 12.9.
LC-MS (ESI, m/z)=340.2 (M+H$^+$).

37

Preparation Example 13: 1-(2,6-Difluoro-4-(3-methoxypropyl)phenyl)piperazine hydrochloride (I-13A)

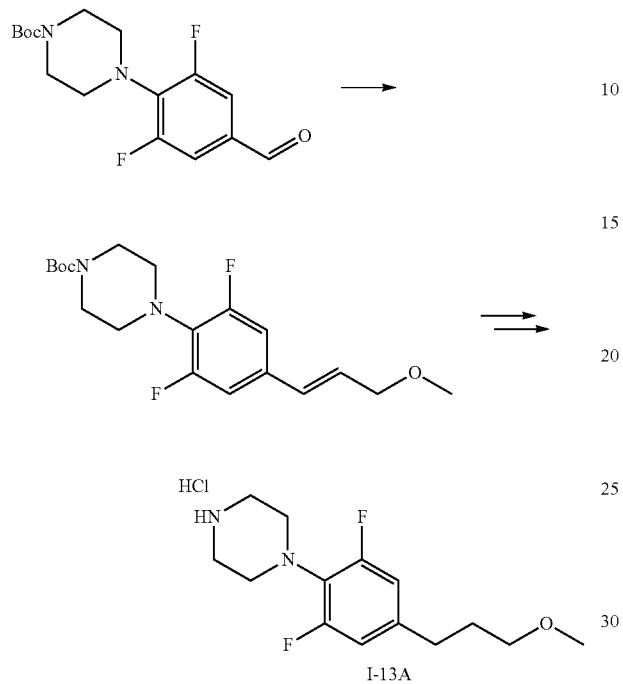

I-13A

13.1. tert-Butyl 4-(2,6-difluoro-4-(2-oxo-2-(pyrrolidin-1-yl)ethoxy)phenyl)piperazin-1-carboxylate To a solution of (2-methoxyethyl)triphenylphosphonium bromide (1.424 g, 3.549 mmol) in THF (10 mL) was added dropwise 2.5 M n-BuLi in hexane (1.42 mL) at 0° C. for 0.5 h. A solution of the compound (772 mg, 2.366 mmol) obtained in Preparation Example 4.1 in THF (2 mL) was added dropwise to the reaction mixture at 0° C. After stirring at rt for 18 h, the reaction mixture was quenched with a few drops of MeOH, and diluted with EtOAc. The organic layer was washed with water, dried over $Na_2SO_4$, concentrated under reduced pressure. The residue was purified by column chromatography to afford the desired product (239 mg, 0.649 mmol) as a colorless oil.

LC-MS (ESI, m/z)=369.2 (M+H$^+$).

13.2. 1-(2,6-Difluoro-4-(3-methoxypropyl)phenyl)piperazine hydrochloride (I-13A)

To a solution of the compound (239 mg, 0.165 mmol) obtained in Preparation Example 13.1 in MeOH (4 mL) was added 10% Pd/C (120 mg). After stirring at rt for 1 h under hydrogen gas, the mixture was filtered through a Celite pad. The filtrate was concentrated under reduced pressure to afford the intermediate (164 mg, 0.434 mmol) as a colorless oil. The obtained intermediate was deprotected using 4 M HCl to afford the desired product (164 mg) as a white solid.

LC-MS (ESI, m/z)=271.1 (M+H$^+$).

38

Preparation Example 14: 1-(2-(3,5-Difluoro-4-(piperazin-1-yl)phenoxy)ethyl)pyrrolidin-3-ol hydrochloride (I-14A), 1-(2-(3,5-difluoro-4-(piperazin-1-yl)phenoxy)ethyl)piperidin-4-ol hydrochloride (I-14B) and 1-(2-(3,5-difluoro-4-piperazin-1-yl)phenoxy)ethyl)-4-methylpiperidin-4-ol hydrochloride (I-14C)

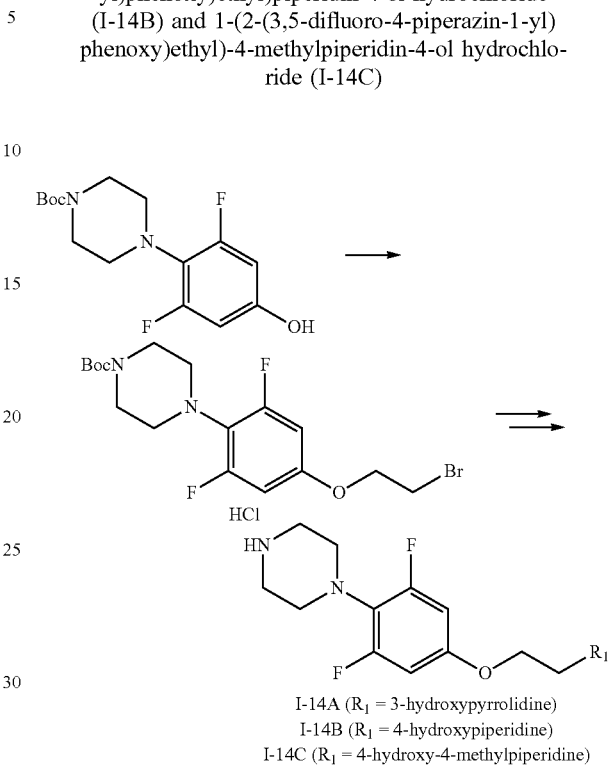

I-14A ($R_1$ = 3-hydroxypyrrolidine)
I-14B ($R_1$ = 4-hydroxypiperidine)
I-14C ($R_1$ = 4-hydroxy-4-methylpiperidine)

14.1. tert-Butyl 4-(4-(2-bromomethoxy)-2,6-difluorophenyl)piperazin-1-carboxylate To a mixture of tert-butyl 4-(2,6-difluoro-4-hydroxyphenyl)piperazin-1-carboxylate (3.14 g, 10 mmol) and $K_2CO_3$ (4.2 g, 30 mmol) in MeCN (50 mL) was added 1,2-dibromoethane (3.8 g, 20 mmol). The reaction mixture was heated to reflux for 12 h. After cooling down to rt, the reaction mixture was filtered and concentrated under reduced pressure. The residue was purified by column chromatography to afford the desired product (3.5 g) as a white solid.

14.2. 1-(2-(3,5-Difluoro-4-(piperazin-1-yl)phenoxy)ethyl)pyrrolidin-3-ol hydrochloride (I-14A)

The compound (0.42 g, 1.00 mmol) obtained in Preparation Example 14.1 was reacted with 3-hydroxypyrrolidine (0.13 g, 1.5 mmol) to afford an aminated intermediate. The intermediate was treated with 4 M HCl to remove the Boc-group of piperidine to afford the desired product (0.3 g).

14.3. 1-(2-(3,5-Difluoro-4-(piperazin-1-yl)phenoxy)ethyl)piperidin-4-ol hydrochloride (I-14B)

The desired product was synthesized by following the reaction conditions used in Preparation Examples 14.1 and 14.2.

14.4. 1-(2-(3,5-Difluoro-4-(piperazin-1-yl)phenoxy) ethyl)-4-methylpiperidin-4-ol hydrochloride (I-14C)

The desired product was synthesized by following the reaction conditions used in Preparation Examples 14.1 and 14.2.

Preparation Example 15: 4-(Benzyloxy)-6-chloro-1-methyl-1H-[1,2,3]triazolo[4,5-c]pyridine (I-15) as an intermediate

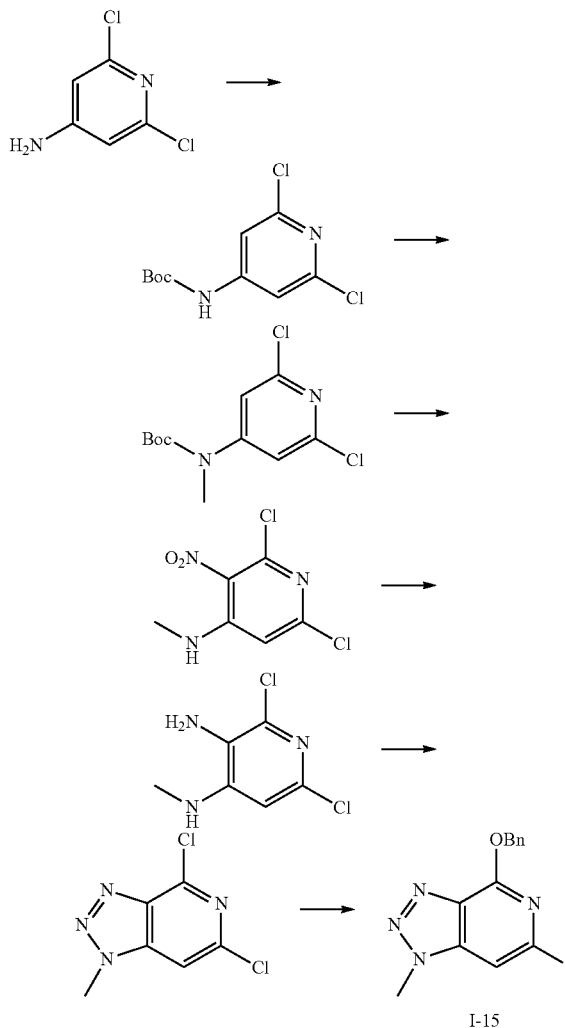

I-15

15.1. tert-Butyl 2,6-dichloropyridin-4-ylcarbamate

A mixture of 2,6-dichloropyridin-4-amine (2.1 g, 12.833 mmol), (Boc)$_2$O (3.09 g, 14.172 mmol), and DMAP (393.5 mg, 3.221 mmol) in THF (64.4 mL) was heated to 60° C. to 70° C. for 23 h. After cooling down to rt, the mixture was concentrated under reduced pressure. The residue was diluted with EtOAc, washed with saturated NH$_4$Cl solution and dried over Na$_2$SO$_4$. The organic layer was concentrated under reduced pressure, and the residue was purified by column chromatography to afford the desired product (2.04 g) as a white solid.

$^1$H NMR (300 MHz, DMSO-d$_6$) δ 10.336 (s, 1H), 7.473 (s, 2H), 1.408 (s, 9H).

15.2. tert-Butyl 2,6-Dichloropyridin-4-yl(methyl)carbamate

To a mixture of NaH (639.3 mg, 14.651 mmol, 55% in mineral oil) in DMF (20 mL) was added dropwise a solution of the compound (2.57 g, 9.767 mmol) obtained in Preparation Example 15.1 in DMF (20 mL) at 0° C. over 10 min. After stirring for 30 min, a solution of MeI (0.67 mL, 10.774 mmol) in DMF (8 mL) was added dropwise to the reaction mixture at 0° C. After stirring at rt for 1 h, the mixture was cooled down to 0° C., added water and diluted with EtOAc. The organic layer was washed with brine, dried over Na$_2$SO$_4$ and concentrated under reduced pressure. The residue was purified by column chromatography to afford the desired product (2.5 g) as a yellow oil.

$^1$H NMR (300 MHz, DMSO-d$_6$) δ 7.578 (s, 1H), 3.262 (s, 1H), 1.474 (s, 9H).

15.3. 2,6-Dichloro-N-methyl-3-nitropyridin-4-amine

To a solution of the compound (2.671 g, 9.417 mmol) obtained in Preparation Example 15.2 in concentrated sulfuric acid (9.4 mL) was added dropwise 60% to 62% nitric acid (0.8 mL, 10.359 mmol) at 0° C. over 10 min. The reaction mixture was stirred at rt for 3 h and iced water was slowly added to the solution. The precipitate was filtered to afford the desired product (1.6 g) as a yellow solid.

$^1$H NMR (300 MHz, DMSO-d$_6$) δ 7.752 (q, J=4.2 Hz, 1H), 6.979 (s, 1H), 2.821 (d, J=4.5 Hz, 1H).

15.4. 2,6-Dichloro-N$^4$-methylpyridin-3,4-diamine

To a solution of the compound (1.6 g, 7.206 mmol) obtained in Preparation Example 15.3 in MeOH (6 mL) and EtOAc (6 mL) was added 5% Pd/C (160 mg). After stirring at rt for 4 h under hydrogen gas, the mixture was filtered through a Celite pad. The filtrate was concentrated under reduced pressure, and the residue was washed with 20% EtOAc in n-hexane (20 mL) to afford the desired product (1.06 g) as a brown solid.

$^1$H NMR (300 MHz, DMSO-d$_6$) δ 6.334 (s, 1H), 6.276 (q, J=3.9 Hz, 1H), 4.879 (brs, 2H), 2.771 (d, J=4.8 Hz, 1H).

15.5. 4,6-Dichloro-1-methyl-1H-[1,2,3]triazolo[4,5-c]pyridine

To a solution of the compound (1.06 g, 5.519 mmol) obtained in Preparation Example 15.4 in 1 N HCl (22 mL) was added dropwise a solution of sodium nitrite (647 mg, 9.382 mmol) in water (5 mL) at 0° C. over 20 min. After stirring at rt for 1 h, the reaction mixture was filtered and the precipitate was washed with water to afford the desired product (983 mg) as a brown solid.

$^1$H NMR (300 MHz, DMSO-d$_6$) δ 8.239 (s, 1H), 4.327 (s, 3H).

15.6. 4-(Benzyloxy)-6-chloro-1-methyl-1H-[1,2,3]triazolo[4,5-c]pyridine (I-15)

To a mixture of NaH (644.7 mg, 14.776 mmol, 55% in mineral oil) in DMF (16 mL) was added dropwise a solution of benzylalcohol (1.53 mL, 14.776 mmol) in DMF (16 mL). The mixture was stirred at 0° C. for 30 min. A solution of the compound (2 g, 9.851 mmol) obtained in Preparation Example in 15.5 in THF (16 mL) was added dropwise to the reaction mixture was quenched with iced water and diluted with EtOAc. The organic layer was washed with brine and dried over $Na_2SO_4$. The filtrate was concentrated under reduced pressure and the residue was washed with n-hexane to afford the desired product (2.56 g) as a yellow solid.

LC-MS (ESI, m/z)=330.3 $(M+H^+)$.

Example 1: 5-(4-(2-Fluorophenyl)piperazin-1-yl)-3-methyl-3H-[1,2,3]triazolo[4,5-d]pyrimidin-7(6H)-one To a microwave reaction vial were added the compound (I-7') obtained in Preparation Example 2, 1-(2-fluorophenyl) piperazine as amine, diisopropylethylamine (DIPEA), and isopropyl alcohol (2 mL). The reaction mixture was heated at 150° C. under microwave heating condition for 30 min. The mixture was concentrated under reduced pressure and the residue was purified by column chromatography to afford the desired product.

LC-MS (ESI, m/z)=464.2 $(M+H^+)$.

Example 2: 5-(4-(2,6-Difluoro-4-(2-methoxyethoxy) phenyl)piperazin-1-yl)-3-methyl-3H-[1,2,3]triazolo [4,5-d]pyrimidin-7(6H)-one Step 1:

A sealed tube was charged with the compound I-7 (300 mg, 1.1 mmol), the compound I-3A (409 mg, 1.32 mmol), EtOH (2 mL), and DIPEA (0.29 mL, 1.65 mmol). The reaction mixture was heated to reflux for 2 h, concentrated under reduced pressure and the residue was diluted with EtOAc. The organic layer was washed with water, dried over $Na_2SO_4$, and concentrated under reduced pressure. The residue was purified by column chromatography to afford the desired product (427 mg) as a white solid.

LC-MS (ESI, m/z)=464.2 $(M+H^+)$.

Step 2:

To a solution of the compound (427 mg, 0.921 mmol) obtained in Step 1 in AcOH (6 mL) and 35% HCl (1.5 mL) was heated to 60° C. to 70° C. for 2 h. The mixture was concentrated under reduced pressure and the residue adjusted to pH 5 to pH 6 by dropwise addition of 2 N NaOH. The precipitate was filtered and purified by column chromatography to afford the desired product (307 mg) as a white solid.

LC-MS (ESI, m/z)=422.1 $(M+H^+)$.

Example 3: 5-(4-(4-(Benzyloxy)-2,6-difluorophenyl)piperazin-1-yl)-3-methyl-3H-[1,2,3]triazolo[4,5-d]pyrimidin-7(6H)-one Following the general procedure of Example 1, the desired product was afforded using the previously obtained amine (I-3E).

LC-MS (ESI, m/z)=454.4 $(M+H^+)$.

Example 4: 5-(4-(2,6-Difluoro-4-(2-morpholinoethoxy)phenyl)piperazin-1-yl)-3-methyl-3H-[1,2,3] triazolo[4,5-d]pyrimidin-7(6H)-one Following the general procedure of Example 1, the desired product was afforded using the previously obtained amine (I-3F).

LC-MS (ESI, m/z)=477.5 $(M+H^+)$.

Example 5

5-(4-(2,6-Difluoro-4-(2-(piperidin-1-yl)ethoxy)phenyl)piperazin-1-yl)-3-methyl-3H-[1,2,3]triazolo[4,5-d]pyrimidin-7(6H)-one Following the general procedure of Example 1, the desired product was afforded using the previously obtained amine (I-3B).

LC-MS (ESI, m/z)=475.5 $(M+H^+)$.

Example 6

5-(4-(4-(2-(Dimethylamino)ethoxy)-2,6-difluorophenyl)piperazin-1-yl)-3-methyl-3H-[1,2,3]triazolo[4,5-d]pyrimidin-7(6H)-one Following the general procedure of Example 1, the desired product was afforded using the previously obtained amine (I-3G).

LC-MS (ESI, m/z)=435.1 $(M+H^+)$.

Example 7: 5-(4-(2,6-Difluoro-4-(2-hydroxyethoxy) phenyl)piperazin-1-yl)-3-methyl-3H-[1,2,3]triazolo [4,5-d]pyrimidin-7(6H)-one To a microwave reaction vial were added the compound I-7, (1-(4-(2-(benzyloxy)ethoxy)-2,6-difluorophenyl)piperazine hydrochloride prepared using a similar method to that described in Preparation Example 3.6, DIPEA, and isopropyl alcohol (2 mL). The reaction mixture was heated at 150° C. under microwave heating condition for 30 min. The mixture was concentrated under reduced pressure and the residue was purified by column chromatography. After sequential deprotection of the isopropyl group in the same manner as described in Step 2 of Example 2 and the O-benzyl group via catalyst hydrogenation as described in Preparation Example 3.3 the desired product was afforded.

LC-MS (ESI, m/z)=408.1 $(M+H^+)$.

Example 8: 2-(3,5-Difluoro-4-(4-(3-methyl-7-oxo-6, 7-dihydro-3H-[1,2,3]triazolo[4,5-d]pyrimidin-5-yl) piperazin-1-yl)phenoxy)ethyl acetate The desired product was afforded as a byproduct during the deprotection step in Example 7.

LC-MS (ESI, m/z)=450.1 $(M+H^+)$.

Example 9: 5-(4-(2,6-Difluoro-4-isopropoxyphenyl) piperazin-1-yl)-3-methyl-3H-[1,2,3]triazolo[4,5-d] pyrimidin-7(6H)-one Following the general procedure of Example 1, the desired product was afforded using the previously obtained amine (I-3C).

LC-MS (ESI, m/z)=406.1 $(M+H^+)$.

Example 10: (R)-2-(3,5-difluoro-4-(4-(3-methyl-7-oxo-6,7-dihydro-3H-[1,2,3]triazolo[4,5-d]pyrimidin-5-yl)piperazin-1-yl)phenoxy)ethyl2-aminopropanoate hydrochloride The compound obtained in Example 7 was coupled with Boc-D-Ala-OH in the presence of a coupling reagent (PyBOP) followed by Boc deprotection to afford the desired product.

LC-MS (ESI, m/z)=479.2 $(M+H^+)$.

Example 11: (S)-2-(3,5-difluoro-4-(4-(3-methyl-7-oxo-6,7-dihydro-3H-[1,2,3]triazolo[4,5-d]pyrimidin-5-yl)piperazin-1-yl)phenoxy)ethyl2-aminopropanoate hydrochloride The desired product was synthesized in the same manner as described in Example 10 using Boc-L-Ala-OH.
LC-MS (ESI, m/z)=479.2 (M+H$^+$).

Example 12

5-(4-(4-(2,3-Dihydroxypropoxy)-2,6-difluorophenyl)piperazin-1-yl)-3-methyl-3H-[1,2,3]triazolo[4,5-d]pyrimidin-7(6H)-one Following the general procedure of Step 1 in Example 2, the intermediate compound was afforded using the previously obtained amine (I-3E). The resulting compound was hydrogenated using Pd/C to provide the phenolic compound, which was further reacted with (2,2-dimethyl-1,3-dioxolan-4-yl)methyl 4-methylbenzenesulfonate to afford the protected target compound.

After simultaneous removal of the isopropyl and dioxolanyl groups using a method similar to that described in Step 2 of Example 2, the desired product was afforded.
LC-MS (ESI, m/z)=438.1 (M+H$^+$).

Example 13: 5-(4-(2,6-Difluoro-4-(morpholinomethyl)phenyl)piperazin-1-yl)-3-methyl-3H-[1,2,3]triazolo[4,5-d]pyrimidin-7(6H)-one The desired product was synthesized in the same manner as described in Example 2 using the amine synthesized following a similar method to that described in Preparation Example 4.
LC-MS (ESI, m/z)=447.2 (M+H$^+$).

Example 14

5-(4-(2,6-Difluoro-4-((4-methylpiperazin-1-yl)methyl)phenyl)piperazin-1-yl)-3-methyl-3H-[1,2,3]triazolo[4,5-d]pyrimidin-7(6H)-one The desired product was synthesized in the same manner as described in Example 2 using the amine synthesized following a similar method to that described in Preparation Example 4.
LC-MS (ESI, m/z)=460.2 (M+H$^+$).

Example 15: 5-(4-(2,6-Difluoro-4-(oxetan-3-yloxy)phenyl)piperazin-1-yl)-3-methyl-3H-[1,2,3]triazolo[4,5-d]pyrimidin-7(6H)-one Following the general procedure of Example 2, the desired product was afforded using the previously obtained amine (I-3E).
LC-MS (ESI, m/z)=420.1 (M+H$^+$).

Example 16

5-(4-(4-(1-Chloro-3-hydroxypropan-2-yloxy)-2,6-difluorophenyl)piperazin-1-yl)-3-methyl-3H-[1,2,3]triazolo[4,5-d]pyrimidin-7(6H)-one The desired product was synthesized in the same manner as described in Example 15 using the amine produced as a byproduct during the synthesis of the compound I-3D in Preparation Example 3.
LC-MS (ESI, m/z)=456.1 (M+H$^+$).

Example 17: 5-(4-(2,6-Difluoro-4-(1-hydroxyethyl)phenyl)piperazin-1-yl)-3-methyl-3H-[1,2,3]triazolo[4,5-d]pyrimidin-7(6H)-one Following the general procedure of Example 2, the desired product was synthesized using the compound obtained in Preparation Example 5.
LC-MS (ESI, m/z)=392.1 (M+H$^+$).

Example 18: 5-(4-(2,6-Difluoro-4-(1-methoxyethyl)phenyl)piperazin-1-yl)-3-methyl-3H-[1,2,3]triazolo[4,5-d]pyrimidin-7(6H)-one Following the general procedure of Example 2, the desired product was synthesized using the compound obtained in Preparation Example 6.
LC-MS (ESI, m/z)=406.2 (M+H$^+$).

Example 19: 6-(3,5-Difluoro-4-(4-(3-methyl-7-oxo-6,7-dihydro-3H-[1,2,3]triazolo[4,5-d]pyrimidin-5-yl)piperazin-1-yl)phenoxy)hexanoic acid The compound obtained in Preparation Example 3.3 was alkylated using ethyl 5-bromopentanoate and the Boc group was removed. The resulting amine compound reacted with the compound I-7 following a similar method to that described in Example 2 to afford the desired product.
LC-MS (ESI, m/z)=478.2 (M+H$^+$).

Example 20

5-(4-(2,6-Difluoro-4-(((2-methoxyethyl)(methyl)amino)methyl)phenyl)piperazin-1-yl)-3-methyl-3H-[1,2,3]triazolo[4,5-d]pyrimidin-7(6H)-one Following the general procedure of Example 2, the desired product was afforded using the amine compound obtained in Preparation Example 4.
LC-MS (ESI, m/z)=449.2 (M+H$^+$).

Example 21: 5-(4-(2,6-Difluorophenyl)piperazin-1-yl)-3-methyl-3H-[1,2,3]triazolo[4,5-d]pyrimidin-7(6H)-one Following the general procedure of Example 1, the desired product was afforded using the amine prepared in the same manner as described in Preparation Examples 3.2 and 3.5.
LC-MS (ESI, m/z)=348.1 (M+H$^+$).

Example 22: 3-Methyl-5-(4-(2,4,6-trifluorophenyl)piperazin-1-yl)-3H-[1,2,3]triazolo[4,5-d]pyrimidin-7(6H)-one Following the general procedure of Example 1, the desired product was afforded using the amine prepared in the same manner as described in Preparation Examples 3.2 and 3.5.
LC-MS (ESI, m/z)=366.3 (M+H$^+$).

Example 23: 5-(4-(4-(1,2-Dihydroxyethyl)-2,6-difluorophenyl)piperazin-1-yl)-3-methyl-3H-[1,2,3]triazolo[4,5-d]pyrimidin-7(6H)-one Following the general procedure of Example 1, the desired product was afforded using the amine prepared in Preparation Example 10 (B).
LC-MS (ESI, m/z)=408.3 (M+H$^+$).

Example 24: 5-(4-(4-(2,3-Dihydroxypropyl)-2,6-difluorophenyl)piperazin-1-yl)-3-methyl-3H-[1,2,3]triazolo[4,5-d]pyrimidin-7(6H)-one Following the general procedure of Example 1, the desired product was afforded using the amine prepared in Preparation Example 9 (A).
LC-MS (ESI, m/z)=422.4 (M+H$^+$).

Example 25: 5-(4-(2,6-Difluoro-4-(2-methoxyethoxy)phenyl)-4-hydroxypiperidin-1-yl)-3-methyl-3H-[1,2,3]triazolo[4,5-d]pyrimidin-7(6H)-one Following the general procedure of Example 1, the desired product was afforded using the amine prepared in Preparation Example 7.
LC-MS (ESI, m/z)=437.3 (M+H$^+$).

Example 26: 5-(4-(1H-tetrazol-5-yl)piperidin-1-yl)-3-methyl-3H-[1,2,3]triazolo[4,5-d]pyrimidin-7(6H)-one Following the general procedure of Example 1, the desired product was afforded using the amine prepared in Preparation Example 8.
LC-MS (ESI, m/z)=303.1 (M+H$^+$).

Example 27: 5-(4-(2,6-Difluoro-4-(2-methoxyethylamino)phenyl)piperazin-1-yl)-3-methyl-3H-[1,2,3]triazolo[4,5-d]pyrimidin-7(6H)-one Following the general procedure of Example 1, the desired product was afforded using the amine prepared in Preparation Example 11.
LC-MS (ESI, m/z)=421.3 (M+H$^+$).

Example 28: 5-(4-(2,6-Difluoro-4-vinylphenyl)piperazin-1-yl)-3-methyl-3H-[1,2,3]triazolo[4,5-d]pyrimidin-7(6H)-one Following the general procedure of Example 1, the desired product was afforded using the amine which was prepared by the Boc removal from the compound obtained in Preparation Example 10.1.
LC-MS (ESI, m/z)=374.3 (M+H$^+$).

Example 29: 3-Methyl-5-(4-(1-methyl-1H-tetrazol-5-yl)piperidin-1-yl)-3H-[1,2,3]triazolo[4,5-d]pyrimidin-7(6H)-one After adding Cs$_2$CO$_3$, MeI and THF to the compound obtained in Preparation Example 8.1, the reaction mixture was heated to 80° C. for 2 h. The mixture was concentrated under reduced pressure and the residue was purified by column chromatography to provide the Boc-protected amine. After the removal of the Boc group, the resulting amine was reacted with the compound I-7 in the same manner as described in Example 2 to afford the desired product.
LC-MS (ESI, m/z)=317.1 (M+H$^+$).

Example 30: 3-Methyl-5-(4-(2-methyl-2H-tetrazol-5-yl)piperidin-1-yl)-3H-[1,2,3]triazolo[4,5-d]pyrimidin-7(6H)-one The compound obtained in Preparation Example 8.1, was reacted with the compound I-7 in the same manner as described in Example 29 to afford the desired product.
LC-MS (ESI, m/z)=317.1 (M+H$^+$).

Example 31

5-(4-(2,6-Difluoro-4-(2-(pyrrolidin-1-yl)ethoxy)phenyl)piperazin-1-yl)-3-methyl-3H-[1,2,3]triazolo[4,5-d]pyrimidin-7(6H)-one Following the general procedure of Example 2, the desired product was afforded using the amine prepared in Preparation Example 12.10.
LC-MS (ESI, m/z)=461.2 (M+H$^+$).

Example 32

5-(4-(2,6-Difluoro-4-(2-(4-methylpiperazin-1-yl)ethoxy)phenyl)piperazin-1-yl)-3-methyl-3H-[1,2,3]triazolo[4,5-d]pyrimidin-7(6H)-one Following the general procedure of Example 2, the desired product was afforded using the amine (I-12D) prepared in Preparation Example 12.9.
LC-MS (ESI, m/z)=490.2 (M+H$^+$).

Example 33

5-(4-(2,6-Difluoro-4-(3-(piperidin-1-yl)propoxy)phenyl)piperazin-1-yl)-3-methyl-3H-[1,2,3]triazolo[4,5-d]pyrimidin-7(6H)-one tert-Butyl 4-(2,6-difluoro-4-(2-hydroxypropoxy)phenyl)piperazine-1-carboxylate was subjected to tosylation (TsCl, TEA, DMAP and CH$_2$Cl$_2$), substitution with piperidine (piperidine, K$_2$CO$_3$ and DMF), and then deprotection of the Boc group to provide the desired amine. The resulting amine was reacted with the compound I-7 in the same manner as described in Example 2 to afford the desired product.
LC-MS (ESI, m/z)=489.3 (M+H$^+$).

Example 34

5-(4-(4-(Bis(2-methoxyethyl)amino)-2,6-difluorophenyl)piperazin-1-yl)-3-methyl-3H-[1,2,3]triazolo[4,5-d]pyrimidin-7(6H)-one Following the general procedure of Example 1, the desired product was afforded using the amine which was prepared as a byproduct during the reaction in Preparation Example 11.
LC-MS (ESI, m/z)=479.2 (M+H$^+$).

Example 35: 5-(4-(2,6-Difluoro-4-(2-oxo-2-(piperidin-1-yl)ethoxy)phenyl) piperazin-1-yl)-3-methyl-3H-[1,2,3]triazolo[4,5-d]pyrimidin-7(6H)-one Following the general procedure of Example 2, the desired product was afforded using the amine (I-12B) prepared in Preparation Example 12.4.
LC-MS (ESI, m/z)=489.2 (M+H$^+$).

Example 36: 5-(4-(2,6-Difluoro-4-(2-oxo-2-(pyrrolidin-1-yl)ethoxy)phenyl) piperazin-1-yl)-3-methyl-3H-[1,2,3]triazolo[4,5-d]pyrimidin-7(6H)-one Following the general procedure of Example 2, the desired product was afforded using the amine (I-12A) prepared in Preparation Example 12.2.
LC-MS (ESI, m/z)=475.2 (M+H$^+$).

Example 37: 5-(4-(4-(2-Aminoethoxy)-2,6-difluorophenyl)piperazin-1-yl)-3-methyl-3H-[1,2,3]triazolo[4,5-d]pyrimidin-7(6H)-one Step 1:

To a sealed tube was added the compound I-7, the compound I-12E (200 mg, 0.485 mmol), EtOH (1.72 mL), and DIPEA (0.180 mL, 1.032 mmol). The reaction mixture was heated to 60° C. to 65° C. for 16 h. After cooling down to rt, the mixture was concentrated under reduced pressure and the residue was diluted with EtOAc. The organic layer was washed with brine, dried over $Na_2SO_4$, filtered, and concentrated under reduced pressure. The residue was purified by column chromatography to afford the desired product (211 mg) as a yellow oil.

LC-MS (ESI, m/z)=475.2 (M+H$^+$).

Step 2:

To a solution of the compound (210 mg, 0.443 mmol) obtained in Step 1 in MeOH (1.5 mL) was added 10% Pd/C (42 mg) at rt. After stirring at rt for 2 h under hydrogen gas, the mixture was filtered through a Celite pad. The filtrate was concentrated under reduced pressure to afford the desired product (99 mg) as a white solid.

LC-MS (ESI, m/z)=449.2 (M+H$^+$).

Step 3:

To a solution of the compound (97 mg, 0.216 mmol) obtained in Step 2 in AcOH (2 mL) and 35% HCl solution (0.5 mL) was heated to 60° C. to 70° C. for 2 h. The mixture was concentrated under reduced pressure and the residue was adjusted to pH 5 to pH 6 by adding 2 N NaOH dropwise. The precipitate was filtered with $CH_2Cl_2$ to afford the desired product (59 mg) as a white solid.

LC-MS (ESI, m/z)=407.2 (M+H$^+$).

Example 38: 5-(4-(2,6-Difluoro-4-(2-(4-methyl-2-oxopiperazin-1-yl)ethoxy)phenyl)piperazin-1-yl)-3-methyl-3H-[1,2,3]triazolo[4,5-d]pyrimidin-7(6H)-one Following the general procedure of Example 2, the desired product was afforded using the amine (I-12F) prepared in Preparation Example 12.12.

LC-MS (ESI, m/z)=504.3 (M+H$^+$).

Example 39: 5-(4-(4-(2-(4-Aminopiperidin-1-yl)ethoxy)-2,6-difluorophenyl)piperazin-1-yl)-3-methyl-3H-[1,2,3]triazolo[4,5-d]pyrimidin-7(6H)-one Following a procedure similar to that described in Example 37, the desired product was afforded using the amine (I-12G) prepared in Preparation Example 12.13.

LC-MS (ESI, m/z)=490.3 (M+H$^+$).

Example 40: 5-(4-(2,6-Difluoro-4-(3-methoxypropyl)phenyl)piperazin-1-yl)-3-methyl-3H-[1,2,3]triazolo[4,5-d]pyrimidin-7(6H)-one Following the general procedure of Example 2, the desired product was afforded using the amine (I-13A) prepared in Preparation Example 13.2.

LC-MS (ESI, m/z)=420.1 (M+H$^+$).

Example 41: 5-(4-(2,6-Difluoro-4-(2-(3-hydroxypyrrolidin-1-yl)ethoxy)phenyl)piperazin-1-yl)-3-methyl-3H-[1,2,3]triazolo[4,5-d]pyrimidin-7(6H)-one Following the general procedure of Example 2, the desired product was afforded using the previously obtained amine (I-14A).

LC-MS (ESI, m/z)=476.8 (M+H$^+$).

Example 42: 5-(4-(2,6-Difluoro-4-(2-(4-hydroxypiperidin-1-yl)ethoxy)phenyl)piperazin-1-yl)-3-methyl-3H-[1,2,3]triazolo[4,5-d]pyrimidin-7(6H)-one Following the general procedure of Example 2, the desired product was afforded using the previously obtained amine (I-14B).

LC-MS (ESI, m/z)=490.9 (M+H$^+$).

Example 43

5-(4-(2,6-Difluoro-4-(2-(4-hydroxy-4-methylpiperidin-1-yl)ethoxy)phenyl)piperazin-1-yl)-3-methyl-3H-[1,2,3]triazolo[4,5-d]pyrimidin-7(6H)-one Following the general procedure of Example 2, the desired product was afforded using the previously obtained amine (I-14C).

LC-MS (ESI, m/z)=504.7 (M+H$^+$).

Example 44

5-(4-(2,6-Difluoro-4-(2-methoxyethoxy)phenyl)-5,6-dihydropyridin-1(2H)-yl)-3-methyl-3H-[1,2,3]triazolo[4,5-d]pyrimidin-7(6H)-one Following the general procedure of Example 2, the desired product was afforded using the amine prepared in Preparation Example 7.2.

LC-MS (ESI, m/z)=419.2 (M+H$^+$).

Example 45: 5-(4-(2,6-Difluoro-4-(2-methoxyethoxy)phenyl)piperidin-1-yl)-3-methyl-3H-[1,2,3]triazolo[4,5-d]pyrimidin-7(6H)-one The desired product was afforded by Pd/C-catalyzed hydrogenation of the compound obtained in Example 44.

LC-MS (ESI, m/z)=421.2 (M+H$^+$).

Example 46

5-(4-(2,6-Difluoro-4-(2-(2-oxopiperidin-1-yl)ethoxy)phenyl)piperazin-1-yl)-3-methyl-3H-[1,2,3]triazolo[4,5-d]pyrimidin-7(6H)-one Following the general procedure of Example 2, the desired product was afforded using the amine prepared in Preparation Example 12.14.

LC-MS (ESI, m/z)=489.2 (M+H$^+$).

Example 47: 5-(4-(4-(2-Ethoxyethoxy)-2,6-difluorophenyl)piperazin-1-yl)-3-methyl-3H-[1,2,3]triazolo[4,5-d]pyrimidin-7(6H)-one Following the general procedure of Example 2, the desired product was afforded using 1-(4-(2-ethoxyethoxy)-2,6-difluorophenyl)piperazine hydrochloride.

LC-MS (ESI, m/z)=436.2 (M+H$^+$).

Example 48

5-(4-(4-(2-(cis-2,6-Dimethylpiperidin-1-yl)ethoxy)-2,6-difluorophenyl)piperazin-1-yl)-3-methyl-3H-[1,2,3]triazolo[4,5-d]pyrimidin-7(6H)-one Following the general procedure of Example 2, the desired product was afforded using the amine prepared in the same manner as described in Preparation Examples 3.4 and 3.5.
LC-MS (ESI, m/z)=502.9 (M+H$^+$).

Example 49

5-(4-(4-(2-(4,4-Difluoropiperidin-1-yl)ethoxy)-2,6-difluorophenyl)piperazin-1-yl)-3-methyl-3H-[1,2,3]triazolo[4,5-d]pyrimidin-7(6H)-one Following the general procedure of Example 2, the desired product was afforded using the amine prepared in the same manner as described in Preparation Examples 3.4 and 3.5.
LC-MS (ESI, m/z)=511.1 (M+H$^+$).

Example 50

5-(4-(4-(2-(Diethylamino)ethoxy)-2,6-difluorophenyl)piperazin-1-yl)-3-methyl-3H-[1,2,3]triazolo[4,5-d]pyrimidin-7(6H)-one Following the general procedure of Example 2, the desired product was afforded using the amine prepared in the same manner as described in Preparation Examples 3.4 and 3.5.
LC-MS (ESI, m/z)=462.9 (M+H$^+$).

Example 51

5-(4-(4-(2-(1H-imidazol-1-yl)ethoxy)-2,6-difluorophenyl)piperazin-1-yl)-3-methyl-3H-[1,2,3]triazolo[4,5-d]pyrimidin-7(6H)-one Following the general procedure of Example 2, the desired product was afforded using the amine prepared in the same manner as described in Preparation Examples 3.4 and 3.5.
LC-MS (ESI, m/z)=457.9 (M+H$^+$).

Example 52

5-(4-(2,6-Difluoro-4-((tetrahydrofuran-2-yl)methoxy)phenyl)piperazin-1-yl)-3-methyl-3H-[1,2,3]triazolo[4,5-d]pyrimidin-7(6H)-one Following the general procedure of Example 2, the desired product was afforded using the amine prepared in the same manner as described in Preparation Examples 3.4 and 3.5.
LC-MS (ESI, m/z)=448.1 (M+H$^+$).

Example 53: 6-(4-(2,6-Difluoro-4-(2-methoxyethoxy)phenyl)piperazin-1-yl)-1-methyl-1H[1,2,3]triazolo[4,5-c]pyridin-4(5H)-one Step 1:
To a mixture of the compound I-15 (195 mg, 0.710 mmol), the amine I-3A (195 mg, 0.852 mmol), sodium tert-butoxide (204.6 mg, 2.130 mmol), BINAP (44.2 mg, 0.035 mmol), Pd$_2$(dba)$_3$ (32.5 mg, 0.133 mmol) and 1,4-dioxane was added to a sealed tube and heated to 100° C. to 110° C. for 5.5 h. After cooling down to rt, the mixture was filtered through a Celite pad. The filtrate was diluted with EtOAc and washed with water, dried over Na$_2$SO$_4$. The organic layer was filtered, and concentrated under reduced pressure. The residue was purified by column chromatography to afford the desired product (160 mg) as a yellow oil.
LC-MS (ESI, m/z)=564.3 (M+H$^+$).
Step 2:
To a solution of the compound (104 mg, 0.204 mmol) obtained in Step 1 in MeOH (0.68 mL) and CH$_2$Cl$_2$ (0.2 mL) was added 10% Pd/C (20 mg) at rt. After stirring at rt for 1 h under hydrogen gas, the mixture was filtered through a Celite pad. The filtrate was concentrated under reduced pressure and the residue was purified by column chromatography to afford the desired product (36.7 mg) as a white solid.
LC-MS (ESI, m/z)=474.3 (M+H$^+$).

Example 54: 6-(4-(2,6-Difluoro-4-(2-morpholinoethoxy)phenyl)piperazin-1-yl)-1-methyl-1H-[1,2,3]triazolo[4,5-c]pyridin-4(5H)-one Following the general procedure of Example 53, the desired product was afforded using the amine (I-3F) prepared in Preparation Example 3.10.
LC-MS (ESI, m/z)=476.3 (M+H$^+$).

Example 55

6-(4-(2,6-Difluoro-4-(2-(piperidin-1-yl)ethoxy)phenyl)piperazin-1-yl)-1-methyl-1H-[1,2,3]triazolo[4,5-c]pyridin-4(5H)-one Following the general procedure of Example 53, the desired product was afforded using the amine (I-3B) prepared in Preparation Example 3.4.
LC-MS (ESI, m/z)=474.3 (M+H$^+$).

Example 56

6-(4-(4-(2-(Dimethylamino)ethoxy)-2,6-difluorophenyl)piperazin-1-yl)-1-methyl-1H-[1,2,3]triazolo[4,5-c]pyridin-4(5H)-one Following the general procedure of Example 53, the desired product was afforded using the amine (I-3G) prepared in Preparation Example 3.11.
LC-MS (ESI, m/z)=434.2 (M+H$^+$).

Example 57: 6-(4-(2,6-Difluoro-4-(2-hydroxyethoxy)phenyl)piperazin-1-yl)-1-methyl-1H[1,2,3]triazolo[4,5-c]pyridin-4(5H)-one Following the general procedure of Example 53, the desired product was afforded using (1-(4-(2-(benzyl)ethoxy)-2,6-difluorophenyl)piperazine hydrochloride synthesized in the same manner as described in Preparation Example 3.6.
LC-MS (ESI, m/z)=407.1 (M+H$^+$).

Example 58: (S)-2-(3,5-difluoro-4-(4-(1-methyl-4-oxo-4,5-dihydro-1H-[1,2,3]triazolo[4,5-c]pyridin-6-yl)piperazin-1-yl)phenoxy)ethyl2-aminopropanoate hydrochloride The compound obtained in Example 52 was coupled with Boc-L-Ala-OH in the presence of a coupling reagent (PyBOP) followed by Boc deprotection to afford the desired product.
LC-MS (ESI, m/z)=478.2 (M+H$^+$).

Example 59

6-(4-(4-(2,3-Dihydroxypropoxy)-2,6-difluorophenyl)piperazin-1-yl)-1-methyl-1H-[1,2,3]triazolo[4,5-c]pyridin-4(5H)-one The compound I-15 was reacted with 1-(4-(tert-butyldimethylsilyloxy)-2,6-difluorophenyl)piperazine in the same manner as described in Step 1 of Example 53, followed by TBS deprotection and alkylation with (2,2-dimethyl-1,3-dioxolan-4-yl)methyl 4-methylbenzenesulfonate to afford the corresponding alkylated compound. The resulting compound was treated with TFA to remove the protecting group and further reacted in the same manner as described in Step 2 of Example 53 to afford the desired product.
LC-MS (ESI, m/z)=473.2 (M+H$^+$).

Example 60: 6-(4-(2,6-Difluoro-4-(morpholinomethyl)phenyl)piperazin-1-yl)-1-methyl-1H-[1,2,3]triazolo[4,5-c]pyridin-4(5H)-one Following the general procedure of Example 53, the desired product was afforded using the amine prepared in Preparation Example 4.
LC-MS (ESI, m/z)=446.2 (M+H$^+$).

Example 61: 6-(4-(2,6-Difluoro-4-((4-methylpiperazin-1-yl)methyl)phenyl)piperazin-1-yl)-1-methyl-1H-[1,2,3]triazolo[4,5-c]pyridin-4(5H)-one Following the general procedure of Example 53, the desired product was afforded using the amine prepared in the same manner as described in Preparation Example 4.
LC-MS (ESI, m/z)=459.2 (M+H$^+$).

Example 62: 6-(4-(2,6-Difluoro-4-(oxetan-3-yloxy)phenyl)piperazin-1-yl)-1-methyl-1H-[1,2,3]triazolo[4,5-c]pyridin-4(5H)-one Following the general procedure of Example 53, the desired product was afforded using the amine (I-3D) prepared in Preparation Example 3.8.
LC-MS (ESI, m/z)=419.1 (M+H$^+$).

Example 63: 6-(4-(2,6-Difluoro-4-(1-hydroxyethyl)phenyl)piperazin-1-yl)-1-methyl-1H[1,2,3]triazolo[4,5-c]pyridin-4(5H)-one The compound obtained in Preparation Example 5.1 was subjected to O-benzylation, followed by Boc deprotection to provide the desired amine product. The resulting amine was reacted with the compound I-15 in the same manner as described in Example 53 to afford the desired product.
LC-MS (ESI, m/z)=391.1 (M+H$^+$).

Example 64: 6-(4-(2,6-Difluoro-4-(1-methoxyethyl)phenyl)piperazin-1-yl)-1-methyl-1H[1,2,3]triazolo[4,5-c]pyridin-4(5H)-one Following the general procedure of Example 53, the desired product was afforded using the amine prepared in Preparation Example 6.
LC-MS (ESI, m/z)=405.1 (M+H$^+$).

Example 65: 6-(4-(2,6-Difluoro-4-(((2-methoxyethyl)(methyl)amino)methyl)phenyl)piperazin-1-yl)-1-methyl-1H-[1,2,3]triazolo[4,5-c]pyridin-4(5H)-one Following the general procedure of Example 53, the desired product was afforded using the amine prepared in the same manner as described in Preparation Example 4.
LC-MS (ESI, m/z)=448.2 (M+H$^+$).

Example 66: 1-Methyl-6-(4-(2-methyl-2H-tetrazol-5-yl)piperidin-1-yl)-1H-[1,2,3]triazolo[4,5-c]pyridin-4(5H)-one Cs$_2$CO$_3$, MeI and THF were added to the compound obtained in Preparation Example 8.1, the resulting mixture was heated to 80° C. for 2 h. The mixture was concentrated under reduced pressure and the residue was purified by column chromatography to provide the Boc-protected amine. After the removal of the Boc group, the resulting amine was reacted with the compound I-15 in the same manner as described in Example 53 to afford the desired product.
LC-MS (ESI, m/z)=316.1 (M+H$^+$).

Example 67

6-(4-(2,6-Difluoro-4-(2-(pyrrolidin-1-yl)ethoxy)phenyl)piperazin-1-yl)-1-methyl-1H-[1,2,3]triazolo[4,5-c]pyridin-4(5H)-one Following the general procedure of Example 53, the desired product was afforded using the amine (I-12C) prepared in Preparation Example 12.10.
LC-MS (ESI, m/z)=460.2 (M+H$^+$).

Example 68: 6-(4-(2,6-Difluoro-4-(2-(4-methylpiperazin-1-yl)ethoxy)phenyl)piperazin-1-yl)-1-methyl-1H-[1,2,3]triazolo[4,5-c]pyridin-4(5H)-one Following the general procedure of Example 53, the desired product was afforded using the amine (I-12D) prepared in Preparation Example 12.9.
LC-MS (ESI, m/z)=489.3 (M+H$^+$).

Example 69

6-(4-(2,6-Difluoro-4-(3-(piperidin-1-yl)propoxy)phenyl)piperazin-1-yl)-1-methyl-1H-[1,2,3]triazolo[4,5-c]pyridin-4(5H)-one Tert-Butyl 4-(2,6-difluoro-4-(2-hydroxypropoxy)phenyl)piperazine-1-carboxylate compound was subjected to tosylation (TsCl, TEA, DMAP and CH$_2$Cl$_2$), substitution with piperidine (piperidine, K$_2$CO$_3$ and DMF), and then deprotection of the Boc group to provide the desired amine. The resulting amine compound was reacted with the compound I-15 in the same manner as described in Example 53 to afford the desired product.

LC-MS (ESI, m/z)=488.3 (M+H$^+$).

Example 70: 6-(4-(2,6-Difluoro-4-(2-oxo-2-(pyrrolidin-1-yl)ethoxy)phenyl)piperazin-1-yl)-1-methyl-1H-[1,2,3]triazolo[4,5-c]pyridin-4(5H)-one Following the general procedure of Example 53, the desired product was afforded using the amine (I-12A) prepared in Preparation Example 12.2.

LC-MS (ESI, m/z)=474.2 (M+H$^+$).

Example 71: 6-(4-(4-(2-Aminoethoxy)-2,6-difluorophenyl)piperazin-1-yl)-1-methyl-1H-[1,2,3]triazolo[4,5-c]pyridin-4(5H)-one Following the general procedure of Example 53, the desired product was afforded using the amine (I-12E) prepared in Preparation Example 12.11.

LC-MS (ESI, m/z)=406.2 (M+H$^+$).

Example 72: 6-(4-(4-(2-(4-Aminopiperidin-1-yl)ethoxy)-2,6-difluorophenyl)piperazin-1-yl)-1-methyl-1H-[1,2,3]triazolo[4,5-c]pyridin-4(5H)-one Following the general procedure of Example 53, the desired product was afforded using the amine (I-12G) prepared in Preparation Example 12.13.

LC-MS (ESI, m/z)=489.3 (M+H$^+$).

Example 73: 5-(4-(2,6-Difluoro-4-(2-methoxyethoxy)phenyl)piperazin-1-yl)-3H-[1,2,3]triazolo[4,5-d]pyrimidin-7(6H)-one Step 1:

To a solution of 2,6-dichloropyrimidin-4-amine (1 g, 6.098 mmol) and 4-dimethylaminopyridine (149 mg, 1.220 mmol) in CH$_2$Cl$_2$ (12 mL) was added ditert-butyl dicarbonate (2.66 g, 12.196 mmol). After stirring at rt for 24 h, the reaction mixture was concentrated and the residue was diluted with EtOAc, washed with water and dried over Na$_2$SO$_4$. The organic layer was concentrated to afford the residue which was used to the next reaction without further purification.

To a mixture of NaH (330 mg, 6.744 mmol, 55% in mineral oil) in DMF (10 mL) was added dropwise benzylalcohol (0.7 mL, 6.744 mmol) at 0° C. for 30 min. A solution of the crude product (2.047 g, 5.620 mmol) in DMF (6 mL) was added dropwise to the reaction mixture at 0° C. for 10 min. After stirring at rt for 1 h, the reaction mixture was diluted with EtOAc, washed with brine and dried over Na$_2$SO$_4$. The organic layer was filtered, concentrated under reduced pressure and the residue was purified by column chromatography to afford the desired product (1.494 g, 3.427 mmol) as a yellow oil.

LC-MS (ESI, m/z)=436.1 (M+H$^+$).

Step 2:

A mixture of the compound (1.42 g, 3.258 mmol) obtained in Step 1, the compound I-3A (1.21 g, 3.910 mmol), sodium tert-butoxide (626 mg, 6.516 mmol), BINAP (203 mg, 0.326 mmol) and Pd$_2$(dba)$_3$ (149 mg, 0.163 mmol) in 1,4-dioxane was added to a sealed tube and heated to 100° C. to 110° C. for 17 h. After cooling down to rt, the mixture was filtered through a Celite pad and the residue was diluted with EtOAc. The organic layer was washed with water, dried over Na$_2$SO$_4$, and concentrated under reduced pressure. The residue was purified by column chromatography to afford the desired product (371 mg, 0.654 mmol) as a yellow oil.

LC-MS (ESI, m/z)=572.3 (M+H$^+$).

Step 3:

To a solution of tert-butyl 6-(benzyloxy)-2-(4-(2,6-difluoro-4-(2-methoxyethoxy)phenyl)piperazin-1-yl)pyrimidin-4-ylcarbamate (374 mg, 0.654 mmol) in MeOH (2.2 mL) was added 10% Pd/C. After stirring at rt for 5.5 h under hydrogen gas, the reaction mixture was filtered through a Celite pad. The filtrate was concentrated, and desired product was obtained as a white solid (230 mg, 0.478 mmol) which was used to the next reaction without further purification.

LC-MS (ESI, m/z)=482.2 (M+H$^+$).

Step 4:

The desired product (154 mg) was afforded as an orange solid from the compound (210 mg) obtained in Step 3 following in the same manner as described in Preparation Example 3.5.

LC-MS (ESI, m/z)=382.1 (M+H$^+$).

Step 5:

The desired product (145 mg) was afforded as a brown solid from the compound (154 mg) obtained in Step 4 following the same manner as described in the Preparation Example 1.2.

LC-MS (ESI, m/z)=411.1 (M+H$^+$).

Step 6:

The desired product (21.7 mg) was afforded as a yellow solid from the compound (145 mg) obtained in Step 5 following the same manner as described in the Preparation Example 1.3.

LC-MS (ESI, m/z)=408.2 (M+H$^+$).

Example 74: Analysis of Activity of Tankyrase 1

Activities of novel compounds synthesized according to Examples 1 to 72 against tankyrase 1 were analyzed using a Trevigen kit (Cat. No. 4700-096-K). Poly PAR histone protein-coated 96-well plate, anti-PAR monoclonal antibody and goat anti-mouse IgG-HRP were used for measurement of absorbance by ELISA method. Specifically, 20× I-PAR assay buffer was diluted to 1× by adding water, and 50 µL of the diluted buffer was added to each well of the 96-well plate followed by reacting at rt for 30 min. Then, the supernatant was completely removed from each well and 10 µL of 1× I-PAR assay buffer and 15 µL of assay substrate were added to each well along with 1 µL of a 50× solution of inhibitors to be tested, which were the compounds obtained in the Examples 1 to 72. 10 mUnits/µL of tankyrase 1 enzyme was diluted 50-fold with 1× I-PAR assay buffer and 25 µL of the diluted enzyme was added to each well and reacted while stirring at rt for 30 min. One without any compound of the present invention was used as a positive control and another containing 1× I-PAR assay buffer with the same volume instead of tankyrase 1 enzyme was used as a negative control. Upon completion of the reaction, 200 µL of PBSX, which was prepared by adding 0.1% triton X-100 to PBS, was added and removed and this washing process was repeated twice. Washing was repeated twice more using PBS in the same manner. 5× antibody diluent was diluted with distilled water to 1× concentration, 50 µL of the diluted goat anti-mouse IgG-HRP to 1/2000 was added to each well and reacted while stirring at rt for 30 min. Washes were carried out twice using PBSX and PBS, respectively. After adding 50 µL of TACS-sapphire to each well of the plate, the plate was blocked from light to react for 10 min to 15 min and the color of the reaction solution turned blue. To stop the reaction, 50 µL of 0.2N HCl was added to turn the solution yellow. Finally, the absorbance of the resulting solution was measured at 450 nm.

TABLE 1

| Comp. | R group | IUPAC name | TNKS1 (IC$_{50}$) (nM) |
|---|---|---|---|
| | 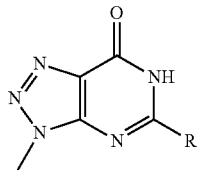 | | |
| 1 | 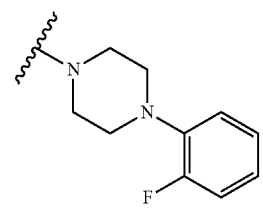 [SMILES: *N1CCN(c2ccccc2F)CC1] | 5-(4-(2-fluorophenyl)piperazin-1-yl)-3-methyl-3H-[1,2,3]triazolo[4,5-d]pyrimidin-7(6H)-one | 66.74 |
| 2 | 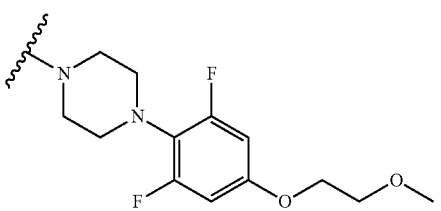 [SMILES: *N1CCN(c2c(F)cc(OCCOC)cc2F)CC1] | 5-(4-(2,6-difluoro-4-(2-methoxyethoxy)phenyl)piperazin-1-yl)-3-methyl-3H-[1,2,3]triazolo[4,5-d]pyrimidin-7(6H)-one | 29.94 |
| 3 | 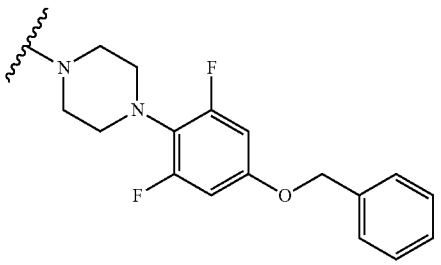 [SMILES: *N1CCN(c2c(F)cc(OCc3ccccc3)cc2F)CC1] | 5-(4-(4-(benzyloxy)-2,6-difluorophenyl)piperazin-1-yl)-3-methyl-3H-[1,2,3]triazolo[4,5-d]pyrimidin-7(6H)-one | 207 |
| 4 | 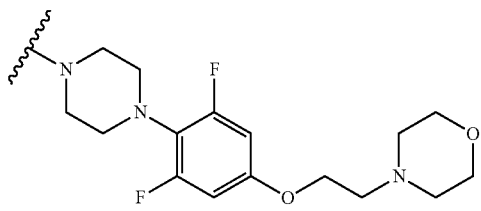 [SMILES: *N1CCN(c2c(F)cc(OCCN3CCOCC3)cc2F)CC1] | 5-(4-(2,6-difluoro-4-(2-morpholinoethoxy)phenyl)piperazin-1-yl)-3-methyl-3H-[1,2,3]triazolo[4,5-d]pyrimidin-7(6H)-one | 38.57 |
| 5 | 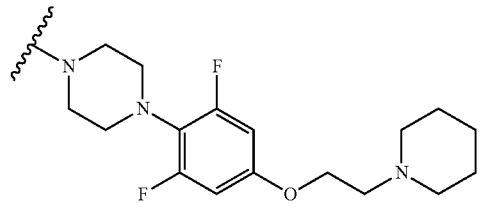 [SMILES: *N1CCN(c2c(F)cc(OCCN3CCCCC3)cc2F)CC1] | 5-(4-(2,6-difluoro-4-(2-(piperidin-1-yl)ethoxy)phenyl)piperazin-1-yl)-3-methyl-3H-[1,2,3]triazolo[4,5-d]pyrimidin-7(6H)-one | 14.25 |

TABLE 1-continued

| Comp. | R group | IUPAC name | TNKS1 (IC$_{50}$) (nM) |
|---|---|---|---|
| 6 | | 5-(4-(4-(2-(dimethylamino)ethoxy)-2,6-difluorophenyl)piperazin-1-yl)-3-methyl-3H-[1,2,3]triazolo[4,5-d]pyrimidin-7(6H)-one | 16.3 |
| 7 | | 5-(4-(2,6-difluoro-4-(2-hydroxyethoxy)phenyl)piperazin-1-yl)-3-methyl-3H-[1,2,3]triazolo[4,5-d]pyrimidin-7(6H)-one | 43.96 |
| 8 | | 2-(3,5-difluoro-4-(4-(3-methyl-7-oxo-6,7-dihydro-3H-[1,2,3]triazolo[4,5-d]pyrimidin-5-yl)piperazin-1-yl)phenoxy)ethyl acetate | 46.9 |
| 9 | | 5-(4-(2,6-difluoro-4-isopropoxyphenyl)piperazin-1-yl)-3-methyl-3H-[1,2,3]triazolo[4,5-d]pyrimidin-7(6H)-one | 60.91 |
| 10 | | (R)-2-(3,5-difluoro-4-(4-(3-methyl-7-oxo-6,7-dihydro-3H-[1,2,3]triazolo[4,5-d]pyrimidin-5-yl)piperazin-1-yl)phenoxy)ethoxy)-1-oxopropan-2-aminium chloride | 32.05 |
| 11 | | (S)-2-(3,5-difluoro-4-(4-(3-methyl-7-oxo-6,7-dihydro-3H-[1,2,3]triazolo[4,5-d]pyrimidin-5-yl)piperazin-1-yl)phenoxy)ethoxy)-1-oxopropan-2-aminium chloride | 14.54 |

TABLE 1-continued

| Comp. | R group | IUPAC name | TNKS1 (IC$_{50}$) (nM) |
|---|---|---|---|
| 12 | | 5-[4-(4-(2,3-dihydroxypropoxy)-2,6-difluorophenyl)piperazin-1-yl)-3-methyl-3H-[1,2,3]triazolo[4,5-d]pyrimidin-7(6H)-one | 12.94 |
| 13 | | 5-(4-(2,6-difluoro-4-(morpholinomethyl)phenyl)piperazin-1-yl)-3-methyl-3H-[1,2,3]triazolo[4,5-d]pyrimidin-7(6H)-one | 28.01 |
| 14 | | 5-(4-(2,6-difluoro-4-((4-methylpiperazin-1-yl)methyl)phenyl)piperazin-1-yl)-3-methyl-3H-[1,2,3]triazolo[4,5-d]pyrimidin-7(6H)-one | 41.49 |
| 15 | | 5-(4-(2,6-difluoro-4-(oxetan-3-yloxy)phenyl)piperazin-1-yl)-3-methyl-3H-[1,2,3]triazolo[4,5-d]pyrimidin-7(6H)-one | 24.7 |
| 16 | | 5-(4-(4-(1-chloro-3-hydroxypropan-2-yloxy)-2,6-difluorophenyl)piperazin-1-yl)-3-methyl-3H-[1,2,3]triazolo[4,5-d]pyrimidin-7(6H)-one | 28.58 |
| 17 | | 5-(4-(2,6-difluoro-4-(1-hydroxyethyl)phenyl)piperazin-1-yl)-3-methyl-3H-[1,2,3]triazolo[4,5-d]pyrimidin-7(6H)-one | 17.58 |

TABLE 1-continued

| Comp. | R group | IUPAC name | TNKS1 (IC$_{50}$) (nM) |
|---|---|---|---|
| 18 | 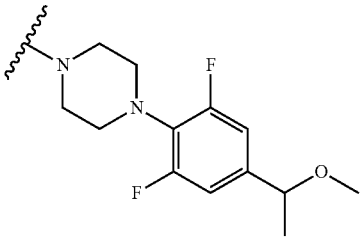 [SMILES: *N1CCN(c2c(F)cc(C(C)OC)cc2F)CC1] | 5-(4-(2,6-difluoro-4-(1-methoxyethyl)phenyl)piperazin-1-yl)-3-methyl-3H-[1,2,3]triazolo[4,5-d]pyrimidin-7(6H)-one | 29.97 |
| 19 | 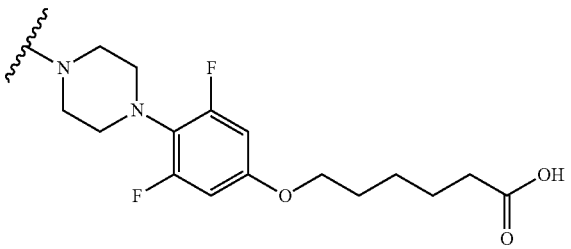 [SMILES: *N1CCN(c2c(F)cc(OCCCCCC(=O)O)cc2F)CC1] | 6-(3,5-difluoro-4-(4-(3-methyl-7-oxo-6,7-dihydro-3H-[1,2,3]triazo[4,5-d]pyrimidin-5-yl)piperazin-1-yl)phenoxy)hexanoic acid | 79.97 |
| 20 | 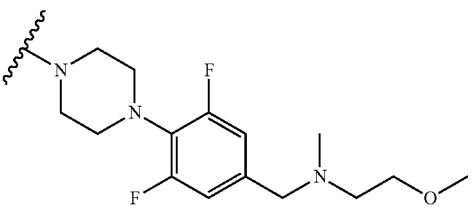 [SMILES: *N1CCN(c2c(F)cc(CN(C)CCOC)cc2F)CC1] | 5-(4-(2,6-difluoro-4-(((2-methoxyethyl)(methyl)amino)methyl)phenyl)piperazin-1-yl)-3-methyl-3H-[1,2(3]triazolo[4,5-d]pyrimidin-7(6H)-one | 83.12 |
| 21 | 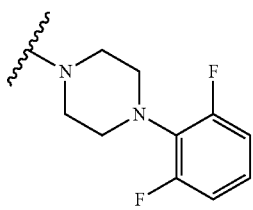 [SMILES: *N1CCN(c2c(F)cccc2F)CC1] | 5-(4-(2,6-difluorophenyl)piperazin-1-yl)-3-methyl-3H-[1,2,3]triazolo[4,5-d]pyrimidin-7(6H)-one | 8.90 |
| 22 | 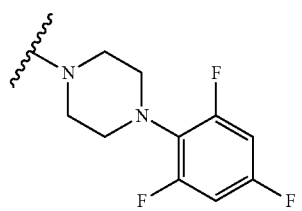 [SMILES: *N1CCN(c2c(F)cc(F)cc2F)CC1] | 3-methyl-5-(4-(2,4,6-trifluorophenyl)piperazin-1-yl)-3H-[1,2,3]triazolo[4,5-d]pyrimidin-7(6H)-one | 49.68 |
| 25 | 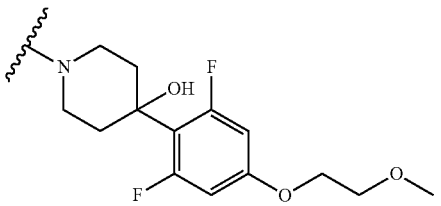 [SMILES: *N1CCC(O)(c2c(F)cc(OCCOC)cc2F)CC1] | 5-(4-(2,6-difluoro-4-(2-methoxyethoxy)phenyl)-4-hydroxypiperidin-1-yl)-3-methyl-3H-[1,2,3]triazolo[4,5-d]pyrimidin-7(6H)-one | 33.12 |
| 26 | 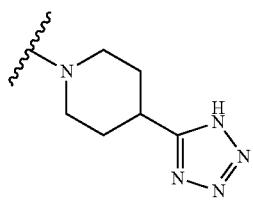 [SMILES: *N1CCC(c2nnn[nH]2)CC1] | 5-(4-(1H-tetrazol-5-yl)piperidin-1-yl)-3-methyl-3H-[1,2,3]triazolo[4,5-d]pyrimidin-7(6H)-one | 411.5 |

TABLE 1-continued

| Comp. | R group | IUPAC name | TNKS1 (IC$_{50}$) (nM) |
|---|---|---|---|
| 32 | 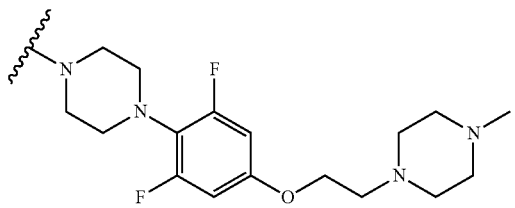 [SMILES: *N1CCN(c2c(F)cc(OCCN3CCN(C)CC3)cc2F)CC1] | 5-(4-(2,6-difluoro-4-(2-(4-methyl piperazin-1-yl)ethoxy)phenyl) piperazin-1-yl)-3-methyl-3H-[1,2,3]triazolo[4,5-d]pyrimidin-7(6H)-one | 119.5 |
| 33 | 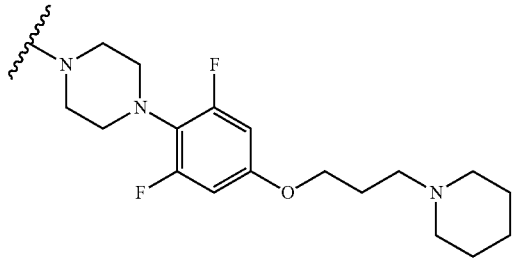 [SMILES: *N1CCN(c2c(F)cc(OCCCN3CCCCC3)cc2F)CC1] | 5-(4-(2,6-difluoro-4-(3-(piperidin-1-yl)propoxy)phenyl)piperazin-1-yl)-3-methyl-3H-[1,2,3]triazolo[4,5-d]pyrimidin-7(6H)-one | 51.3 |
| 34 | 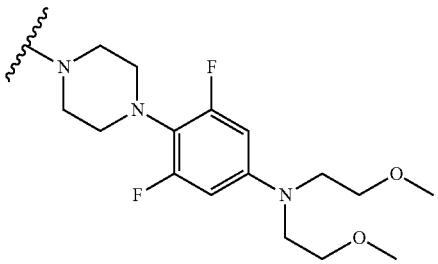 [SMILES: *N1CCN(c2c(F)cc(N(CCOC)CCOC)cc2F)CC1] | 5-(4-(4-(bis(2-methoxyethyl)amino)-2,6-difluorophenyl)piperazin-1-yl)-3-methyl-3H-[1,2,3]triazolo[4,5-d]pyrimidin-7(6H)-one | 67.73 |
| 35 | 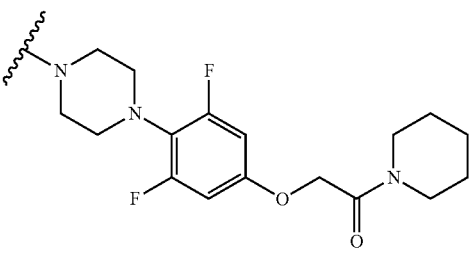 [SMILES: *N1CCN(c2c(F)cc(OCC(=O)N3CCCCC3)cc2F)CC1] | 5-(4-(2,6-difluoro-4-(2-oxo-2-(piperidin-1-yl)ethoxy)phenyl) piperazin-1-yl)-3-methyl-3H-[1,2,3]triazolo[4,5-d]pyrimidin-7(6H)-one | 48.69 |
| 36 | 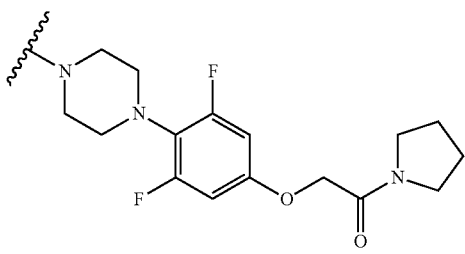 [SMILES: *N1CCN(c2c(F)cc(OCC(=O)N3CCCC3)cc2F)CC1] | 5-(4-(2,6-difluoro-4-(2-oxo-2-(pyrrolidin-1-yl)ethoxy)phenyl) piperazin-1-yl)-3-methyl-3H-[1,2,3]triazolo[4,5-d]pyrimidin-7(6H)-one | 39.55 |
| 37 | 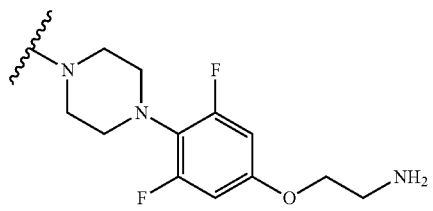 [SMILES: *N1CCN(c2c(F)cc(OCCN)cc2F)CC1] | 5-(4-(4-(2-aminoethoxy)-2,6-difluorophenyl)piperazin-1-yl)-3-methyl-3H-[1,2,3]triazolo[4,5-d]pyrimidin-7(6H)-one | 28.09 |

TABLE 1-continued

| Comp. | R group | IUPAC name | TNKS1 (IC$_{50}$) (nM) |
|---|---|---|---|
| 38 | | 5-(4-(2,6-difluoro-4-(2-(4-methyl-2-oxopiperazin-1-yl)ethoxy)phenyl)piperazin-1-yl)-3-methyl-3H-[1,2,3]triazolo[4,5-d]pyrimidin-7(6H)-one | 43 |
| 39 | | 5-(4-(4-(2-(4-aminopiperidin-1-yl)ethoxy)-2,6-difluoro phenyl)piperazin-1-yl)-3-methyl-3H-[1,2,3]triazolo[4,5-d]pyrimidin-7(6H)-one | 22.74 |
| 40 | | 5-(4-(2,6-difluoro-4-(3-methoxypropyl)phenyl)piperazin-1-yl)-3-methyl-3H-[1,2,3]triazolo[4,5-d]pyrimidin-7(6H)-one | 93.1 |
| 41 | | 5-(4-(2,6-difluoro-4-(2-(3-hydroxypyrrolidin-1-yl)ethoxy)phenyl)piperazin-1-yl)-3-methyl-3H-[1,2,3]triazolo[4,5-d]pyrimidin-7(6H)-one | 71.27 |
| 42 | | 5-(4-(2,6-difluoro-4-(2-(4-hydroxypiperidin-1-yl)ethoxy)phenyl)piperazin-1-yl)-3-methyl-3H-[1,2,3]triazolo[4,5-d]pyrimidin-7(6H)-one | 51.37 |
| 43 | | 5-(4-(2,6-difluoro-4-(2-(4-hydroxy-4-methylpiperidin-1-yl)ethoxy)phenyl)piperazin-1-yl)-3-methyl-3H-[1,2,3]triazolo[4,5-d]pyrimidin-7(6H)-one | 50.86 |
| 44 | | 5-(4-(2,6-difluoro-4-(2-methoxyethoxy)phenyl)-5,6-dihydropyridin-1(2H)-yl)-3-methyl-3H-[1,2,3]triazolo[4,5-d]pyrimidin-7(6H)-one | 52.93 |

TABLE 1-continued

| Comp. | R group | IUPAC name | TNKS1 (IC$_{50}$) (nM) |
|---|---|---|---|
| 45 | 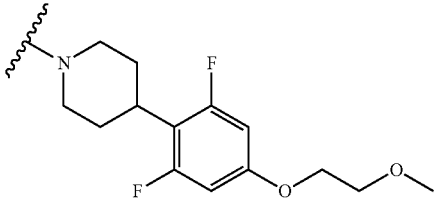 [SMILES: *N1CCC(c2c(F)cc(OCCOC)cc2F)CC1] | 5-(4-(2,6-difluoro-4-(2-methoxy ethoxy)phenyl)piperidin-1-yl)-3-methyl-3H-[1,2,3]triazolo[4,5-d]pyrimidin-7(6H)-one | 37.61 |

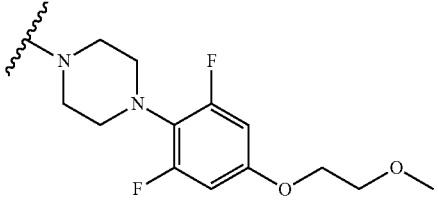

| 53 | 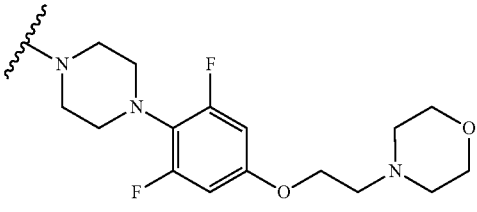 [SMILES: *N1CCN(c2c(F)cc(OCCN3CCOCC3)cc2F)CC1] | 6-(4-(2,6-difluoro-4-(2-methoxy ethoxy)phenyl)piperazin-1-yl)-1-methyl-1H-[1,2,3]triazolo[4,5-c]pyridin-4(5H)-one | 22.71 |
| 54 | 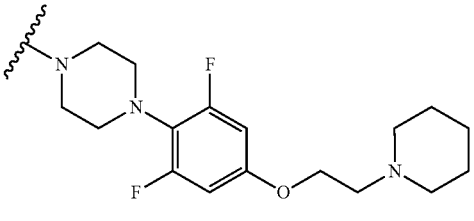 [SMILES: *N1CCN(c2c(F)cc(OCCN3CCCCC3)cc2F)CC1] | 6-(4-(2,6-difluoro-4-(2-morpholino ethoxy)phenyl)piperazin-1-yl)-1-methyl-1H-[1,2,3]triazolo[4,5-c]pyridin-4(5H)-one | 10.96 |
| 55 | 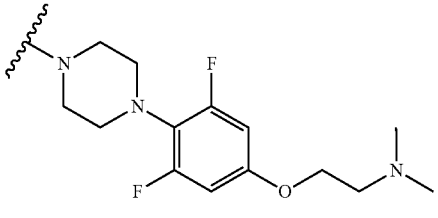 [SMILES: *N1CCN(c2c(F)cc(OCCN(C)C)cc2F)CC1] | 6-(4-(2,6-difluoro-4-(2-(piperidin-1-yl)ethoxy)phenyl)piperazin-1-yl)-1-methyl-1H-[1,2,3]triazolo[4,5-c]pyridin-4(5H)-one | 29.29 |
| 56 | 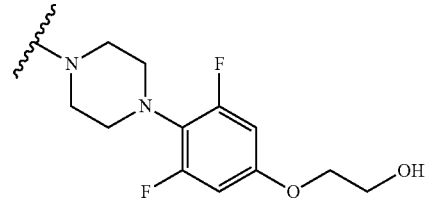 [SMILES: *N1CCN(c2c(F)cc(OCCO)cc2F)CC1] | 6-(4-(4-(2-(dimethylamino)ethoxy)-2,6-difluorophenyl)piperazin-1-yl)-1-methyl-1H-[1,2,3]triazolo[4,5-c]pyridin-4(5H)-one | 27.5 |
| 57 | | 6-(4-(2,6-difluoro-4-(2-hydroxy ethoxy)phenyl)piperazin-1-yl)-1-methyl-1H-[1,2,3]triazolo[4,5-c]pyridin-4(5H)-one | 7.976 |

TABLE 1-continued

| Comp. | R group | IUPAC name | TNKS1 (IC$_{50}$) (nM) |
|---|---|---|---|
| 58 | | (S)-2-(3,5-difluoro-4-(4-(1-methyl-4-oxo-4,5-dihydro-1H-[1,2,3]triazolo[4,5-c]pyridin-6-yl)piperazin-1-yl)phenoxy)ethyl 2-aminopropanoate hydrochloride | 13.36 |
| 59 | | 6-(4-(4-(2,3-dihydroxypropoxy)-2,6-difluorophenyl)piperazin-1-yl)-1-methyl-1H-[1,2,3]triazolo[4,5-c]pyridin-4(5H)-one | 15.96 |
| 60 | | 6-(4-(2,6-difluoro-4-(morpholinomethyl)phenyl)piperazin-1-yl)-1-methyl-1H-[1,2,3]triazolo[4,5-c]pyridin-4(5H)-one | 25.78 |
| 61 | | 6-(4-(2,6-difluoro-4-((4-methylpiperazin-1-yl)methyl)phenyl)piperazin-1-yl)-1-methyl-1H-[1,2,3]triazolo[4,5-c]pyridin-4(5H)-one | 28.23 |
| 62 | | 6-(4-(2,6-difluoro-4-(oxetan-3-yloxy)phenyl)piperazin-1-yl)-1-methyl-1H-[1,2,3]triazolo[4,5-c]pyridin-4(5H)-one | 22.14 |
| 63 | | 6-(4-(2,6-difluoro-4-(1-hydroxyethyl)phenyl)piperazin-1-yl)-1-methyl-1H-[1,2,3]triazolo[4,5-c]pyridin-4(5H)-one | 27.33 |

TABLE 1-continued

| Comp. | R group | IUPAC name | TNKS1 (IC$_{50}$) (nM) |
|---|---|---|---|
| 64 | 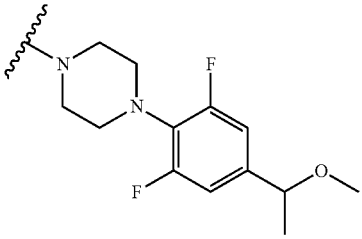 [SMILES: *N1CCN(c2c(F)cc(C(C)OC)cc2F)CC1] | 6-(4-(2,6-difluoro-4-(1-methoxy ethyl)phenyl)piperazin-1-yl)-1-methyl-1H-[1,2,3]triazolo[4,5-c]pyridin-4(5H)-one | 31.16 |
| 65 | 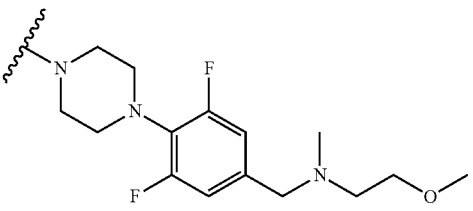 [SMILES: *N1CCN(c2c(F)cc(CN(C)CCOC)cc2F)CC1] | 6-(4-(2,6-difluoro-4-(((2-methoxy ethyl)(methyl)amino)methyl)phenyl) piperazin-1-yl)-1-methyl-1H-[1,2,3] triazolo[4,5-c]pyridin-4(5H)-one | 40.23 |
| 66 | 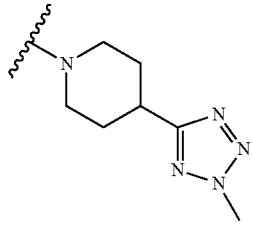 [SMILES: *N1CCC(c2nnn(C)n2)CC1] | 1-methyl-6-(4-(2-methyl-2H-tetrazol-5-yl)piperidin-1-yl)-1H-[1,2,3]triazolo[4,5-c]pyridin-4(5H)-one | 330.7 |
| 67 | 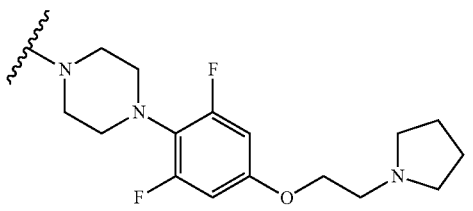 [SMILES: *N1CCN(c2c(F)cc(OCCN3CCCC3)cc2F)CC1] | 6-(4-(2,6-difluoro-4-(2-(pyrrolidin-1-yl)ethoxy)phenyl)piperazin-1-yl)-1-methyl-1H-[1,2,3]triazolo[4,5-c]pyridin-4(5H)-one | 18.57 |
| 68 | 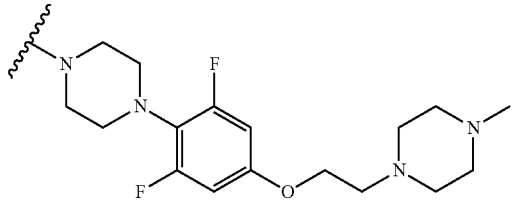 [SMILES: *N1CCN(c2c(F)cc(OCCN3CCN(C)CC3)cc2F)CC1] | 6-(4-(2,6-difluoro-4-(2-(4-methylpiperazin-1-yl) ethoxy)phenyl)piperazin-1-yl)-1-methyl-1H-[1,2,3]triazolo [4,5-c]pyridin-4(5H)-one | 14.23 |
| 69 | 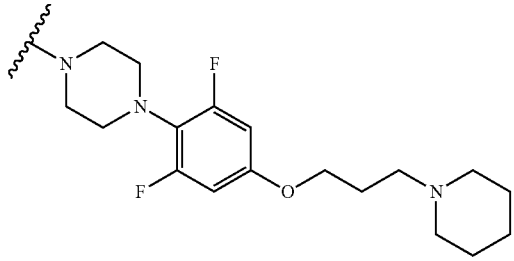 [SMILES: *N1CCN(c2c(F)cc(OCCCN3CCCCC3)cc2F)CC1] | 6-(4-(2,6-difluoro-4-(3-(piperidin-1-yl)propoxy) phenyl)piperazin-1-yl)-1-methyl-1H-[1,2,3]triazolo[4,5-c]pyridin-4(5H)-one | 19.1 |

TABLE 1-continued

| Comp. | R group | IUPAC name | TNKS1 (IC$_{50}$) (nM) |
|---|---|---|---|
| 70 | | 6-(4-(2,6-difluoro-4-(2-oxo-2-(pyrrolidin-1-yl)ethoxy)phenyl)piperazin-1-yl)-1-methyl-1H-[1,2,3]triazolo[4,5-c]pyridin-4(5H)-one | 15.58 |
| 71 | | 6-(4-(4-(2-aminoethoxy)-2,6-difluorophenyl)piperazin-1-yl)-1-methyl-1H-[1,2,3]triazolo[4,5-c]pyridin-4(5H)-one | 24.9 |
| 72 | | 6-(4-(4-(2-(4-aminopiperidin-1-yl)ethoxy)-2,6-difluorophenyl)piperazin-1-yl)-1-methyl-1H-[1,2,3]triazolo[4,5-c]pyridin-4(5H)-one | 7.312 |

The invention claimed is:

1. A compound represented by Chemical Formula 1, a tautomer thereof, a stereoisomer thereof, or a mixture thereof, or a pharmaceutically acceptable salt thereof:

[Chemical Formula 1]

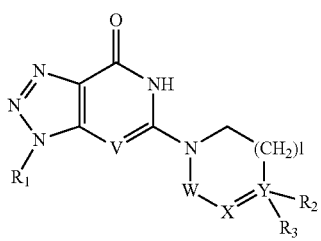

wherein

V is N or CH;

R$_1$ is hydrogen, or C$_{1-6}$ alkyl;

W is CH$_2$;

X is CHR$_4$;

Y is N or C;

----- is a single bond or a double bond, determined by X and Y;

l is 1;

R$_2$ is none, hydrogen, or hydroxyl;

R$_3$ is

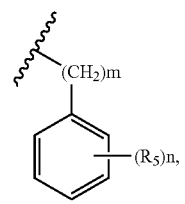

or heteroaryl;

R$_4$ is none, or hydrogen;

m is 0, or 1;

n is 0, 1, 2, or 3;

each of R$_5$ is independently halo, C$_{2-6}$ alkenyl, C$_{1-6}$ hydroxyalkyl, or —Z—(CH$_2$)$_p$—R$_6$;

p is 0, 1, 2, 3, 4, 5 or 6;

Z is —O—, or none;

R$_6$ is hydroxyl, C$_{1-6}$ alkoxy, C$_{1-3}$ alkoxy-C$_{1-3}$ alkyl, C$_{5-10}$ aryl, carboxy, C$_{1-6}$ dihydroxyalkyl, C$_{1-6}$ alkyl, C$_{1-6}$ haloalkyl optionally substituted with hydroxy, heterocyclyl, heteroaryl, —O—(C=O)—R$_8$, —(C=O)—R$_8$, —OR$_8$, —COOR$_8$, or —NR$_9$R$_{10}$;

R$_8$ is hydrogen, C$_{1-6}$ alkyl, C$_{1-6}$ aminoalkyl, or heterocyclyl;

each of R$_9$ and R$_{10}$ is independently hydrogen, C$_{1-6}$ alkyl, or C$_{1-3}$ alkoxy-C$_{1-3}$ alkyl;

each of the heteroaryls is a 5- to 10-membered single ring containing one or more nitrogen atom, and each of the heterocyclyls may be a 3- to 10-membered single ring containing one or more heteroatom selected from the group consisting of N, O, and a combination thereof;

each of the heterocyclyls may optionally be substituted with one to three substituents selected from the group consisting of $C_{1-6}$ alkyl, hydroxyl, and oxo, or amino; and each of the aryls and heteroaryls may optionally be substituted with one to three $C_{1-6}$ alkyl.

2. The compound according to claim 1,
wherein
m is 0; and
n is 1, 2 or 3,
or a tautomer thereof, a stereoisomer thereof, or a mixture thereof, or a pharmaceutically acceptable salt thereof.

3. The compound according to claim 1,
wherein
m is 0;
n is 1, 2 or 3;
each of $R_5$ is independently fluoro, hydroxyethyl, or —Z—$(CH_2)_p$—$R_6$;
Z is —O—, or none;
$R_6$ is hydroxyl, methoxy, ethoxy, methoxyethyl, $C_{5-10}$ aryl, carboxy, 1,2-dihydroxyethyl, 1-chloro-3-hydroxyisopropyl, perfluoromethyl, heterocyclyl, heteroaryl, —O—(C=O)—$R_8$, —(C=O)—$R_8$, or —$NR_9R_{10}$;
$R_8$ is hydrogen, methyl, or aminoethyl;
each of $R_9$ and $R_{10}$ is independently hydrogen, methyl, ethyl or methoxyethyl;
each of the heteroaryls may be a 5- to 10-membered single ring containing one or more nitrogen atom, and each of the heterocyclyls may be a 3- to 10-membered single ring containing one or more heteroatom selected from the group consisting of N, O, and a combination thereof;
each of the heterocyclyls may optionally be substituted with one to three substituents selected from the group consisting of methyl, hydroxyl, amino and oxo; and
each of the heteroaryls may optionally be substituted with one to three methyl,
or a tautomer thereof, a stereoisomer thereof, or a mixture thereof, or a pharmaceutically acceptable salt thereof.

4. The compound according to claim 3,
wherein
each of the aryls is phenyl or naphthyl;
each of the heteroaryls may be selected from the group consisting of tetrazolyl, imidazolyl, pyridinyl, pyridazinyl, pyrimidyl, triazinyl, pyrrolyl, pyrazolyl, triazolyl, or pyrazinyl; and
each of the heterocyclyls may be selected from the group consisting of tetrahydropyranyl, tetrahydrofuranyl, dihydrofuranyl, dihydropyranyl, dioxanyl, dioxolanyl, imidazolidinyl, oxetanyl, pyrrolidinyl, piperidinyl, piperazinyl, morpholinyl, oxopiperidinyl, oxopyrrolidinyl and oxooxazolidinyl, or
a tautomer thereof, a stereoisomer thereof, or a mixture thereof, or a pharmaceutically acceptable salt thereof.

5. The compound according to claim 4,
wherein
each of the aryls is phenyl;
each of the heteroaryls is tetrazolyl or imidazolyl; and
each of the heterocyclyls is tetrahydrofuranyl, oxetanyl, pyrrolidinyl, piperidinyl, piperazinyl or morpholinyl, or a tautomer thereof, a stereoisomer thereof, or a mixture thereof, or a pharmaceutically acceptable salt thereof.

6. The compound according to claim 5,
wherein
each of the heterocyclyls is tetrahydrofuranyl, oxetanyl, pyrrolidinyl, piperidinyl, piperazinyl, morpholinyl, 4-methylpiperazinyl, 4-methyl-2-oxopiperazinyl, 3-hydroxypyrrolidinyl, 2-hydroxymethylpyrrolidinyl, N-methylpyrrolidinyl, 4-hydroxypiperidinyl, 4-hydroxy-4-methylpiperidinyl, 4-aminopiperidinyl, 2-oxopiperidinyl, or 2,6-dimethylpiperidinyl,
or a tautomer thereof, a stereoisomer thereof, or a mixture thereof, or a pharmaceutically acceptable salt thereof.

7. The compound according to claim 1,
wherein the compound is selected from a group consisting of
1) 5-(4-(2-fluorophenyl)piperazin-1-yl)-3-methyl-3H-[1,2,3]triazolo[4,5-d]pyrimidin-7(6H)-one,
2) 5-(4-(2,6-difluoro-4-(2-methoxyethoxy)phenyl)piperazin-1-yl)-3-methyl-3H-[1,2,3]triazolo[4,5-d]pyrimidin-7(6H)-one,
3) 5-(4-(4-(benzyloxy)-2,6-difluorophenyl)piperazin-1-yl)-3-methyl-3H-[1,2,3]triazolo[4,5-d]pyrimidin-7(6H)-one,
4) 5-(4-(2,6-difluoro-4-(2-morpholinoethoxy)phenyl)piperazin-1-yl)-3-methyl-3H-[1,2,3]triazolo[4,5-d]pyrimidin-7(6H)-one,
5) 5-(4-(2,6-difluoro-4-(2-(piperidin-1-yl)ethoxy)phenyl)piperazin-1-yl)-3-methyl-3H-[1,2,3]triazolo[4,5-d]pyrimidin-7(6H)-one,
6) 5-(4-(4-(2-(dimethylamino)ethoxy)-2,6-difluorophenyl)piperazin-1-yl)-3-methyl-3H-[1,2,3]triazolo[4,5-d]pyrimidin-7(6H)-one,
7) 5-(4-(2,6-difluoro-4-(2-hydroxyethoxy)phenyl)piperazin-1-yl)-3-methyl-3H-[1,2,3]triazolo[4,5-d]pyrimidin-7(6H)-one,
8) 2-(3,5-difluoro-4-(4-(3-methyl-7-oxo-6,7-dihydro-3H-[1,2,3]triazolo[4,5-d]pyrimidin-5-yl)piperazin-1-yl)phenoxy)ethyl acetate,
9) 5-(4-(2,6-difluoro-4-isopropoxyphenyl)piperazin-1-yl)-3-methyl-3H-[1,2,3]triazolo[4,5-d]pyrimidin-7(6H)-one,
10) (R)-2-(3,5-difluoro-4-(4-(3-methyl-7-oxo-6,7-dihydro-3H-[1,2,3]triazolo[4,5-d]pyrimidin-5-yl)piperazin-1-yl)phenoxy)ethoxy)-1-oxopropan-2-aminium chloride,
11) (S)-2-(3,5-difluoro-4-(4-(3-methyl-7-oxo-6,7-dihydro-3H-[1,2,3]triazolo[4,5-d]pyrimidin-5-yl)piperazin-1-yl)phenoxy)ethoxy)-1-oxopropan-2-aminium chloride,
12) 5-(4-(4-(2,3-dihydroxypropoxy)-2,6-difluorophenyl)piperazin-1-yl)-3-methyl-3H-[1,2,3]triazolo[4,5-d]pyrimidin-7(6H)-one,
13) 5-(4-(2,6-difluoro-4-(morpholinomethyl)phenyl)piperazin-1-yl)-3-methyl-3H-[1,2,3]triazolo[4,5-d]pyrimidin-7(6H)-one,
14) 5-(4-(2,6-difluoro-4-((4-methylpiperazin-1-yl)methyl)phenyl)piperazin-1-yl)-3-methyl-3H-[1,2,3]triazolo[4,5-d]pyrimidin-7(6H)-one,
15) 5-(4-(2,6-difluoro-4-(oxetan-3-yloxy)phenyl)piperazin-1-yl)-3-methyl-3H-[1,2,3]triazolo[4,5-d]pyrimidin-7(6H)-one,
16) 5-(4-(4-(1-chloro-3-hydroxypropan-2-yloxy)-2,6-difluorophenyl)piperazin-1-yl)-3-methyl-3H-[1,2,3]triazolo[4,5-d]pyrimidin-7(6H)-one,
17) 5-(4-(2,6-difluoro-4-(1-hydroxyethyl)phenyl)piperazin-1-yl)-3-methyl-3H-[1,2,3]triazolo[4,5-d]pyrimidin-7(6H)-one, 18) 5-(4-(2,6-difluoro-4-(1-methoxyethyl)phenyl)piperazin-1-yl)-3-methyl-3H-[1,2,3]triazolo[4,5-d]pyrimidin-7(6H)-one,
19) 6-(3,5-difluoro-4-(4-(3-methyl-7-oxo-6,7-dihydro-3H-[1,2,3]triazo[4,5-d]pyrimidin-5-yl)piperazin-1-yl)phenoxy)hexanoic acid,
20) 5-(4-(2,6-difluoro-4-(((2-methoxyethyl)(methyl)amino)methyl)phenyl)piperazin-1-yl)-3-methyl-3H-[1,2,3]triazolo[4,5-d]pyrimidin-7(6H)-one,
21) 5-(4-(2,6-difluorophenyl)piperazin-1-yl)-3-methyl-3H-[1,2,3]triazolo[4,5-d]pyrimidin-7(6H)-one,
22) 3-methyl-5-(4-(2,4,6-trifluorophenyl)piperazin-1-yl)-3H-[1,2,3]triazolo[4,5-d]pyrimidin-7(6H)-one,
23) 5-(4-(4-(1,2-dihydroxyethyl)-2,6-difluorophenyl)piperazin-1-yl)-3-methyl-3H-[1,2,3]triazolo[4,5-d]pyrimidin-7(6H)-one,
24) 5-(4-(4-(2,3-dihydroxypropyl)-2,6-difluorophenyl)piperazin-1-yl)-3-methyl-3H-[1,2,3]triazolo[4,5-d]pyrimidin-7(6H)-one,
25) 5-(4-(2,6-difluoro-4-(2-methoxyethoxy)phenyl)-4-hydroxypiperidin-1-yl)-3-methyl-3H-[1,2,3]triazolo[4,5-d]pyrimidin-7(6H)-one,
26) 5-(4-(1H-tetrazol-5-yl)piperidin-1-yl)-3-methyl-3H-[1,2,3]triazolo[4,5-d]pyrimidin-7(6H)-one,
27) 5-(4-(2,6-difluoro-4-(2-methoxyethylamino)phenyl)piperazin-1-yl)-3-methyl-3H-[1,2,3]triazolo[4,5-d]pyrimidin-7(6H)-one,
28) 5-(4-(2,6-difluoro-4-vinylphenyl)piperazin-1-yl)-3-methyl-3H-[1,2,3]triazolo[4,5-d]pyrimidin-7(6H)-one,
29) 3-methyl-5-(4-(1-methyl-1H-tetrazol-5-yl)piperidin-1-yl)-3H-[1,2,3]triazolo[4,5-d]pyrimidin-7(6H)-one,
30) 3-methyl-5-(4-(2-methyl-2H-tetrazol-5-yl)piperidin-1-yl)-3H-[1,2,3]triazolo[4,5-d]pyrimidin-7(6H)-one,
31) 5-(4-(2,6-difluoro-4-(2-(pyrrolidin-1-yl)ethoxy)phenyl)piperazin-1-yl)-3-methyl-3H-[1,2,3]triazolo[4,5-d]pyrimidin-7(6H)-one,
32) 5-(4-(2,6-difluoro-4-(2-(4-methylpiperazin-1-yl)ethoxy)phenyl) piperazin-1-yl)-3-methyl-3H-[1,2,3]triazolo[4,5-d]pyrimidin-7(6H)-one,
33) 5-(4-(2,6-difluoro-4-(3-(piperidin-1-yl)propoxy)phenyl)piperazin-1-yl)-3-methyl-3H-[1,2,3]triazolo[4,5-d]pyrimidin-7(6H)-one,
34) 5-(4-(4-(bis(2-methoxyethyl)amino)-2,6-difluorophenyl)piperazin-1-yl)-3-methyl-3H-[1,2,3]triazolo[4,5-d]pyrimidin-7(6H)-one,
35) 5-(4-(2,6-difluoro-4-(2-oxo-2-(piperidin-1-yl)ethoxy)phenyl) piperazin-1-yl)-3-methyl-3H-[1,2,3]triazolo[4,5-d]pyrimidin-7(6H)-one,
36) 5-(4-(2,6-difluoro-4-(2-oxo-2-(pyrrolidin-1-yl)ethoxy)phenyl) piperazin-1-yl)-3-methyl-3H-[1,2,3]triazolo[4,5-d]pyrimidin-7(6H)-one,
37) 5-(4-(4-(2-aminoethoxy)-2,6-difluorophenyl)piperazin-1-yl)-3-methyl-3H-[1,2,3]triazolo[4,5-d]pyrimidin-7(6H)-one,
38) 5-(4-(2,6-difluoro-4-(2-(4-methyl-2-oxopiperazin-1-yl) ethoxy)phenyl)piperazin-1-yl)-3-methyl-3H-[1,2,3]triazolo[4,5-d]pyrimidin-7(6H)-one,
39) 5-(4-(4-(2-(4-aminopiperidin-1-yl)ethoxy)-2,6-difluoro phenyl)piperazin-1-yl)-3-methyl-3H-[1,2,3]triazolo[4,5-d]pyrimidin-7(6H)-one,
40) 5-(4-(2,6-difluoro-4-(3-methoxypropyl)phenyl)piperazin-1-yl)-3-methyl-3H-[1,2,3]triazolo[4,5-d]pyrimidin-7(6H)-one,
41) 5-(4-(2,6-difluoro-4-(2-(3-hydroxypyrrolidin-1-yl)ethoxy)phenyl)piperazin-1-yl)-3-methyl-3H-[1,2,3]triazolo[4,5-d]pyrimidin-7(6H)-one,
42) 5-(4-(2,6-difluoro-4-(2-(4-hydroxypiperidin-1-yl)ethoxy) phenyl)piperazin-1-yl)-3-methyl-3H-[1,2,3]triazolo[4,5-d]pyrimidin-7(6H)-one,
43) 5-(4-(2,6-difluoro-4-(2-(4-hydroxy-4-methylpiperidin-1-yl)ethoxy)phenyl)piperazin-1-yl)-3-methyl-3H-[1,2,3]triazolo[4,5-d]pyrimidin-7(6H)-one,
44) 5-(4-(2,6-difluoro-4-(2-methoxyethoxy)phenyl)-5,6-dihydropyridin-1(2H)-yl)-3-methyl-3H-[1,2,3]triazolo[4,5-d]pyrimidin-7(6H)-one,
45) 5-(4-(2,6-difluoro-4-(2-methoxyethoxy)phenyl)piperidin-1-yl)-3-methyl-3H-[1,2,3]triazolo[4,5-d]pyrimidin-7(6H)-one,
46) 5-(4-(2,6-difluoro-4-(2-(2-oxopiperidin-1-yl)ethoxy) phenyl)piperazin-1-yl)-3-methyl-3H-[1,2,3]triazolo[4,5-d]pyrimidin-7(6H)-one,
47) 5-(4-(4-(2-ethoxyethoxy)-2,6-difluorophenyl)piperazin-1-yl)-3-methyl-3H-[1,2,3]triazolo[4,5-d]pyrimidin-7(6H)-one,
48) 5-(4-(4-(2-(cis-2,6-dimethylpiperidin-1-yl)ethoxy)-2,6-difluorophenyl)piperazin-1-yl)-3-methyl-3H-[1,2,3]triazolo[4,5-d]pyrimidin-7(6H)-one,
49) 5-(4-(4-(2-(4,4-difluoropiperidin-1-yl)ethoxy)-2,6-difluorophenyl)piperazin-1-yl)-3-methyl-3H-[1,2,3]triazolo[4,5-d]pyrimidin-7(6H)-one,
50) 5-(4-(4-(2-(diethylamino)ethoxy)-2,6-difluorophenyl)piperazin-1-yl)-3-methyl-3H-[1,2,3]triazolo[4,5-d]pyrimidin-7(6H)-one,
51) 5-(4-(4-(2-(1H-imidazol-1-yl)ethoxy)-2,6-difluorophenyl)piperazin-1-yl)-3-methyl-3H-[1,2,3]triazolo[4,5-d]pyrimidin-7(6H)-one,
52) 5-(4-(2,6-difluoro-4-((tetrahydrofuran-2-yl)methoxy)phenyl)piperazin-1-yl)-3-methyl-3H-[1,2,3]triazolo[4,5-d]pyrimidin-7(6H)-one,
53) 6-(4-(2,6-difluoro-4-(2-methoxyethoxy)phenyl)piperazin-1-yl)-1-methyl-1H-[1,2,3]triazolo[4,5-c]pyridin-4(5H)-one,
54) 6-(4-(2,6-difluoro-4-(2-morpholinoethoxy)phenyl)piperazin-1-yl)-1-methyl-1H-[1,2,3]triazolo[4,5-c]pyridin-4(5H)-one,
55) 6-(4-(2,6-difluoro-4-(2-(piperidin-1-yl)ethoxy)phenyl)piperazin-1-yl)-1-methyl-1H-[1,2,3]triazolo[4,5-c]pyridin-4(5H)-one,
56) 6-(4-(4-(2-(dimethylamino)ethoxy)-2,6-difluorophenyl)piperazin-1-yl)-1-methyl-1H-[1,2,3]triazolo[4,5-c]pyridin-4(5H)-one,
57) 6-(4-(2,6-difluoro-4-(2-hydroxyethoxy)phenyl)piperazin-1-yl)-1-methyl-1H-[1,2,3]triazolo[4,5-c]pyridin-4(5H)-one,
58) (S)-2-(3,5-difluoro-4-(4-(1-methyl-4-oxo-4,5-dihydro-1H-[1,2,3]triazolo[4,5-c]pyridin-6-yl)piperazin-1-yl)phenoxy)ethyl2-aminopropanoate hydrochloride,
59) 6-(4-(4-(2,3-dihydroxypropoxy)-2,6-difluorophenyl)piperazin-1-yl)-1-methyl-1H-[1,2,3]triazolo[4,5-c]pyridin-4(5H)-one,
60) 6-(4-(2,6-difluoro-4-(morpholinomethyl)phenyl)piperazin-1-yl)-1-methyl-1H-[1,2,3]triazolo[4,5-c]pyridin-4(5H)-one,
61) 6-(4-(2,6-difluoro-4-((4-methylpiperazin-1-yl)methyl)phenyl) piperazin-1-yl)-1-methyl-1H-[1,2,3]triazolo[4,5-c]pyridin-4(5H)-one,
62) 6-(4-(2,6-difluoro-4-(oxetan-3-yloxy)phenyl)piperazin-1-yl)-1-methyl-1H-[1,2,3]triazolo[4,5-c]pyridin-4(5H)-one,
63) 6-(4-(2,6-difluoro-4-(1-hydroxyethyl)phenyl)piperazin-1-yl)-1-methyl-1H-[1,2,3]triazolo[4,5-c]pyridin-4(5H)-one, 64) 6-(4-(2,6-difluoro-4-(1-methoxyethyl)phenyl)piperazin-1-yl)-1-methyl-1H-[1,2,3]triazolo[4,5-c]pyridin-4(5H)-one,
65) 6-(4-(2,6-difluoro-4-(((2-methoxy ethyl)(methyl)amino)methyl)phenyl)piperazin-1-yl)-1-methyl-1H-[1,2,3]triazolo[4,5-c]pyridin-4(5H)-one,
66) 1-methyl-6-(4-(2-methyl-2H-tetrazol-5-yl)piperidin-1-yl)-1H-[1,2,3]triazolo[4,5-c]pyridin-4(5H)-one,
67) 6-(4-(2,6-difluoro-4-(2-(pyrrolidin-1-yl)ethoxy)phenyl)piperazin-1-yl)-1-methyl-1H-[1,2,3]triazolo[4,5-c]pyridin-4(5H)-one,
68) 6-(4-(2,6-difluoro-4-(2-(4-methylpiperazin-1-yl)ethoxy)phenyl)piperazin-1-yl)-1-methyl-1H-[1,2,3]triazolo[4,5-c]pyridin-4(5H)-one,
69) 6-(4-(2,6-difluoro-4-(3-(piperidin-1-yl)propoxy)phenyl)piperazin-1-yl)-1-methyl-1H-[1,2,3]triazolo[4,5-c]pyridin-4(5H)-one,
70) 6-(4-(2,6-difluoro-4-(2-oxo-2-(pyrrolidin-1-yl)ethoxy) phenyl)piperazin-1-yl)-1-methyl-1H-[1,2,3]triazolo[4,5-c]pyridin-4(5H)-one,
71) 6-(4-(4-(2-aminoethoxy)-2,6-difluorophenyl)piperazin-1-yl)-1-methyl-1H-[1,2,3]triazolo[4,5-c]pyridin-4(5H)-one,
72) 6-(4-(4-(2-(4-aminopiperidin-1-yl)ethoxy)-2,6-difluoro phenyl)piperazin-1-yl)-1-methyl-1H-[1,2,3]triazolo[4,5-c]pyridin-4(5H)-one, and
73) 5-(4-(2,6-difluoro-4-(2-methoxyethoxy)phenyl)piperazin-1-yl)-3H-[1,2,3]triazolo[4,5-d]pyrimidin-7(6H)-one, or a tautomer thereof, a stereoisomer thereof, or a mixture thereof, or a pharmaceutically acceptable salt thereof.

8. A pharmaceutical composition comprising the compound according to claim 1, or a tautomer thereof, a stereoisomer thereof, or a mixture thereof, or a pharmaceutically acceptable salt thereof as an active ingredient, together with at least one pharmaceutically acceptable carrier, diluent, or excipient.

* * * * *